(12) United States Patent
Sherer et al.

(10) Patent No.: US 11,845,958 B2
(45) Date of Patent: Dec. 19, 2023

(54) GENETICALLY MODIFIED GENES AND CELLS, AND METHODS OF USING SAME FOR SILENCING VIRUS GENE EXPRESSION

(71) Applicant: Wisconsin Alumni Research Foundation, Madison, WI (US)

(72) Inventors: Nathan Mark Sherer, Madison, WI (US); Ryan Thomas Behrens, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 524 days.

(21) Appl. No.: 16/561,847

(22) Filed: Sep. 5, 2019

(65) Prior Publication Data
US 2020/0071671 A1 Mar. 5, 2020

Related U.S. Application Data

(60) Provisional application No. 62/727,363, filed on Sep. 5, 2018.

(51) Int. Cl.
| | |
|---|---|
| *C12N 5/0783* | (2010.01) |
| *C07K 14/47* | (2006.01) |
| *C07K 14/705* | (2006.01) |
| *A61K 35/17* | (2015.01) |
| *A61K 38/16* | (2006.01) |
| *C12N 15/00* | (2006.01) |
| *C12N 15/09* | (2006.01) |
| *A61K 38/00* | (2006.01) |

(52) U.S. Cl.
CPC ............ *C12N 5/0637* (2013.01); *A61K 35/17* (2013.01); *A61K 38/16* (2013.01); *C07K 14/4705* (2013.01); *C07K 14/705* (2013.01); *C12N 15/00* (2013.01); *C12N 15/09* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 2003/0087273 A1* | 5/2003 | Holzmayer | ...... | G01N 33/56988 435/5 |
| 2016/0145646 A1* | 5/2016 | Frendewey | .......... | C12Q 1/6888 800/24 |

FOREIGN PATENT DOCUMENTS

WO    WO-2014191128 A1 * 12/2014    ............. A61K 35/17

OTHER PUBLICATIONS

Fujinaga et al., Interactions between human cyclin T, Tat, and the transactivation response element (TAR) are disrupted by a cysteine to tyrosine substitution found in mouse cyclin T (PNAS, 1999, 96:1285-1290) (Year: 1999).*
Schumann et al., Generation of knock-in primary human T cells using Cas9 ribonucleoproteins (PNAS, 2015, 112:10437-42) (Year: 2015).*
Evans et al., HIV-1 Vif's Capacity to Manipulate the Cell Cycle Is Species Specific. J Virol. Apr. 1, 2018; 92(7): e02102-17. (Year: 2018).*
Altschul et al. Gapped BLAST and PSI-BLAST: a new generation of protein database search programs. *Nucleic Acids Research*. 1997. 25:3389-3402.
Bieniasz PD, Grdina TA, Bogerd HP, Cullen BR. Recruitment of a protein complex containing Tat and cyclin T1 to TAR governs the species specificity of HIV-1 Tat. *The EMBO Journal*. Dec. 1, 1998. 17(23):7056-7065. PMCID: PMC1171053.
Calvanese V, Chavez L, Laurent T, Ding S, Verdin E. Dual-color HIV reporters trace a population of latently infected cells and enable their purification. *Virology*. Nov. 2013. 446(1-2):283-292. PMCID: PMC4019006.
Devereux et al., a comprehensive set of sequence analysis programs for the VAX, *Nucleic Acids Research*. 1984. 12:387-395.
Edgar, R.C., Muscle: a multiple sequence alignment method with reduced time and space complexity. *BMC Bioinformatics*. 2004. 5:113.
Fornerod M, Ohno M, Yoshida M, Mattaj IW. CRM1 Is an Export Receptor for Leucine-Rich Nuclear Export Signals. *Cell*. Sep. 19, 1997. 90(6):1051-1060.
Garber ME, Wei P, Kewalramani VN, Mayall TP, Herrmann Ch, Rice AP, Littman DR, Jones KA. The interaction between HIV-1 Tat and human cyclin T1 requires zinc and a critical cysteine residue that is not conserved in the murine CycT1 protein. *Genes and Development*. Nov. 15, 1998. 12(22):3512-3527. PMCID: PMC317238.
Kane M, Yadav SS, Bitzegeio J, Kutluay SB, Zang T, Wilson SJ, Schoggins JW, Rice CM, Yamashita M, Hatziioannou T, Bieniasz PD. MX2 is an interferon-induced inhibitor of HIV-1 infection. *Nature*. Oct. 24, 2013. 502(7472):563-566.

(Continued)

*Primary Examiner* — Arthur S Leonard
(74) *Attorney, Agent, or Firm* — Daniel A. Blasiole; DeWitt LLP

(57) ABSTRACT

Genetically modified CCNT1 and XPO1 genes encoding proteins that inhibit virus infection in cells. The genetically modified CCNT1 gene encodes a protein with a C261Y substitution with respect to the human CCNT1 protein. The genetically modified XPO1 gene encodes a protein with P411T, M412V, and/or F414S substitutions with respect to the human XPO1 protein. The genetically modified CCNT1 and XPO1 genes can be introduced in cells. The cells comprising the genetically modified CCNT1 and XPO1 genes can be introduced in a subject with a virus infection to treat the infection.

Figure 3:
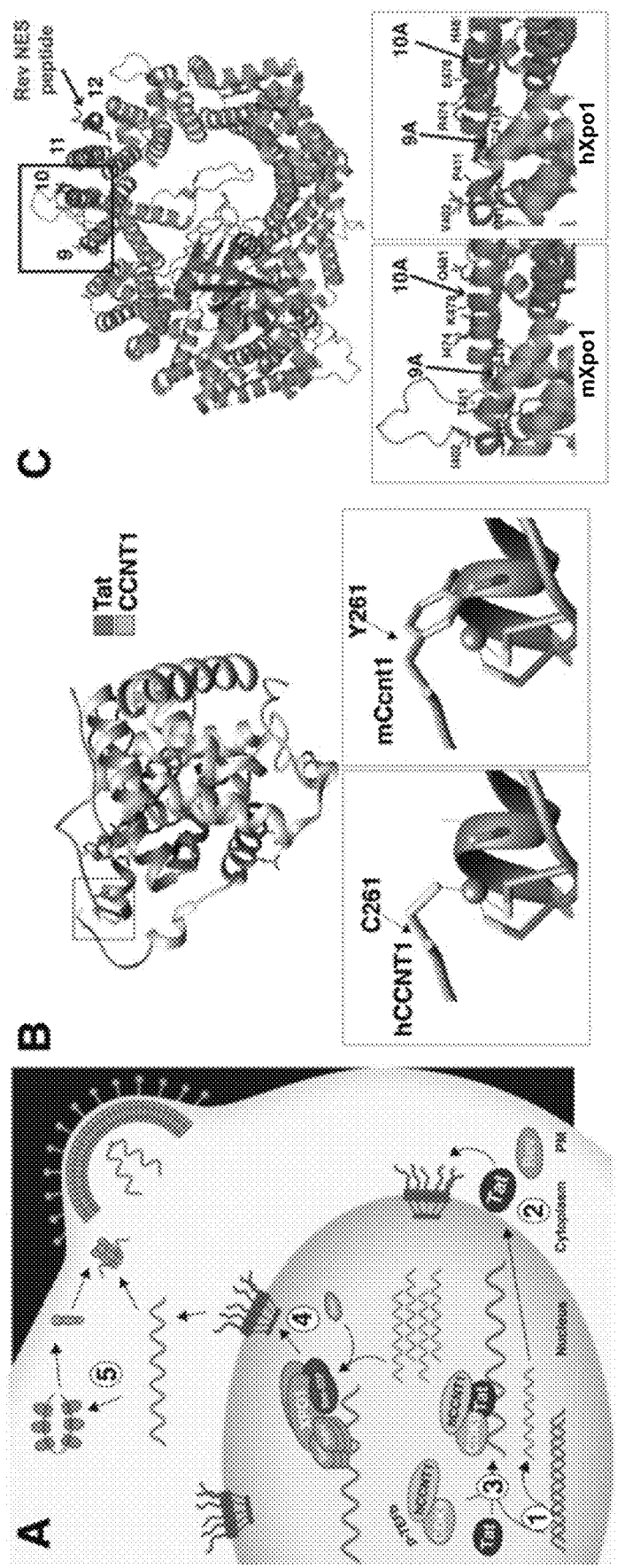

24 Claims, 19 Drawing Sheets
(13 of 19 Drawing Sheet(s) Filed in Color)
Specification includes a Sequence Listing.

(56) References Cited

OTHER PUBLICATIONS

Knoener RA, Becker JT, Scalf M, Sherer NM, Smith LM. Elucidating the in vivo interactome of HIV-1 RNA by hybridization capture and mass spectrometry. *Scientific Reports*. 2017. 7:16965.
Larkin M. A., et al. ClustalW2, ClustalW and ClustalX version 2. *Bioinformatics*. 2007. 23(21): 2947-2948.
Lieberman J, Skolnik PR, Parkerson GR 3rd, Fabry JA, Landry B, Bethel J, Kagan J. Safety of autologous, ex vivo-expanded human immunodeficiency virus (HIV)-specific cytotoxic T-lymphocyte infusion in HIV- infected patients. *Blood*. Sep. 15, 1997. 90(6):2196-206.
Needleman and Wunsch, J., A General Method Applicable to the Search for Similarities in the Amino Acid Sequence of Two Proteins, *Journal of Molecular Biology*. 1970. 48:443.
Neville M, Stutz F, Lee L, Davis LI, Rosbash M. The importin-beta family member Crm1p bridges the interaction between Rev and the nuclear pore complex during nuclear export. *Current Biology*. Oct. 1, 1997. 7(10):767-775. PMID: 9368759.
Notredame et al., T-Coffee: A novel method for multiple sequence alignments. *Journal of Molecular Biology*. 2000. 302: 205-217.
Ory DS, Neugeboren BA, Mulligan RC. A stable human-derived packaging cell line for production of high titer retrovirus/vesicular stomatitis virus G pseudotypes. 1996.
Pearson and Lipman. *Proceedings of the National Academy of Sciences of the United States of America*. 1988. 85:2444-2448.
Pollard and Malim, The HIV-1 Rev protein. *Annual Review of Microbiology*. 1998. 52:491-532.
Smith and Waterman, Comparison of Biosequences, *Advances in Applied Mathematics*. 1981. 2:482.
Tebas P, Stein D, Tang WW, Frank I, Wang SQ, Lee G, Spratt SK, Surosky RT, Giedlin MA, Nichol G, Holmes MC, Gregory PD, Ando DG, Kalos M, Collman RG, Binder-Scholl G, Plesa G, Hwang WT, Levine BL, June CH. Gene editing of CCR5 in autologous CD4 T cells of persons infected with HIV. *New England Journal of Medicine*. Mar. 6, 2014. 370(10):901-10.
Thompson J. D., Higgins D. G., Gibson T. J. Clustal W: improving the sensitivity of progressive multiple sequence alignment through sequence weighting, position-specific gap penalties and weight matrix choice. *Nucleic Acids Research*. 1994. 22:4673-4680.
Trickett AE, Kwan YL, Cameron B, Dwyer JM. Ex vivo expansion of functional T lymphocytes from HIV- infected individuals. *Journal of Immunological Methods*. Apr. 1, 2002. 262(1-2):71-83.
Van Lunzen J, Glaunsinger T, Stahmer I, Von Baehr V, Baum C, Schilz A, Kuehlcke K, Naundorf S, Martinius H, Hermann F, Giroglou T, Newrzela S, Müller I, Brauer F, Brandenburg G, Alexandrov A, Von Laer D. Transfer of autologous gene-modified T cells in HIV- infected patients with advanced immunodeficiency and drug-resistant virus. *Molecular Therapy*. May 15, 2007. 15(5):1024-33.
Von Laer, D, Hasselmann, S and Hasselmann, K. Gene therapy for HIV infection: what does it need to make it work? *Journal of Gene Medicine*. 2006. 8: 658-667.
Wei P, Garber ME, Fang SM, Fischer WH, Jones KA. A novel CDK9-associated C-type cyclin interacts directly with HIV-1 Tat and mediates its high-affinity, loop-specific binding to TAR RNA. *Cell*. Feb. 20, 1998. 92(4):451-462. PMID: 9491887.
Ferrari et al., Hardwood et al (EDS.). Genetics. *Bacillus*. Plenum Publishing Corp. 1989. pp. 57-72 (Book).
Nekhai S, Jeang K-T. Transcriptional and post-transcriptional regulation of HIV-1 gene expression: role of cellular factors for Tat and Rev. *Future Microbiology*. Dec. 2006. 1(4):417-426. PMID: 17661632.
Bieniasz PD, Grdina TA, Bogerd HP, Cullen BR. Analysis of the effect of natural sequence variation in Tat and in cyclin T on the formation and RNA binding properties of Tat-cyclin T complexes. J Virol. Jul. 1999;73(7):5777-5786. PMCID: PMC112638.
Cho W-K, Jang MK, Huang K, Pise-Masison CA, Brady JN. Human T-lymphotropic virus type 1 Tax protein complexes with P-TEFb and competes for Brd4 and 7SK snRNP/HEXIM1 binding. J Virol. Dec. 2010;84(24):12801-12809. PMCID: PMC3004308.

Elinav H, Wu Y, Coskun A, Hryckiewicz K, Kemler I, Hu Y, Rogers H, Hao B, Ben Mamoun C, Poeschla E, Sutton R. Human CRM1 augments production of infectious human and feline immunodeficiency viruses from murine cells. J Virol. Nov. 2012;86(22):12053-12068. PMCID: PMC3486471.
Feng Y, Broder CC, Kennedy PE, Berger EA. HIV-1 entry cofactor: functional cDNA cloning of a seven-transmembrane, G protein-coupled receptor. Science. May 10, 1996;272(5263):872-877.
Landau NR, Warton M, Littman DR. The envelope glycoprotein of the human immunodeficiency virus binds to the immunoglobulin-like domain of CD4. Nature. Jul. 14, 1988;334(6178):159-162.
Levine, BL, Humeau, LM, Boyer J, Macgregor, RR, Rebello, T, Lu, X et al. (2006) Gene transfer in humans using a conditionally replicating lentiviral vector. Proc Natl Acad Sci USA 103: 17372-17377.
Mariani R, Chen D, Schröfelbauer B, Navarro F, König R, Bollman B, Münk C, Nymark-McMahon H, Landau NR. Species-specific exclusion of APOBEC3G from HIV-1 virions by Vif. Cell. Jul. 11, 2003;114(1):21-31. PMID: 12859895.
McNatt MW, Zang T, Hatziioannou T, Bartlett M, Fofana IB, Johnson WE, Neil SJD, Bieniasz PD. Species-specific activity of HIV-1 Vpu and positive selection of tetherin transmembrane domain variants. PLoS Pathog. Feb. 2009;5(2):e1000300. PMCID: PMC2633611.
Nagai-Fukataki M, Ohashi T, Hashimoto I, Kimura T, Hakata Y, Shida H. Nuclear and cytoplasmic effects of human CRM1 on HIV-1 production in rat cells. Genes Cells Devoted Mol Cell Mech. Feb. 2011;16(2):203-216. PMID: 21251165.
Sawyer SL, Wu LI, Emerman M, Malik HS. Positive selection of primate TRIM5alpha identifies a critical species-specific retroviral restriction domain. Proc Natl Acad Sci U S A. Feb. 22, 2005;102(8):2832-2837. PMCID: PMC549489.
Schröfelbauer B, Chen D, Landau NR. A single amino acid of APOBEC3G Controls its species-specific interaction with virion infectivity factor (Vif). Proc Natl Acad Sci U S A. Mar. 16, 2004;101(11):3927-3932. PMCID: PMC374346.
Sherer NM, Swanson CM, Hué S, Roberts RG, Bergeron JRC, Malim MH. Evolution of a species-specific determinant within human CRM1 that regulates the post-transcriptional phases of HIV-1 replication. PLoS Pathog. Nov. 2011;7(11):e1002395. PMCID: PMC3219727.
Sievers F, Wilm A, Dineen D, Gibson TJ, Karplus K, Li W, Lopez R, McWilliam H, Remmert M, Söding J, Thompson JD, Higgins DG. Fast, scalable generation of high-quality protein multiple sequence alignments using Clustal Omega. Mol Syst Biol. Oct. 11, 2011;7:539.
Stremlau M, Owens CM, Perron MJ, Kiessling M, Autissier P, Sodroski J. The cytoplasmic body component TRIM5alpha restricts HIV-1 infection in Old World monkeys. Nature. Feb. 26, 2004;427(6977):848-853.
Tada T, Kadoki M, Liu Y, Tokunaga K, Iwakura Y. Transgenic expression of the human LEDGF/p75 gene relieves the species barrier against HIV-1 infection in mouse cells. Front Microbiol. 2013;4:377. PMCID: PMC3865800.
Zheng Y-H, Yu H-F, Peterlin BM. Human p32 protein relieves a post-transcriptional block to HIV replication in murine cells. Nat Cell Biol. Jul. 2003;5(7):611-618.
Zhou M, Lu H, Park H, Wilson-Chiru J, Linton R, Brady JN. Tax interacts with P-TEFb in a novel manner to stimulate human T-lymphotropic virus type 1 transcription. J Virol. May 2006;80(10):4781-4791. PMCID: PMC1472077.
Bieniasz, Paul D., and Cullen, Bryan R. "Multiple Blocks to Human Immunodeficiency Virus Type 1 Replication in Rodent Cells," Journal of Virology, vol. 74, No. 21, (2000) p. 9869-9877.
Keppler, Oliver T., et al. "Susceptibility of Rat-Derived Cells to Replication by Human Immunodeficiency Virus Type 1," Journal of Virology, vol. 75, No. 17 (2001) p. 8063-8073.
Kwak, Youn Tae, et al. "Role of the Human and Murine Cyclin T Proteins in Regulating HIV-1 *tat*-Activation," J. Mol. Biol. (1999) 288, p. 57-69.
Luznik, Leo, et al. "*Tat*-independent Replication of Human Immunodeficiency Viruses," The Journal of Clinical Investigation, Inc., vol. 95 (1995) p. 328-332.

(56) References Cited

OTHER PUBLICATIONS

Shida, Hisatoshi, et al. "HIV-1 susceptibility of transgenic rat-derived primary macrophage/T cells and a T cell line that express human receptors, CyclinT1 and CRM1 genes," Genes to Cells (2017) 22, p. 424-435.

* cited by examiner

```
CLUSTAL O(1.2.4) multiple sequence alignment hCCNT1*      MEGERKNNNKRWYFTREQLENSPSRRFGVDPDKELSYRQQAANLLQDMGQRLNVSQLTIN 60
hCCNT1       MEGERKNNNKRWYFTREQLENSPSRRFGVDPDKELSYRQQAANLLQDMGQRLNVSQLTIN 60
mCCNT1       MEGERKNNNKRWYFTREQLENSPSRRFGVDSDKELSYRQQAANLLQDMGQRLNVSQLTIN 60
             ****************************:*************************** hCCNT1*      TAIVYMHRFYMIQSFTQFPGNSVAPAALFLAAKVEEQPKKLEHVIKVAHTCLHPQESLPD 120
hCCNT1       TAIVYMHRFYMIQSFTQFPGNSVAPAALFLAAKVEEQPKKLEHVIKVAHTCLHPQESLPD 120
mCCNT1       TAIVYMHRFYMIQSFTQFHRYSMAPAALFLAAKVEEQPKKLEHVIKVAHTCLHPQESLPD 120
             ******************  *:************************************** hCCNT1*      TRSEAYLQQVQDLVILESIILQTLGFELTIDHPHTHVVKCTQLVRASKDLAQTSYFMATN 180
hCCNT1       TRSEAYLQQVQDLVILESIILQTLGFELTIDHPHTHVVKCTQLVRASKDLAQTSYFMATN 180
mCCNT1       TRSEAYLQQVQDLVILESIILQTLGFELTIDHPHTHVVKCTQLVRASKDLAQTSYFMATN 180
             ************************************************************ hCCNT1*      SLHLTTFSLQYTPPVVACVCIHLACKWSNWEIPVSTDGKHWWEYVDATVTLELLDELTHE 240
hCCNT1       SLHLTTFSLQYTPPVVACVCIHLACKWSNWEIPVSTDGKHWWEYVDATVTLELLDELTHE 240
mCCNT1       SLHLTTFSLQYTPPVVACVCIHLACKWSNWEIPVSTDGKHWWEYVDATVTLELLDELTHE 240
             ************************************************************ hCCNT1*      FLQILEKTPNRLKRIWNWRAYEAAKKTKADDRGTDEKTSEQTILNMISQSSSDTTIAGLM 300
hCCNT1       FLQILEKTPNRLKRIWNWRACEAAKKTKADDRGTDEKTSEQTILNMISQSSSDTTIAGLM 300
mCCNT1       FLQILEKTPSRLKRIRNWRAYQAAMKTKPDDRGADENTSEQTILNMISQTSSDTTIAGLM 300
             *******.*   : * * :********:******** hCCNT1*      SMSTSTTSAVPSLPVSEESSSNLTSVEMLPGKRWLSSQPSFKLEPTQGHRTSENLALTGV 360
hCCNT1       SMSTSTTSAVPSLPVSEESSSNLTSVEMLPGKRWLSSQPSFKLEPTQGHRTSENLALTGV 360
mCCNT1       SMSTASTSAVPSLPSSEESSSSLTSVDMLQGERWLSSQPPFKLEAAQGHRTSESLALIGV 360
             ****::*******  ****** ****:** *:*******.****   *******.***:**

hCCNT1*      DHSLPQDGSNAFISQKQNSKSVPSAKVSLKEYRAKHAEELAAQKRQLENMEANVKSQYAY 420
hCCNT1       DHSLPQDGSNAFISQKQNSKSVPSAKVSLKEYRAKHAEELAAQKRQLENMEANVKSQYAY 420
mCCNT1       DHSLQQDGSSAFGSQKQASKSVPSAKVSLKEYRAKHAEELAAQKRQLENMEANVKSQYAY 420
             **  . ** *************************************** hCCNT1*      AAQNLLSHHDSHSSVILKMPIEGSENPERPFLEKADKTALKMRIPVAGGDKAASSKPEEI 480
hCCNT1       AAQNLLSHHDSHSSVILKMPIEGSENPERPFLEKADKTALKMRIPVAGGDKAASSKPEEI 480
mCCNT1       AAQNLLS-HDSHSSVILKMPIESSENPERPFLDKADKSALKMRLPVASGDKAVSSKPEEI 479
             ***** **********.****::*:*.**.***** hCCNT1*      KMRIKVHAAADKHNSVEDSVTKSREHKEKHKTHPSNHHHHHNHHSHKHSHSQLPVGTGNK 540
hCCNT1       KMRIKVHAAADKHNSVEDSVTKSREHKEKHKTHPSNHHHHHNHHSHKHSHSQLPVGTGNK 540
mCCNT1       KMRIKVHSAGDKHNSIEDSVTKSREHKEKQRTHPSNHHHHHNHHSHRHSHLQLPAGPVSK 539
             *******:*.***:******** :***********:*   ***.* * hCCNT1*      RPGDPKHSSQTSNLAHKTYSLSSSFSSSSSTRKRGPSEETGGAVFDHPAKIAKSTKSSSL 600
hCCNT1       RPGDPKHSSQTSNLAHKTYSLSSSFSSSSSTRKRGPSEETGGAVFDHPAKIAKSTKSSSL 600
mCCNT1       RPSDPKHSSQTSTLAHKTYSLSSTLSSSSSTRKRGPPEETGAAVFDHPAKIAKSTK-SSL 598
             **.*********.**********  **********.****.**************** ***
```

FIG. 1A

```
hCCNT1*    NFSFPSLPTMGQMPGHSSDTSGLSFSQPSCKTRVPHSKLDKGPTGANGHNTTQTIDYQDT 660
hCCNT1     NFSFPSLPTMGQMPGHSSDTSGLSFSQPSCKTRVPHSKLDKGPTGANGHNTTQTIDYQDT 660
mCCNT1     NFPFPPLPTMTQLPGHSSDTSGLPFSQPSCKTRVPHMKLDKGPPGANGHNATQSIDYQDT 658
             ****  *:******** ******** ** **::****** hCCNT1*    VNMLHSLLSAQGVQPTQPTAFEFVRPYSDYLNPRSGGISSRSGNTDKPRPPPLPSEPPPP 720
hCCNT1     VNMLHSLLSAQGVQPTQPTAFEFVRPYSDYLNPRSGGISSRSGNTDKPRPPPLPSEPPPP 720
mCCNT1     VNMLHSLLSAQGVQPTQAPAFEFVHSYGEYMNPRAGAISSRSGTTDKPRPPPLPSEPPPP 718
           ***************  ***: *.:*:***:*.**** .************* hCCNT1*    LPPLPK 726 (SEQ ID NO:1)
hCCNT1     LPPLPK 726 (SEQ ID NO:3)
mCCNT1     LPPLPK 724 (SEQ ID NO:6)
           ******
```

FIG. 1B

```
CLUSTAL O(1.2.4) multiple sequence alignment hXPO1*      MPAIMTMLADHAARQLLDFSQKLDINLLDNVVNCLYHGEGAQQRMAQEVLTHLKEHPDAW   60
hXPO1       MPAIMTMLADHAARQLLDFSQKLDINLLDNVVNCLYHGEGAQQRMAQEVLTHLKEHPDAW   60
mXPO1       MPAIMTMLADHAARQLLDFSQKLDINLLDNVVNCLYHGEGAQQRMAQEVLTHLKEHPDAW   60
            ************************************************************ hXPO1*      TRVDTILEFSQNMNTKYYGLQILENVIKTRWKILPRNQCEGIKKYVVGLIIKTSSDPTCV  120
hXPO1       TRVDTILEFSQNMNTKYYGLQILENVIKTRWKILPRNQCEGIKKYVVGLIIKTSSDPTCV  120
mXPO1       TRVDTILEFSQNMNTKYYGLQILENVIKTRWKILPRNQCEGIKKYVVGLIIKTSSDPTCV  120
            ************************************************************ hXPO1*      EKEKVYIGKLNMILVQILKQEWPKHWPTFISDIVGASRTSESLCQNNMVILKLLSEEVFD  180
hXPO1       EKEKVYIGKLNMILVQILKQEWPKHWPTFISDIVGASRTSESLCQNNMVILKLLSEEVFD  180
mXPO1       EKEKVYIGKLNMILVQILKQEWPKHWPTFISDIVGASRTSESLCQNNMVILKLLSEEVFD  180
            ************************************************************ hXPO1*      FSSGQITQVKSKHLKDSMCNEFSQIFQLCQFVMENSQNAPLVHATLETLLRFLNWIPLGY  240
hXPO1       FSSGQITQVKSKHLKDSMCNEFSQIFQLCQFVMENSQNAPLVHATLETLLRFLNWIPLGY  240
mXPO1       FSSGQITQVKAKHLKDSMCNEFSQIFQLCQFVMENSQNAPLVHATLETLLRFLNWIPLGY  240
            ********:*********************************************** hXPO1*      IFETKLISTLIYKFLNVPMFRNVSLKCLTEIAGVSVSQYEEQFVTLFTLTMMQLKQMLPL  300
hXPO1       IFETKLISTLIYKFLNVPMFRNVSLKCLTEIAGVSVSQYEEQFVTLFTLTMMQLKQMLPL  300
mXPO1       IFETKLISTLIYKFLNVPMFRNVSLKCLTEIAGVSVSQYEEQFETLFTLTMMQLKQMLPL  300
            ****************************************.************** hXPO1*      NTNIRLAYSNGKDDEQNFIQNLSLFLCTFLKEHDQLIEKRLNLRETLMEALHYMLLVSEV  360
hXPO1       NTNIRLAYSNGKDDEQNFIQNLSLFLCTFLKEHDQLIEKRLNLRETLMEALHYMLLVSEV  360
mXPO1       NTNIRLAYSNGKDDEQNFIQNLSLFLCTFLKEHGQLLEKRLNLREALMEALHYMLLVSEV  360
            *******************************.:*****:************ hXPO1*      EETEIFKICLEYWNHLAAELYRESPFSTSASPLLSGSQHFDVPPRRQLYLTVLSKVRLLM  420
hXPO1       EETEIFKICLEYWNHLAAELYRESPFSTSASPLLSGSQHFDVPPRRQLYLPMLFKVRLLM  420
mXPO1       EETEIFKICLEYWNHLAAELYRESPFSTSASPLLSGSQHFDIPPRRQLYLTVLSKVRLLM  420
            ***************************************:******  :*  ****** hXPO1*      VSRMAKPEEVLVVENDQGEVVREFMKDTDSINLYKNMRETLVYLTHLDYVDTERIMTEKL  480
hXPO1       VSRMAKPEEVLVVENDQGEVVREFMKDTDSINLYKNMRETLVYLTHLDYVDTERIMTEKL  480
mXPO1       VSRMAKPEEVLVVENDQGEVVREFMKDTDSINLYKNMRETLVYLTHLDYVDTEIIMTKKL  480
            ****************************************************  ***:**

hXPO1*      HNQVNGTEWSWKNLNTLCWAIGSISGAMHEEDEKRFLVTVIKDLLGLCEQKRGKDNKAII  540
hXPO1       HNQVNGTEWSWKNLNTLCWAIGSISGAMHEEDEKRFLVTVIKDLLGLCEQKRGKDNKAII  540
mXPO1       QNQVNGTEWSWKNLNTLCWAIGSISGAMHEEDEKRFLVTVIKDLLGLCEQKRGKDNKAII  540
            :*********************************************************** hXPO1*      ASNIMYIVGQYPRFLRAHWKFLKTVVNKLFEFMHETHDGVQDMACDTFIKIAQKCRRHFV  600
hXPO1       ASNIMYIVGQYPRFLRAHWKFLKTVVNKLFEFMHETHDGVQDMACDTFIKIAQKCRRHFV  600
mXPO1       ASNIMYIVGQYPRFLRAHWKFLKTVVNKLFEFMHETHDGVQDMACDTFIKIAQKCRRHFV  600
            ************************************************************
```

FIG. 2A

```
hXPO1*  QVQVGEVMPFIDEILNNINTIICDLQPQQVHTFYEAVGYMIGAQTDQTVQEHLIEKYMLL  660
hXPO1   QVQVGEVMPFIDEILNNINTIICDLQPQQVHTFYEAVGYMIGAQTDQTVQEHLIEKYMLL  660
mXPO1   QVQVGEVMPFIDEILNNINTIICDLQPQQVHTFYEAVGYMIGAQTDQTVQEHLIEKYMLL  660
        ************************************************************ hXPO1*  PNQVWDSIIQQATKNVDILKDPETVKQLGSILKTNVRACKAVGHPFVIQLGRIYLDMLNV  720
hXPO1   PNQVWDSIIQQATKNVDILKDPETVKQLGSILKTNVRACKAVGHPFVIQLGRIYLDMLNV  720
mXPO1   PNQVWDSIIQQATKNVDILKDPETVKQLGSILKTNVRACKAVGHPFVIQLGRIYLDMLNV  720
        ************************************************************ hXPO1*  YKCLSENISAAIQANGEMVTKQPLIRSMRTVKRETLKLISGWVSRSNDPQMVAENFVPPL  780
hXPO1   YKCLSENISAAIQANGEMVTKQPLIRSMRTVKRETLKLISGWVSRSNDPQMVAENFVPPL  780
mXPO1   YKCLSENISAAIQANGEMVTKQPLIRSMRTVKRETLKLISGWVSRSNDPQMVAENFVPPL  780
        ************************************************************ hXPO1*  LDAVLIDYQRNVPAAREPEVLSTMAIIVNKLGGHITAEIPQIFDAVFECTLNMINKDFEE  840
hXPO1   LDAVLIDYQRNVPAAREPEVLSTMAIIVNKLGGHITAEIPQIFDAVFECTLNMINKDFEE  840
mXPO1   LDAVLIDYQRNVPAAREPEVLSTMAIIVNKLGGHITAEIPQIFDAVFECTLNMINKDFEE  840
        ************************************************************ hXPO1*  YPEHRTNFFLLLQAVNSHCFPAFLAIPPTQFKLVLDSIIWAFKHTMRNVADTGLQILFTL  900
hXPO1   YPEHRTNFFLLLQAVNSHCFPAFLAIPPTQFKLVLDSIIWAFKHTMRNVADTGLQILFTL  900
mXPO1   YPEHRTNFFLLLQAVNSHCFPAFLAIPPAQFKLVLDSIIWAFKHTMRNVADTGLQILFTL  900
        **************************:***************************** hXPO1*  LQNVAQEEAAAQSFYQTYFCDILQHIFSVVTDTSHTAGLTMHASILAYMFNLVEEGKIST  960
hXPO1   LQNVAQEEAAAQSFYQTYFCDILQHIFSVVTDTSHTAGLTMHASILAYMFNLVEEGKIST  960
mXPO1   LQNVAQEEAAAQSFYQTYFCDILQHIFSVVTDTSHTAGLTMHASILAYMFNLVEEGKIST  960
        ************************************************************ hXPO1*  SLNPGNPVNNQIFLQEYVANLLKSAFPHLQDAQVKLFVTGLFSLNQDIPAFKEHLRDFLV  1020
hXPO1   SLNPGNPVNNQIFLQEYVANLLKSAFPHLQDAQVKLFVTGLFSLNQDIPAFKEHLRDFLV  1020
mXPO1   PLNPGNPVNNQMFIQDYVANLLKSAFPHLQDAQVKLFVTGLFSLNQDIPAFKEHLRDFLV  1020
        **********::*:*:******************************************** hXPO1*  QIKEFAGEDTSDLFLEEREIALRQADEEKHKRQMSVPGIFNPHEIPEEMCD  1071  (SEQ ID
hXPO1   QIKEFAGEDTSDLFLEEREIALRQADEEKHKRQMSVPGIFNPHEIPEEMCD  1071  (SEQ ID
mXPO1   QIKEFAGEDTSDLFLEERETALRQAQEEKHKLQMSVPGILNPHEIPEEMCD  1071  (SEQ ID
        *****************::**:**:********** hXPO1*  NO:7)
hXPO1   NO:9)
mXPO1   NO:12)
```

FIG. 2B

```
                        SEQUENCE LISTING

<160> NUMBER OF SEQ ID NOS: 19

<210> SEQ ID NO 1
<211> LENGTH: 726
<212> TYPE: PRT
<213> ORGANISM: Artificial Sequence
<220> FEATURE:
<223> OTHER INFORMATION: C261Y mutant of human CCNT1

<400> SEQUENCE: 1

Met Glu Gly Glu Arg Lys Asn Asn Lys Arg Trp Tyr Phe Thr Arg
1               5                   10                  15

Glu Gln Leu Glu Asn Ser Pro Ser Arg Arg Phe Gly Val Asp Pro Asp
                20                  25                  30

Lys Glu Leu Ser Tyr Arg Gln Gln Ala Ala Asn Leu Leu Gln Asp Met
                35                  40                  45

Gly Gln Arg Leu Asn Val Ser Gln Leu Thr Ile Asn Thr Ala Ile Val
        50                  55                  60

Tyr Met His Arg Phe Tyr Met Ile Gln Ser Phe Thr Gln Phe Pro Gly
65                  70                  75                  80

Asn Ser Val Ala Pro Ala Ala Leu Phe Leu Ala Ala Lys Val Glu Glu
                85                  90                  95

Gln Pro Lys Lys Leu Glu His Val Ile Lys Val Ala His Thr Cys Leu
                100                 105                 110

His Pro Gln Glu Ser Leu Pro Asp Thr Arg Ser Glu Ala Tyr Leu Gln
                115                 120                 125

Gln Val Gln Asp Leu Val Ile Leu Glu Ser Ile Ile Leu Gln Thr Leu
        130                 135                 140

Gly Phe Glu Leu Thr Ile Asp His Pro His Thr His Val Val Lys Cys
145                 150                 155                 160

Thr Gln Leu Val Arg Ala Ser Lys Asp Leu Ala Gln Thr Ser Tyr Phe
                165                 170                 175

Met Ala Thr Asn Ser Leu His Leu Thr Thr Phe Ser Leu Gln Tyr Thr
                180                 185                 190

Pro Pro Val Val Ala Cys Val Cys Ile His Leu Ala Cys Lys Trp Ser
                195                 200                 205

Asn Trp Glu Ile Pro Val Ser Thr Asp Gly Lys His Trp Trp Glu Tyr
        210                 215                 220

Val Asp Ala Thr Val Thr Leu Glu Leu Leu Asp Glu Leu Thr His Glu
225                 230                 235                 240

Phe Leu Gln Ile Leu Glu Lys Thr Pro Asn Arg Leu Lys Arg Ile Trp
                245                 250                 255

Asn Trp Arg Ala Tyr Glu Ala Ala Lys Lys Thr Lys Ala Asp Asp Arg
                260                 265                 270

Gly Thr Asp Glu Lys Thr Ser Glu Gln Thr Ile Leu Asn Met Ile Ser
        275                 280                 285

Gln Ser Ser Ser Asp Thr Thr Ile Ala Gly Leu Met Ser Met Ser Thr
        290                 295                 300
```

```
Ser Thr Thr Ser Ala Val Pro Ser Leu Pro Val Ser Glu Ser Ser
305                 310                 315                 320

Ser Asn Leu Thr Ser Val Glu Met Leu Pro Gly Lys Arg Trp Leu Ser
            325                 330                 335

Ser Gln Pro Ser Phe Lys Leu Glu Pro Thr Gln Gly His Arg Thr Ser
        340                 345                 350

Glu Asn Leu Ala Leu Thr Gly Val Asp His Ser Leu Pro Gln Asp Gly
            355                 360                 365

Ser Asn Ala Phe Ile Ser Gln Lys Gln Asn Ser Lys Ser Val Pro Ser
370                 375                 380

Ala Lys Val Ser Leu Lys Glu Tyr Arg Ala Lys His Ala Glu Glu Leu
385                 390                 395                 400

Ala Ala Gln Lys Arg Gln Leu Glu Asn Met Glu Ala Asn Val Lys Ser
                405                 410                 415

Gln Tyr Ala Tyr Ala Ala Gln Asn Leu Leu Ser His His Asp Ser His
                420                 425                 430

Ser Ser Val Ile Leu Lys Met Pro Ile Glu Gly Ser Glu Asn Pro Glu
            435                 440                 445

Arg Pro Phe Leu Glu Lys Ala Asp Lys Thr Ala Leu Lys Met Arg Ile
450                 455                 460

Pro Val Ala Gly Gly Asp Lys Ala Ala Ser Ser Lys Pro Glu Glu Ile
465                 470                 475                 480

Lys Met Arg Ile Lys Val His Ala Ala Ala Asp Lys His Asn Ser Val
                485                 490                 495

Glu Asp Ser Val Thr Lys Ser Arg Glu His Lys Glu Lys His Lys Thr
            500                 505                 510

His Pro Ser Asn His His His His Asn His His Ser His Lys His
            515                 520                 525

Ser His Ser Gln Leu Pro Val Gly Thr Gly Asn Lys Arg Pro Gly Asp
530                 535                 540

Pro Lys His Ser Ser Gln Thr Ser Asn Leu Ala His Lys Thr Tyr Ser
545                 550                 555                 560

Leu Ser Ser Ser Phe Ser Ser Ser Ser Thr Arg Lys Arg Gly Pro
                565                 570                 575

Ser Glu Glu Thr Gly Gly Ala Val Phe Asp His Pro Ala Lys Ile Ala
            580                 585                 590

Lys Ser Thr Lys Ser Ser Ser Leu Asn Phe Ser Phe Pro Ser Leu Pro
            595                 600                 605

Thr Met Gly Gln Met Pro Gly His Ser Ser Asp Thr Ser Gly Leu Ser
            610                 615                 620

Phe Ser Gln Pro Ser Cys Lys Thr Arg Val Pro His Ser Lys Leu Asp
625                 630                 635                 640

Lys Gly Pro Thr Gly Ala Asn Gly His Asn Thr Thr Gln Thr Ile Asp
                645                 650                 655

Tyr Gln Asp Thr Val Asn Met Leu His Ser Leu Leu Ser Ala Gln Gly
                660                 665                 670

Val Gln Pro Thr Gln Pro Thr Ala Phe Glu Phe Val Arg Pro Tyr Ser
            675                 680                 685

Asp Tyr Leu Asn Pro Arg Ser Gly Gly Ile Ser Ser Arg Ser Gly Asn
            690                 695                 700

Thr Asp Lys Pro Arg Pro Pro Leu Pro Ser Glu Pro Pro Pro
705                 710                 715                 720
```

Leu Pro Pro Leu Pro Lys
           725

<210> SEQ ID NO 2
<211> LENGTH: 2181
<212> TYPE: DNA
<213> ORGANISM: Artificial Sequence
<220> FEATURE:
<223> OTHER INFORMATION: C261Y mutant of human CCNT1

<400> SEQUENCE: 2

| | | |
|---|---|---|
| atggagggag agaggaagaa caacaacaaa cggtggtatt tcactcgaga acagctggaa | 60 |
| aatagcccat cccgtcgttt tggcgtggac ccagataaag aactttctta tcgccagcag | 120 |
| gcggccaatc tgcttcagga catggggcag cgtcttaacg tctcacaatt gactatcaac | 180 |
| actgctatag tatacatgca tcgattctac atgattcagt ccttcacaca gttccctgga | 240 |
| aattctgtgg ctccagcagc cttgtttcta gcagctaaag tggaggagca gcccaaaaaa | 300 |
| ttggaacatg tcatcaaggt agcacatact tgtctccatc ctcaggaatc ccttcctgat | 360 |
| actagaagtg aggcttattt gcaacaagtt caagatctgg tcattttaga aagcataatt | 420 |
| ttgcagactt aggctttga actaacaatt gatcacccac atactcatgt agtaaagtgc | 480 |
| actcaacttg ttcgagcaag caaggactta gcacagactt cttacttcat ggcaaccaac | 540 |
| agcctgcatt tgaccacatt tagcctgcag tacacacctc ctgtggtggc ctgtgtctgc | 600 |
| attcacctgg cttgcaagtg gtccaattgg gagatcccag tctcaactga cgggaagcac | 660 |
| tggtgggagt atgttgacgc cactgtgacc ttggaacttt tagatgaact gacacatgag | 720 |
| tttctacaga ttttggagaa actcccaac aggctcaaac gcatttggaa ttggagggcg | 780 |
| tacgaagctg ccaagaaaac aaaagcagat gaccgaggaa cagatgaaaa gacttcagag | 840 |
| cagacaatcc tcaatatgat ttcccagagc tcttcagaca caaccattgc aggtttaatg | 900 |
| agcatgtcaa cttctaccac aagtgcagtg ccttccctgc cagtctccga gagtcatcc | 960 |
| agcaacttaa ccagtgtgga gatgttgccg ggcaagcgtt ggctgtcctc ccaaccttct | 1020 |
| ttcaaactag aacctactca gggtcatcgg actagtgaga atttagcact tacaggagtt | 1080 |
| gatcattcct taccacagga tggttcaaat gcatttattt cccagaagca gaatagtaag | 1140 |
| agtgtgccat cagctaaagt gtcactgaaa gaataccgcg cgaagcatgc agaagaattg | 1200 |
| gctgcccaga gaggcaact ggagaacatg gaagccaatg tgaagtcaca atatgcatat | 1260 |
| gctgcccaga atctcctttc tcatcatgat agccattctt cagtcattct aaaaatgccc | 1320 |
| atagagggtt cagaaaaccc cgagcggcct tttctggaaa aggctgacaa acagctctc | 1380 |
| aaaatgagaa tcccagtggc aggtggagat aaagctgcgt cttcaaaacc agaggagata | 1440 |
| aaaatgcgca taaagtcca tgctgcagct gataagcaca attctgtaga ggacagtgtt | 1500 |
| acaaagagcc gagagcacaa agaaaagcac aagactcacc catctaatca tcatcatcat | 1560 |
| cataatcacc actcacacaa gcactctcat tcccaacttc cagttggtac tgggaacaaa | 1620 |
| cgtcctggtg atccaaaaca tagtagccag acaagcaact tagcacataa aacctatagc | 1680 |
| ttgtctagtt cttttttcctc ttccagttct actcgtaaaa ggggaccctc tgaagagact | 1740 |
| ggaggggctg tgtttgatca tccagccaag attgccaaga gtactaaatc ctcttcccta | 1800 |
| aatttctcct tcccttcact tcctacaatg gtcagatgc tgggcatag tcagacaca | 1860 |
| agtggccttt ccttttcaca gcccagctgt aaaactcgtg tccctcattc gaaactggat | 1920 |
| aaagggccca ctggggccaa tggtcacaac acgacccaga caatagacta tcaagacact | 1980 |

-continued

```
gtgaatatgc ttcactccct gctcagtgcc cagggtgttc agcccactca gcctactgca      2040
tttgaatttg ttcgtcctta tagtgactat ctgaatcctc ggtctggtgg aatctcctcg      2100
agatctggca atacagacaa accccggcca ccacctctgc catcagaacc tcctccacca      2160
cttccacccc ttcctaagta a                                                2181
```

<210> SEQ ID NO 3
<211> LENGTH: 726
<212> TYPE: PRT
<213> ORGANISM: Homo sapiens

<400> SEQUENCE: 3

```
Met Glu Gly Glu Arg Lys Asn Asn Lys Arg Trp Tyr Phe Thr Arg
1               5                   10                  15

Glu Gln Leu Glu Asn Ser Pro Ser Arg Arg Phe Gly Val Asp Pro Asp
                20                  25                  30

Lys Glu Leu Ser Tyr Arg Gln Gln Ala Ala Asn Leu Leu Gln Asp Met
            35                  40                  45

Gly Gln Arg Leu Asn Val Ser Gln Leu Thr Ile Asn Thr Ala Ile Val
    50                  55                  60

Tyr Met His Arg Phe Tyr Met Ile Gln Ser Phe Thr Gln Phe Pro Gly
65                  70                  75                  80

Asn Ser Val Ala Pro Ala Ala Leu Phe Leu Ala Ala Lys Val Glu Glu
                85                  90                  95

Gln Pro Lys Lys Leu Glu His Val Ile Lys Val Ala His Thr Cys Leu
            100                 105                 110

His Pro Gln Glu Ser Leu Pro Asp Thr Arg Ser Glu Ala Tyr Leu Gln
        115                 120                 125

Gln Val Gln Asp Leu Val Ile Leu Glu Ser Ile Ile Leu Gln Thr Leu
    130                 135                 140

Gly Phe Glu Leu Thr Ile Asp His Pro His Thr His Val Val Lys Cys
145                 150                 155                 160

Thr Gln Leu Val Arg Ala Ser Lys Asp Leu Ala Gln Thr Ser Tyr Phe
                165                 170                 175

Met Ala Thr Asn Ser Leu His Leu Thr Thr Phe Ser Leu Gln Tyr Thr
            180                 185                 190

Pro Pro Val Val Ala Cys Val Cys Ile His Leu Ala Cys Lys Trp Ser
        195                 200                 205

Asn Trp Glu Ile Pro Val Ser Thr Asp Gly Lys His Trp Trp Glu Tyr
    210                 215                 220

Val Asp Ala Thr Val Thr Leu Glu Leu Leu Asp Glu Leu Thr His Glu
225                 230                 235                 240

Phe Leu Gln Ile Leu Glu Lys Thr Pro Asn Arg Leu Lys Arg Ile Trp
                245                 250                 255

Asn Trp Arg Ala Cys Glu Ala Ala Lys Lys Thr Lys Ala Asp Asp Arg
            260                 265                 270

Gly Thr Asp Glu Lys Thr Ser Glu Gln Thr Ile Leu Asn Met Ile Ser
        275                 280                 285

Gln Ser Ser Ser Asp Thr Thr Ile Ala Gly Leu Met Ser Met Ser Thr
    290                 295                 300

Ser Thr Thr Ser Ala Val Pro Ser Leu Pro Val Ser Glu Glu Ser Ser
305                 310                 315                 320

Ser Asn Leu Thr Ser Val Glu Met Leu Pro Gly Lys Arg Trp Leu Ser
                325                 330                 335
```

Ser Gln Pro Ser Phe Lys Leu Glu Pro Thr Gln Gly His Arg Thr Ser
              340                 345                 350

Glu Asn Leu Ala Leu Thr Gly Val Asp His Ser Leu Pro Gln Asp Gly
          355                 360                 365

Ser Asn Ala Phe Ile Ser Gln Lys Gln Asn Ser Lys Ser Val Pro Ser
      370                 375                 380

Ala Lys Val Ser Leu Lys Glu Tyr Arg Ala Lys His Ala Glu Glu Leu
385                 390                 395                 400

Ala Ala Gln Lys Arg Gln Leu Glu Asn Met Glu Ala Asn Val Lys Ser
                405                 410                 415

Gln Tyr Ala Tyr Ala Ala Gln Asn Leu Leu Ser His His Asp Ser His
            420                 425                 430

Ser Ser Val Ile Leu Lys Met Pro Ile Glu Gly Ser Glu Asn Pro Glu
        435                 440                 445

Arg Pro Phe Leu Glu Lys Ala Asp Lys Thr Ala Leu Lys Met Arg Ile
    450                 455                 460

Pro Val Ala Gly Gly Asp Lys Ala Ala Ser Ser Lys Pro Glu Glu Ile
465                 470                 475                 480

Lys Met Arg Ile Lys Val His Ala Ala Ala Asp Lys His Asn Ser Val
                485                 490                 495

Glu Asp Ser Val Thr Lys Ser Arg Glu His Lys Glu Lys His Lys Thr
            500                 505                 510

His Pro Ser Asn His His His His Asn His Ser His Lys His
        515                 520                 525

Ser His Ser Gln Leu Pro Val Gly Thr Gly Asn Lys Arg Pro Gly Asp
    530                 535                 540

Pro Lys His Ser Ser Gln Thr Ser Asn Leu Ala His Lys Thr Tyr Ser
545                 550                 555                 560

Leu Ser Ser Ser Phe Ser Ser Ser Ser Thr Arg Lys Arg Gly Pro
                565                 570                 575

Ser Glu Glu Thr Gly Gly Ala Val Phe Asp His Pro Ala Lys Ile Ala
            580                 585                 590

Lys Ser Thr Lys Ser Ser Ser Leu Asn Phe Ser Phe Pro Ser Leu Pro
        595                 600                 605

Thr Met Gly Gln Met Pro Gly His Ser Ser Asp Thr Ser Gly Leu Ser
    610                 615                 620

Phe Ser Gln Pro Ser Cys Lys Thr Arg Val Pro His Ser Lys Leu Asp
625                 630                 635                 640

Lys Gly Pro Thr Gly Ala Asn Gly His Asn Thr Thr Gln Thr Ile Asp
                645                 650                 655

Tyr Gln Asp Thr Val Asn Met Leu His Ser Leu Leu Ser Ala Gln Gly
            660                 665                 670

Val Gln Pro Thr Gln Pro Thr Ala Phe Glu Phe Val Arg Pro Tyr Ser
        675                 680                 685

Asp Tyr Leu Asn Pro Arg Ser Gly Gly Ile Ser Ser Arg Ser Gly Asn
    690                 695                 700

Thr Asp Lys Pro Arg Pro Pro Leu Pro Ser Glu Pro Pro Pro
705                 710                 715                 720

Leu Pro Pro Leu Pro Lys
                725

<210> SEQ ID NO 4
<211> LENGTH: 2181
<212> TYPE: DNA

<213> ORGANISM: Homo sapiens

<400> SEQUENCE: 4

```
atggagggag agaggaagaa caacaacaaa cggtggtatt tcactcgaga acagctggaa      60
aatagcccat cccgtcgttt tggcgtggac ccagataaag aactttctta tcgccagcag     120
gcggccaatc tgcttcagga catggggcag cgtcttaacg tctcacaatt gactatcaac     180
actgctatag tatacatgca tcgattctac atgattcagt ccttcacaca gttccctgga     240
aattctgtgg ctccagcagc cttgtttcta gcagctaaag tggaggagca gcccaaaaaa     300
ttggaacatg tcatcaaggt agcacatact tgtctccatc ctcaggaatc ccttcctgat     360
actagaagtg aggcttattt gcaacaagtt caagatctgg tcattttaga aagcataatt     420
ttgcagactt taggctttga actaacaatt gatcacccac atactcatgt agtaaagtgc     480
actcaacttg ttcgagcaag caaggactta gcacagactt cttacttcat ggcaaccaac     540
agcctgcatt tgaccacatt tagcctgcag tacacacctc ctgtggtggc ctgtgtctgc     600
attcacctgg cttgcaagtg gtccaattgg agatcccag tctcaactga cgggaagcac     660
tggtgggagt atgttgacgc cactgtgacc ttggaacttt tagatgaact gacacatgag     720
tttctacaga ttttggagaa actcccaac aggctcaaac gcatttggaa ttggagggca     780
tgcgaggctg ccaagaaaac aaaagcagat gaccgaggaa cagatgaaaa gacttcagag     840
cagacaatcc tcaatatgat ttcccagagc tcttcagaca caaccattgc aggtttaatg     900
agcatgtcaa cttctaccac aagtgcagtg ccttccctgc agtctccga gagtcatcc      960
agcaacttaa ccgtgtggga gatgttgccg ggcaagcgtt ggctgtcctc ccaaccttct    1020
ttcaaactag aacctactca gggtcatcgg actagtgaga atttagcact tacaggagtt    1080
gatcattcct taccacagga tggttcaaat gcatttattt cccagaagca gaatagtaag    1140
agtgtgccat cagctaaagt gtcactgaaa gaataccgcg cgaagcatgc agaagaattg    1200
gctgcccaga gaggcaact ggagaacatg gaagccaatg tgaagtcaca atatgcatat    1260
gctgcccaga atctcctttc tcatcatgat agccattctt cagtcattct aaaaatgccc    1320
atagaggttt cagaaaaccc cgagcggcct tttctggaaa aggctgacaa aacagctctc    1380
aaaatgagaa tcccagtggc aggtggagat aaagctgcgt cttcaaaacc agaggagata    1440
aaaatgcgca taaagtcca tgctgcagct gataagcaca attctgtaga ggacagtgtt    1500
acaaagagcc gagagcacaa agaaaagcac aagactcacc catctaatca tcatcatcat    1560
cataatcacc actcacacaa gcactctcat tcccaacttc cagttggtac tgggaacaaa    1620
cgtcctggtg atccaaaaca tagtagccag acaagcaact tagcacataa aacctatagc    1680
ttgtctagtt ctttttcctc ttccagttct actcgtaaaa ggggaccctc tgaagagact    1740
ggaggggctg tgtttgatca tccagccaag attgccaaga gtactaaatc ctcttcccta    1800
aatttctcct ttccttcact tcctacaatg ggtcagatgc tgggcatag ctcagacaca     1860
agtggccttt ccttttcaca gcccagctgt aaaactcgtg tccctcattc gaaactggat    1920
aaagggccca ctggggccaa tggtcacaac acgacccaga caatagacta tcaagacact    1980
gtgaatatgc ttcactccct gctcagtgcc caggtgttc agcccactca gcctactgca    2040
tttgaatttg ttcgtcctta tagtgactat ctgaatcctc ggtctggtgg aatctcctcg    2100
agatctggca atacagacaa accccggcca ccacctctgc catcagaacc tcctccacca    2160
cttccacccc ttcctaagta a                                              2181
```

-continued

```
<210> SEQ ID NO 5
<211> LENGTH: 1000
<212> TYPE: DNA
<213> ORGANISM: Homo sapiens

<400> SEQUENCE: 5
tgagattaga agtaggcttg agaggccggg catggtggct catgcctgta gtcccagcac      60
tttgggaggc caaggcaggc ggatcaactg aggtcaggag ttcgagacca gcctggccaa     120
catggtgaaa cctcgtctct actaaaaata caaaaattag ccaggcatgg tgatgcacac     180
ctgtagttcc agctacttgg gaggctgaga caggagaatc gcttgaactc gggacgttag     240
gttgcagtga gccgagattg tgccactgca ctccagcctg gatgacaaag tgagactctg     300
tctcaaacaa acaaacaaac aaaaaacaac agtaacaaca aaaagaagt aggcttgaga      360 gcacatcttt tactttagca taaaaccta ccaaaatttc tagaactcag ttatggacta      420
actataatca taagcgaagg catggatgtt catgtatgaa ttttagataa gcatagattc     480
tttgttgtta ttattgcttt gtaacgtttg gatagattgc tgtgactctt aattgaaggt     540
tttaaaatct tctcttgatg gtaatattta ttggattaca tgttaggata gcctcctgcc     600
tgtggcctat ccagaacttc cagtgttgct gcaagtacaa tctactcatc tcagtgtttt     660
tttatttagt aaattaccta agtaaagaga tgctatttgc ttcattgcag gcatgcgagg     720
ctgccaagaa acaaaagca gatgaccgag aacagatga aaagacttca gagcagacaa      780
tcctcaatat gatttcccag agctcttcag acacaaccat tgcaggttta atgagcatgt     840
caacttctac cacaagtgca gtgccttccc tgccagtctc cgaagagtca tccagcaact     900
taaccagtgt ggagatgttg ccgggcaagc gttggctgtc ctcccaacct tctttcaaac     960
tagaacctac tcagggtcat cggactagtg agaatttagc                         1000

<210> SEQ ID NO 6
<211> LENGTH: 724
<212> TYPE: PRT
<213> ORGANISM: Mus musculus

<400> SEQUENCE: 6

Met Glu Gly Glu Arg Lys Asn Asn Lys Arg Trp Tyr Phe Thr Arg
1               5                   10                  15

Glu Gln Leu Glu Asn Ser Pro Ser Arg Arg Phe Gly Val Asp Ser Asp
            20                  25                  30

Lys Glu Leu Ser Tyr Arg Gln Gln Ala Ala Asn Leu Leu Gln Asp Met
        35                  40                  45

Gly Gln Arg Leu Asn Val Ser Gln Leu Thr Ile Asn Thr Ala Ile Val
    50                  55                  60

Tyr Met His Arg Phe Tyr Met Ile Gln Ser Phe Thr Gln Phe His Arg
65                  70                  75                  80

Tyr Ser Met Ala Pro Ala Ala Leu Phe Leu Ala Ala Lys Val Glu Glu
                85                  90                  95

Gln Pro Lys Lys Leu Glu His Val Ile Lys Val Ala His Thr Cys Leu
            100                 105                 110

His Pro Gln Glu Ser Leu Pro Asp Thr Arg Ser Glu Ala Tyr Leu Gln
        115                 120                 125

Gln Val Gln Asp Leu Val Ile Leu Glu Ser Ile Ile Leu Gln Thr Leu
    130                 135                 140

Gly Phe Glu Leu Thr Ile Asp His Pro His Thr His Val Val Lys Cys
145                 150                 155                 160
```

```
Thr Gln Leu Val Arg Ala Ser Lys Asp Leu Ala Gln Thr Ser Tyr Phe
                165                 170                 175
Met Ala Thr Asn Ser Leu His Leu Thr Thr Phe Ser Leu Gln Tyr Thr
            180                 185                 190
Pro Pro Val Val Ala Cys Val Cys Ile His Leu Ala Cys Lys Trp Ser
        195                 200                 205
Asn Trp Glu Ile Pro Val Ser Thr Asp Gly Lys His Trp Trp Glu Tyr
    210                 215                 220
Val Asp Ala Thr Val Thr Leu Glu Leu Leu Asp Gly Leu Thr His Glu
225                 230                 235                 240
Phe Leu Gln Ile Leu Glu Lys Thr Pro Ser Arg Leu Lys Arg Ile Arg
                245                 250                 255
Asn Trp Arg Ala Tyr Gln Ala Ala Met Lys Thr Lys Pro Asp Asp Arg
            260                 265                 270
Gly Ala Asp Glu Asn Thr Ser Glu Gln Thr Ile Leu Asn Met Ile Ser
        275                 280                 285
Gln Thr Ser Ser Asp Thr Thr Ile Ala Gly Leu Met Ser Met Ser Thr
    290                 295                 300
Ala Ser Thr Ser Ala Val Pro Ser Leu Pro Ser Ser Glu Glu Ser Ser
305                 310                 315                 320
Ser Ser Leu Thr Ser Val Asp Met Leu Gln Gly Glu Arg Trp Leu Ser
                325                 330                 335
Ser Gln Pro Pro Phe Lys Leu Glu Ala Ala Gln Gly His Arg Thr Ser
            340                 345                 350
Glu Ser Leu Ala Leu Ile Gly Val Asp His Ser Leu Gln Gln Asp Gly
        355                 360                 365
Ser Ser Ala Phe Gly Ser Gln Lys Gln Ala Ser Lys Ser Val Pro Ser
    370                 375                 380
Ala Lys Val Ser Leu Lys Glu Tyr Arg Ala Lys His Ala Glu Glu Leu
385                 390                 395                 400
Ala Ala Gln Lys Arg Gln Leu Glu Asn Met Glu Ala Asn Val Lys Ser
                405                 410                 415
Gln Tyr Ala Tyr Ala Ala Gln Asn Leu Leu Ser His Asp Ser His Ser
            420                 425                 430
Ser Val Ile Leu Lys Met Pro Ile Glu Ser Ser Glu Asn Pro Glu Arg
        435                 440                 445
Pro Phe Leu Asp Lys Ala Asp Lys Ser Ala Leu Lys Met Arg Leu Pro
    450                 455                 460
Val Ala Ser Gly Asp Lys Ala Val Ser Ser Lys Pro Glu Glu Ile Lys
465                 470                 475                 480
Met Arg Ile Lys Val His Ser Ala Gly Asp Lys His Asn Ser Ile Glu
                485                 490                 495
Asp Ser Val Thr Lys Ser Arg Glu His Lys Glu Lys Gln Arg Thr His
            500                 505                 510
Pro Ser Asn His His His His Asn His Ser Arg His Ser
        515                 520                 525
His Leu Gln Leu Pro Ala Gly Pro Val Ser Lys Arg Pro Ser Asp Pro
    530                 535                 540
Lys His Ser Ser Gln Thr Ser Thr Leu Ala His Lys Thr Tyr Ser Leu
545                 550                 555                 560
Ser Ser Thr Leu Ser Ser Ser Ser Thr Arg Lys Arg Gly Pro Pro
                565                 570                 575
Glu Glu Thr Gly Ala Ala Val Phe Asp His Pro Ala Lys Ile Ala Lys
```

-continued

```
                580                 585                 590
Ser Thr Lys Ser Ser Leu Asn Phe Pro Phe Pro Pro Leu Pro Thr Met
            595                 600                 605

Thr Gln Leu Pro Gly His Ser Ser Asp Thr Ser Gly Leu Pro Phe Ser
            610                 615                 620

Gln Pro Ser Cys Lys Thr Arg Val Pro His Met Lys Leu Asp Lys Gly
625                 630                 635                 640

Pro Pro Gly Ala Asn Gly His Asn Ala Thr Gln Ser Ile Asp Tyr Gln
                645                 650                 655

Asp Thr Val Asn Met Leu His Ser Leu Leu Ser Ala Gln Gly Val Gln
                660                 665                 670

Pro Thr Gln Ala Pro Ala Phe Glu Phe Val His Ser Tyr Gly Glu Tyr
            675                 680                 685

Met Asn Pro Arg Ala Gly Ala Ile Ser Ser Arg Ser Gly Thr Thr Asp
            690                 695                 700

Lys Pro Arg Pro Pro Leu Pro Ser Glu Pro Pro Pro Leu Pro
705                 710                 715                 720

Pro Leu Pro Lys

<210> SEQ ID NO 7
<211> LENGTH: 1071
<212> TYPE: PRT
<213> ORGANISM: Artificial Sequence
<220> FEATURE:
<223> OTHER INFORMATION: P411T, M412V, F414S human XPO1 mutant

<400> SEQUENCE: 7

Met Pro Ala Ile Met Thr Met Leu Ala Asp His Ala Ala Arg Gln Leu
1               5                   10                  15

Leu Asp Phe Ser Gln Lys Leu Asp Ile Asn Leu Leu Asp Asn Val Val
                20                  25                  30

Asn Cys Leu Tyr His Gly Glu Gly Ala Gln Gln Arg Met Ala Gln Glu
            35                  40                  45

Val Leu Thr His Leu Lys Glu His Pro Asp Ala Trp Thr Arg Val Asp
        50                  55                  60

Thr Ile Leu Glu Phe Ser Gln Asn Met Asn Thr Lys Tyr Tyr Gly Leu
65                  70                  75                  80

Gln Ile Leu Glu Asn Val Ile Lys Thr Arg Trp Lys Ile Leu Pro Arg
                85                  90                  95

Asn Gln Cys Glu Gly Ile Lys Lys Tyr Val Val Gly Leu Ile Ile Lys
            100                 105                 110

Thr Ser Ser Asp Pro Thr Cys Val Glu Lys Glu Lys Val Tyr Ile Gly
        115                 120                 125

Lys Leu Asn Met Ile Leu Val Gln Ile Leu Lys Gln Glu Trp Pro Lys
    130                 135                 140

His Trp Pro Thr Phe Ile Ser Asp Ile Val Gly Ala Ser Arg Thr Ser
145                 150                 155                 160

Glu Ser Leu Cys Gln Asn Asn Met Val Ile Leu Lys Leu Leu Ser Glu
                165                 170                 175

Glu Val Phe Asp Phe Ser Ser Gly Gln Ile Thr Gln Val Lys Ser Lys
            180                 185                 190

His Leu Lys Asp Ser Met Cys Asn Glu Phe Ser Gln Ile Phe Gln Leu
        195                 200                 205

Cys Gln Phe Val Met Glu Asn Ser Gln Asn Ala Pro Leu Val His Ala
    210                 215                 220
```

```
Thr Leu Glu Thr Leu Leu Arg Phe Leu Asn Trp Ile Pro Leu Gly Tyr
225                 230                 235                 240

Ile Phe Glu Thr Lys Leu Ile Ser Thr Leu Ile Tyr Lys Phe Leu Asn
            245                 250                 255

Val Pro Met Phe Arg Asn Val Ser Leu Lys Cys Leu Thr Glu Ile Ala
        260                 265                 270

Gly Val Ser Val Ser Gln Tyr Glu Glu Gln Phe Val Thr Leu Phe Thr
    275                 280                 285

Leu Thr Met Met Gln Leu Lys Gln Met Leu Pro Leu Asn Thr Asn Ile
290                 295                 300

Arg Leu Ala Tyr Ser Asn Gly Lys Asp Asp Glu Gln Asn Phe Ile Gln
305                 310                 315                 320

Asn Leu Ser Leu Phe Leu Cys Thr Phe Leu Lys Glu His Asp Gln Leu
                325                 330                 335

Ile Glu Lys Arg Leu Asn Leu Arg Glu Thr Leu Met Glu Ala Leu His
            340                 345                 350

Tyr Met Leu Leu Val Ser Glu Val Glu Glu Thr Glu Ile Phe Lys Ile
        355                 360                 365

Cys Leu Glu Tyr Trp Asn His Leu Ala Ala Glu Leu Tyr Arg Glu Ser
370                 375                 380

Pro Phe Ser Thr Ser Ala Ser Pro Leu Leu Ser Gly Ser Gln His Phe
385                 390                 395                 400

Asp Val Pro Arg Arg Gln Leu Tyr Leu Thr Val Leu Ser Lys Val
                405                 410                 415

Arg Leu Leu Met Val Ser Arg Met Ala Lys Pro Glu Glu Val Leu Val
                420                 425                 430

Val Glu Asn Asp Gln Gly Glu Val Val Arg Glu Phe Met Lys Asp Thr
                435                 440                 445

Asp Ser Ile Asn Leu Tyr Lys Asn Met Arg Glu Thr Leu Val Tyr Leu
    450                 455                 460

Thr His Leu Asp Tyr Val Asp Thr Glu Arg Ile Met Thr Glu Lys Leu
465                 470                 475                 480

His Asn Gln Val Asn Gly Thr Glu Trp Ser Trp Lys Asn Leu Asn Thr
                485                 490                 495

Leu Cys Trp Ala Ile Gly Ser Ile Ser Gly Ala Met His Glu Glu Asp
                500                 505                 510

Glu Lys Arg Phe Leu Val Thr Val Ile Lys Asp Leu Leu Gly Leu Cys
            515                 520                 525

Glu Gln Lys Arg Gly Lys Asp Asn Lys Ala Ile Ile Ala Ser Asn Ile
        530                 535                 540

Met Tyr Ile Val Gly Gln Tyr Pro Arg Phe Leu Arg Ala His Trp Lys
545                 550                 555                 560

Phe Leu Lys Thr Val Val Asn Lys Leu Phe Glu Phe Met His Glu Thr
                565                 570                 575

His Asp Gly Val Gln Asp Met Ala Cys Asp Thr Phe Ile Lys Ile Ala
                580                 585                 590

Gln Lys Cys Arg Arg His Phe Val Gln Val Gln Val Gly Glu Val Met
            595                 600                 605

Pro Phe Ile Asp Glu Ile Leu Asn Asn Ile Asn Thr Ile Ile Cys Asp
        610                 615                 620

Leu Gln Pro Gln Gln Val His Thr Phe Tyr Glu Ala Val Gly Tyr Met
625                 630                 635                 640
```

Ile Gly Ala Gln Thr Asp Gln Thr Val Gln Glu His Leu Ile Glu Lys
645 650 655

Tyr Met Leu Leu Pro Asn Gln Val Trp Asp Ser Ile Ile Gln Gln Ala
660 665 670

Thr Lys Asn Val Asp Ile Leu Lys Asp Pro Glu Thr Val Lys Gln Leu
675 680 685

Gly Ser Ile Leu Lys Thr Asn Val Arg Ala Cys Lys Ala Val Gly His
690 695 700

Pro Phe Val Ile Gln Leu Gly Arg Ile Tyr Leu Asp Met Leu Asn Val
705 710 715 720

Tyr Lys Cys Leu Ser Glu Asn Ile Ser Ala Ala Ile Gln Ala Asn Gly
725 730 735

Glu Met Val Thr Lys Gln Pro Leu Ile Arg Ser Met Arg Thr Val Lys
740 745 750

Arg Glu Thr Leu Lys Leu Ile Ser Gly Trp Val Ser Arg Ser Asn Asp
755 760 765

Pro Gln Met Val Ala Glu Asn Phe Val Pro Pro Leu Leu Asp Ala Val
770 775 780

Leu Ile Asp Tyr Gln Arg Asn Val Pro Ala Ala Arg Glu Pro Glu Val
785 790 795 800

Leu Ser Thr Met Ala Ile Ile Val Asn Lys Leu Gly Gly His Ile Thr
805 810 815

Ala Glu Ile Pro Gln Ile Phe Asp Ala Val Phe Glu Cys Thr Leu Asn
820 825 830

Met Ile Asn Lys Asp Phe Glu Glu Tyr Pro Glu His Arg Thr Asn Phe
835 840 845

Phe Leu Leu Leu Gln Ala Val Asn Ser His Cys Phe Pro Ala Phe Leu
850 855 860

Ala Ile Pro Pro Thr Gln Phe Lys Leu Val Leu Asp Ser Ile Ile Trp
865 870 875 880

Ala Phe Lys His Thr Met Arg Asn Val Ala Asp Thr Gly Leu Gln Ile
885 890 895

Leu Phe Thr Leu Leu Gln Asn Val Ala Gln Glu Glu Ala Ala Ala Gln
900 905 910

Ser Phe Tyr Gln Thr Tyr Phe Cys Asp Ile Leu Gln His Ile Phe Ser
915 920 925

Val Val Thr Asp Thr Ser His Thr Ala Gly Leu Thr Met His Ala Ser
930 935 940

Ile Leu Ala Tyr Met Phe Asn Leu Val Glu Glu Gly Lys Ile Ser Thr
945 950 955 960

Ser Leu Asn Pro Gly Asn Pro Val Asn Asn Gln Ile Phe Leu Gln Glu
965 970 975

Tyr Val Ala Asn Leu Leu Lys Ser Ala Phe Pro His Leu Gln Asp Ala
980 985 990

Gln Val Lys Leu Phe Val Thr Gly Leu Phe Ser Leu Asn Gln Asp Ile
995 1000 1005

Pro Ala Phe Lys Glu His Leu Arg Asp Phe Leu Val Gln Ile Lys
1010 1015 1020

Glu Phe Ala Gly Glu Asp Thr Ser Asp Leu Phe Leu Glu Glu Arg
1025 1030 1035

Glu Ile Ala Leu Arg Gln Ala Asp Glu Glu Lys His Lys Arg Gln
1040 1045 1050

Met Ser Val Pro Gly Ile Phe Asn Pro His Glu Ile Pro Glu Glu

Met Cys Asp
    1070

<210> SEQ ID NO 8
<211> LENGTH: 3216
<212> TYPE: DNA
<213> ORGANISM: Artificial Sequence
<220> FEATURE:
<223> OTHER INFORMATION: P411T, M412V, F414S human XPO1 mutant

<400> SEQUENCE: 8

| | | |
|---|---|---|
| atgccagcaa ttatgacaat gttagcagac catgcagctc gtcagctgct tgatttcagc | 60 |
| caaaaactgg atatcaactt attagataat gtggtgaatt gcttatacca tggagaagga | 120 |
| gcccagcaaa gaatggctca agaagtactg acacatttaa aggagcatcc tgatgcttgg | 180 |
| acaagagtcg acacaatttt ggaattttct cagaatatga atacgaaata ctatggacta | 240 |
| caaattttgg aaaatgtgat aaaaacaagg tggaagattc ttccaaggaa ccagtgcgaa | 300 |
| ggaataaaaa aatacgttgt tggcctcatt atcaagacgt catctgaccc aacttgtgta | 360 |
| gagaaagaaa aggtgtatat cggaaaatta aatatgatcc ttgttcagat actgaaacaa | 420 |
| gaatggccca acattggcc aacttttatc agtgatattg ttggagcaag taggaccagc | 480 |
| gaaagtctct gtcaaaataa tatggtgatt cttaaactct gagtgaaga agtatttgat | 540 |
| ttctctagtg gacagataac ccaagtcaaa tctaagcatt aaaagacag catgtgcaat | 600 |
| gaattctcac agatatttca actgtgtcag tttgtaatgg aaaattctca aaatgctcca | 660 |
| cttgtacatg caaccttgga acattgctc agatttctga actggattcc cctgggatat | 720 |
| attttgaga ccaaattaat cagcacattg atttataagt tcctgaatgt tccaatgttt | 780 |
| cgaaatgtct ctctgaagtg cctcactgag attgctggtg tgagtgtaag ccaatatgaa | 840 |
| gaacaatttg taacactatt tactctgaca atgatgcaac taaagcagat gcttccttta | 900 |
| aataccaata ttcgacttgc gtactcaaat ggaaaagatg atgaacagaa cttcattcaa | 960 |
| aatctcagtt tgtttctctg caccttttctt aaggaacatg atcaactat agaaaaaaga | 1020 |
| ttaaatctca gggaaaactct tatggaggcc cttcattata tgttgttggt atctgaagta | 1080 |
| gaagaaactg aaatctttaa aatttgtctt gaatactgga tcatttggc tgctgaactc | 1140 |
| tatagagaga gtccattctc tacatctgcg tctccgttgc tttctggaag tcaacatttt | 1200 |
| gatgttcctc ccaggagaca gctgtatttg accgtgttat caaaggtccg tttattaatg | 1260 |
| gttagtcgaa tggctaaacc agaggaagta ttggttgtag agaatgatca aggagaagtt | 1320 |
| gtgagagaat tcatgaagga tacagattcc ataaatttgt ataagaatat gagggaaaca | 1380 |
| ttggtttatc ttactcatct ggattatgta gatacagaaa gaataatgac agagaagctt | 1440 |
| cacaatcaag tgaatggtac agagtggtca tggaaaaatt tgaatacatt gtgttgggca | 1500 |
| ataggctcca ttagtggagc aatgcatgaa gaggacgaaa aacgatttct tgttactgtt | 1560 |
| ataaaggatc tattaggatt atgtgaacag aaaagaggca agataataa agctattatt | 1620 |
| gcatcaaata tcatgtacat agtaggtcaa tacccacgtt ttttgagagc tcactggaaa | 1680 |
| tttctgaaga ctgtagttaa caagctgttc gaattcatgc atgagaccca tgatgagtc | 1740 |
| caggatatgg cttgtgatac tttcattaaa atagcccaaa aatgccgcag gcatttcgtt | 1800 |
| caggttcagg ttgagaagt gatgccattt attgatgaaa ttttgaacaa cattaacact | 1860 |
| attatttgtg atcttcagcc tcaacaggtt catacgtttt atgaagctgt ggggtacatg | 1920 |

```
attggtgcac aaacagatca aacagtacaa gaacacttga tagaaaagta catgttactc    1980
cctaatcaag tgtgggatag tataatccag caggcaacca aaaatgtgga tatactgaaa    2040
gatcctgaaa cagtcaagca gcttggtagc attttgaaaa caaatgtgag agcctgcaaa    2100
gctgttggac acccctttgt aattcagctt ggaagaattt atttagatat gcttaatgta    2160
tacaagtgcc tcagtgaaaa tatttctgca gctatccaag ctaatggtga aatggttaca    2220
aagcaaccat tgattagaag tatgcgaact gtaaaaaggg aaactttaaa gttaatatct    2280
ggttgggtga gccgatccaa tgatccacag atggtcgctg aaaattttgt tccccctctg    2340
ttggatgcag ttctcattga ttatcagaga aatgtcccag ctgctagaga accagaagtg    2400
cttagtacta tggccataat tgtcaacaag ttaggggac atataacagc tgaaatacct     2460
caaatatttg atgctgtttt tgaatgcaca ttgaatatga taaataagga ctttgaagaa    2520
tatcctgaac atagaacgaa cttttctta ctacttcagg ctgtcaattc tcattgtttc     2580
ccagcattcc ttgctattcc acctacacag tttaaacttg ttttggattc catcatttgg    2640
gctttcaaac atactatgag gaatgtcgca gatacgggct tacagatact ttttacactc    2700
ttacaaaatg ttgcacaaga agaagctgca gctcagagtt tttatcaaac ttattttgt    2760 gatattctcc agcatatctt ttctgttgtg acagacactt cacatactgc tggtttaaca    2820
atgcatgcat caattcttgc atatatgttt aatttggttg aagaaggaaa ataagtaca    2880 tcattaaatc ctggaaatcc agttaacaac caaatctttc ttcaggaata tgtggctaat    2940
ctccttaagt cggccttccc tcacctacaa gatgctcaag taaagctctt tgtgacaggg    3000
cttttcagct aaatcaaga tattcctgct ttcaaggaac atttaagaga tttcctagtt    3060
caaataaagg aatttgcagg tgaagacact tctgatttgt ttttggaaga gagagaaata    3120
gccctacggc aggctgatga agagaaacat aaacgtcaaa tgtctgtccc tggcatctttt   3180 aatccacatg agattccaga gaaatgtgt gattaa                                3216
```

<210> SEQ ID NO 9
<211> LENGTH: 1071
<212> TYPE: PRT
<213> ORGANISM: Homo sapiens

<400> SEQUENCE: 9

```
Met Pro Ala Ile Met Thr Met Leu Ala Asp His Ala Ala Arg Gln Leu
1               5                   10                  15

Leu Asp Phe Ser Gln Lys Leu Asp Ile Asn Leu Leu Asp Asn Val Val
            20                  25                  30

Asn Cys Leu Tyr His Gly Glu Gly Ala Gln Gln Arg Met Ala Gln Glu
        35                  40                  45

Val Leu Thr His Leu Lys Glu His Pro Asp Ala Trp Thr Arg Val Asp
    50                  55                  60

Thr Ile Leu Glu Phe Ser Gln Asn Met Asn Thr Lys Tyr Tyr Gly Leu
65                  70                  75                  80

Gln Ile Leu Glu Asn Val Ile Lys Thr Arg Trp Lys Ile Leu Pro Arg
                85                  90                  95

Asn Gln Cys Glu Gly Ile Lys Lys Tyr Val Val Gly Leu Ile Ile Lys
            100                 105                 110

Thr Ser Ser Asp Pro Thr Cys Val Glu Lys Glu Lys Val Tyr Ile Gly
        115                 120                 125

Lys Leu Asn Met Ile Leu Val Gln Ile Leu Lys Gln Glu Trp Pro Lys
    130                 135                 140
```

-continued

His Trp Pro Thr Phe Ile Ser Asp Ile Val Gly Ala Ser Arg Thr Ser
145                 150                 155                 160

Glu Ser Leu Cys Gln Asn Asn Met Val Ile Leu Lys Leu Leu Ser Glu
            165                 170                 175

Glu Val Phe Asp Phe Ser Ser Gly Gln Ile Thr Gln Val Lys Ser Lys
        180                 185                 190

His Leu Lys Asp Ser Met Cys Asn Glu Phe Ser Gln Ile Phe Gln Leu
    195                 200                 205

Cys Gln Phe Val Met Glu Asn Ser Gln Asn Ala Pro Leu Val His Ala
    210                 215                 220

Thr Leu Glu Thr Leu Leu Arg Phe Leu Asn Trp Ile Pro Leu Gly Tyr
225                 230                 235                 240

Ile Phe Glu Thr Lys Leu Ile Ser Thr Leu Ile Tyr Lys Phe Leu Asn
                245                 250                 255

Val Pro Met Phe Arg Asn Val Ser Leu Lys Cys Leu Thr Glu Ile Ala
            260                 265                 270

Gly Val Ser Val Ser Gln Tyr Glu Glu Gln Phe Val Thr Leu Phe Thr
        275                 280                 285

Leu Thr Met Met Gln Leu Lys Gln Met Leu Pro Leu Asn Thr Asn Ile
290                 295                 300

Arg Leu Ala Tyr Ser Asn Gly Lys Asp Asp Glu Gln Asn Phe Ile Gln
305                 310                 315                 320

Asn Leu Ser Leu Phe Leu Cys Thr Phe Leu Lys Glu His Asp Gln Leu
                325                 330                 335

Ile Glu Lys Arg Leu Asn Leu Arg Glu Thr Leu Met Glu Ala Leu His
            340                 345                 350

Tyr Met Leu Leu Val Ser Glu Val Glu Thr Glu Ile Phe Lys Ile
        355                 360                 365

Cys Leu Glu Tyr Trp Asn His Leu Ala Ala Glu Leu Tyr Arg Glu Ser
        370                 375                 380

Pro Phe Ser Thr Ser Ala Ser Pro Leu Leu Ser Gly Ser Gln His Phe
385                 390                 395                 400

Asp Val Pro Pro Arg Arg Gln Leu Tyr Leu Pro Met Leu Phe Lys Val
            405                 410                 415

Arg Leu Leu Met Val Ser Arg Met Ala Lys Pro Glu Glu Val Leu Val
        420                 425                 430

Val Glu Asn Asp Gln Gly Glu Val Val Arg Glu Phe Met Lys Asp Thr
            435                 440                 445

Asp Ser Ile Asn Leu Tyr Lys Asn Met Arg Glu Thr Leu Val Tyr Leu
450                 455                 460

Thr His Leu Asp Tyr Val Asp Thr Glu Arg Ile Met Thr Glu Lys Leu
465                 470                 475                 480

His Asn Gln Val Asn Gly Thr Glu Trp Ser Trp Lys Asn Leu Asn Thr
                485                 490                 495

Leu Cys Trp Ala Ile Gly Ser Ile Ser Gly Ala Met His Glu Glu Asp
            500                 505                 510

Glu Lys Arg Phe Leu Val Thr Val Ile Lys Asp Leu Leu Gly Leu Cys
        515                 520                 525

Glu Gln Lys Arg Gly Lys Asp Asn Lys Ala Ile Ile Ala Ser Asn Ile
    530                 535                 540

Met Tyr Ile Val Gly Gln Tyr Pro Arg Phe Leu Arg Ala His Trp Lys
545                 550                 555                 560

Phe Leu Lys Thr Val Val Asn Lys Leu Phe Glu Phe Met His Glu Thr

```
                565                 570                 575
His Asp Gly Val Gln Asp Met Ala Cys Asp Thr Phe Ile Lys Ile Ala
            580                 585                 590

Gln Lys Cys Arg Arg His Phe Val Gln Val Gln Val Gly Glu Val Met
        595                 600                 605

Pro Phe Ile Asp Glu Ile Leu Asn Asn Ile Asn Thr Ile Ile Cys Asp
    610                 615                 620

Leu Gln Pro Gln Gln Val His Thr Phe Tyr Glu Ala Val Gly Tyr Met
625                 630                 635                 640

Ile Gly Ala Gln Thr Asp Gln Thr Val Gln Glu His Leu Ile Glu Lys
                645                 650                 655

Tyr Met Leu Leu Pro Asn Gln Val Trp Asp Ser Ile Ile Gln Gln Ala
            660                 665                 670

Thr Lys Asn Val Asp Ile Leu Lys Asp Pro Glu Thr Val Lys Gln Leu
        675                 680                 685

Gly Ser Ile Leu Lys Thr Asn Val Arg Ala Cys Lys Ala Val Gly His
    690                 695                 700

Pro Phe Val Ile Gln Leu Gly Arg Ile Tyr Leu Asp Met Leu Asn Val
705                 710                 715                 720

Tyr Lys Cys Leu Ser Glu Asn Ile Ser Ala Ile Gln Ala Asn Gly
                725                 730                 735

Glu Met Val Thr Lys Gln Pro Leu Ile Arg Ser Met Arg Thr Val Lys
            740                 745                 750

Arg Glu Thr Leu Lys Leu Ile Ser Gly Trp Val Ser Arg Ser Asn Asp
        755                 760                 765

Pro Gln Met Val Ala Glu Asn Phe Val Pro Pro Leu Leu Asp Ala Val
    770                 775                 780

Leu Ile Asp Tyr Gln Arg Asn Val Pro Ala Ala Arg Glu Pro Glu Val
785                 790                 795                 800

Leu Ser Thr Met Ala Ile Ile Val Asn Lys Leu Gly Gly His Ile Thr
                805                 810                 815

Ala Glu Ile Pro Gln Ile Phe Asp Ala Val Phe Glu Cys Thr Leu Asn
            820                 825                 830

Met Ile Asn Lys Asp Phe Glu Glu Tyr Pro Glu His Arg Thr Asn Phe
        835                 840                 845

Phe Leu Leu Leu Gln Ala Val Asn Ser His Cys Phe Pro Ala Phe Leu
    850                 855                 860

Ala Ile Pro Pro Thr Gln Phe Lys Leu Val Leu Asp Ser Ile Ile Trp
865                 870                 875                 880

Ala Phe Lys His Thr Met Arg Asn Val Ala Asp Thr Gly Leu Gln Ile
                885                 890                 895

Leu Phe Thr Leu Leu Gln Asn Val Ala Gln Glu Ala Ala Ala Gln
            900                 905                 910

Ser Phe Tyr Gln Thr Tyr Phe Cys Asp Ile Leu Gln His Ile Phe Ser
        915                 920                 925

Val Val Thr Asp Thr Ser His Thr Ala Gly Leu Thr Met His Ala Ser
    930                 935                 940

Ile Leu Ala Tyr Met Phe Asn Leu Val Glu Glu Gly Lys Ile Ser Thr
945                 950                 955                 960

Ser Leu Asn Pro Gly Asn Pro Val Asn Gln Ile Phe Leu Gln Glu
                965                 970                 975

Tyr Val Ala Asn Leu Leu Lys Ser Ala Phe Pro His Leu Gln Asp Ala
            980                 985                 990
```

```
Gln Val Lys Leu Phe Val Thr Gly Leu Phe Ser Leu Asn  Gln Asp Ile
        995                 1000                1005

Pro Ala  Phe Lys Glu His Leu  Arg Asp Phe Leu  Val  Gln Ile Lys
   1010              1015                1020

Glu Phe  Ala Gly Glu Asp Thr  Ser Asp Leu Phe  Leu  Glu Glu Arg
   1025              1030                1035

Glu Ile  Ala Leu Arg Gln Ala  Asp Glu Glu Lys  His  Lys Arg Gln
   1040              1045                1050

Met Ser  Val Pro Gly Ile Phe  Asn Pro His Glu  Ile  Pro Glu Glu
   1055              1060                1065

Met Cys  Asp
   1070

<210> SEQ ID NO 10
<211> LENGTH: 3216
<212> TYPE: DNA
<213> ORGANISM: Homo sapiens

<400> SEQUENCE: 10
atgccagcaa ttatgacaat gttagcagac catgcagctc gtcagctgct tgatttcagc      60
caaaaactgg atatcaactt attagataat gtggtgaatt gcttatacca tggagaagga     120
gcccagcaaa gaatggctca agaagtactg acacatttaa aggagcatcc tgatgcttgg     180
acaagagtcg acacaatttt ggaattttct cagaatatga atacgaaata ctatggacta     240
caaattttgg aaaatgtgat aaaaacaagg tggaagattc ttccaaggaa ccagtgcgaa     300
ggaataaaaa aatacgttgt tggcctcatt atcaagacgt catctgaccc aacttgtgta     360
gagaaagaaa aggtgtatat cggaaaatta aatatgatcc ttgttcagat actgaaacaa     420
gaatggccca acattggcc aacttttatc agtgatattg ttggagcaag taggaccagc     480
gaaagtctct gtcaaaataa tatggtgatt cttaaactct gagtgaaga agtatttgat     540 ttctctagtg acagataac ccaagtcaaa tctaagcatt aaaagacag catgtgcaat     600 gaattctcac agatatttca actgtgtcag tttgtaatgg aaaattctca aaatgctcca     660
cttgtacatg caaccttgga acattgctc agatttctga actggattcc cctgggatat     720 attttgaga ccaaattaat cagcacattg atttataagt tcctgaatgt tccaatgttt     780
cgaaatgtct ctctgaagtg cctcactgag attgctggtg tgagtgtaag ccaatatgaa     840
gaacaatttg taacactatt tactctgaca atgatgcaac taaagcagat gcttccttta     900
aataccaata ttcgacttgc gtactcaaat ggaaaagatg atgaacagaa cttcattcaa     960
aatctcagtt tgtttctctg cacctttctt aaggaacatg atcaacttat agaaaaaaga    1020
ttaaatctca gggaaactct tatggaggcc cttcattata tgttgttggt atctgaagta    1080
gaagaaactg aaatctttaa aatttgtctt gaatactgga atcatttggc tgctgaactc    1140
tatagagaga gtccattctc tacatctgcc tctccgttgc tttctggaag tcaacatttt    1200
gatgttcctc ccaggagaca gctatatttg cccatgttat tcaaggtccg tttattaatg    1260
gttagtcgaa tggctaaacc agaggaagta ttggttgtag agaatgatca aggagaagtt    1320
gtgagagaat tcatgaagga tacagattcc ataaatttgt ataagaatat gagggaaaca    1380
ttggtttatc ttactcatct ggattatgta gatacagaaa gaataatgac agagaagctt    1440
cacaatcaag tgaatggtac agagtggtca tggaaaaatt tgaatacatt gtgttgggca    1500
ataggctcca ttagtggagc aatgcatgaa gaggacgaaa aacgatttct tgttactgtt    1560
```

| | |
|---|---:|
| ataaaggatc tattaggatt atgtgaacag aaaagaggca agataataa agctattatt | 1620 |
| gcatcaaata tcatgtacat agtaggtcaa tacccacgtt ttttgagagc tcactggaaa | 1680 |
| tttctgaaga ctgtagttaa caagctgttc gaattcatgc atgagaccca tgatggagtc | 1740 |
| caggatatgg cttgtgatac tttcattaaa atagcccaaa aatgccgcag gcatttcgtt | 1800 |
| caggttcagg ttggagaagt gatgccattt attgatgaaa ttttgaacaa cattaacact | 1860 |
| attatttgtg atcttcagcc tcaacaggtt catacgtttt atgaagctgt ggggtacatg | 1920 |
| attggtgcac aaacagatca aacagtacaa gaacacttga tagaaaagta catgttactc | 1980 |
| cctaatcaag tgtgggatag tataatccag caggcaacca aaatgtgga tatactgaaa | 2040 |
| gatcctgaaa cagtcaagca gcttggtagc attttgaaaa caaatgtgag agcctgcaaa | 2100 |
| gctgttggac accctttgt aattcagctt ggaagaattt atttagatat gcttaatgta | 2160 |
| tacaagtgcc tcagtgaaaa atttctgca gctatccaag ctaatggtga aatggttaca | 2220 |
| aagcaaccat tgattagaag tatgcgaact gtaaaaaggg aaactttaaa gttaatatct | 2280 |
| ggttgggtga gccgatccaa tgatcccacag atggtcgctg aaaattttgt tcccccctctg | 2340 |
| ttggatgcag ttctcattga ttatcagaga aatgtcccag ctgctagaga accagaagtg | 2400 |
| cttagtacta tggccataat tgtcaacaag ttaggggggac atataacagc tgaaatacct | 2460 |
| caaatatttg atgctgtttt tgaatgcaca ttgaatatga taaataagga ctttgaagaa | 2520 |
| tatcctgaac atagaacgaa cttttttctta ctacttcagg ctgtcaattc tcattgtttc | 2580 |
| ccagcattcc ttgctattcc acctacacag tttaaacttg ttttggattc catcatttgg | 2640 |
| gctttcaaac atactatgag gaatgtcgca gatacgggct tacagatact ttttacactc | 2700 |
| ttacaaaatg ttgcacaaga agaagctgca gctcagagtt tttatcaaac ttattttgt | 2760 |
| gatattctcc agcatatctt ttctgttgtg acagacactt cacatactgc tggtttaaca | 2820 |
| atgcatgcat caattcttgc atatatgttt aatttggttg aagaaggaaa aataagtaca | 2880 |
| tcattaaatc ctggaaatcc agttaacaac caaatctttc ttcaggaata tgtggctaat | 2940 |
| ctccttaagt cggccttccc tcacctacaa gatgctcaag taaagctctt tgtgacaggg | 3000 |
| cttttcagct aaatcaaga tattcctgct ttcaaggaac atttaagaga tttcctagtt | 3060 |
| caaataaagg aatttgcagg tgaagacact tctgatttgt ttttggaaga gagagaaata | 3120 |
| gccctacggc aggctgatga agagaaacat aaacgtcaaa tgtctgtccc tggcatcttt | 3180 |
| aatccacatg agattccaga agaaatgtgt gattaa | 3216 |

<210> SEQ ID NO 11
<211> LENGTH: 977
<212> TYPE: DNA
<213> ORGANISM: Homo sapiens

<400> SEQUENCE: 11

| | |
|---|---:|
| ttctctcctc tgtgatggta catttgggtt gtgataccac ttattggcac ccaaggcctt | 60 |
| ttaaataaat gtcgttccat taggagacat gataaaaata catattgatc aactactatg | 120 |
| tgagagattt ttgaagtgct ttagggcatg tcagaagaag cagagttact ccagagtttg | 180 |
| ctgtctattt gataagtatt gaatctgag ttgtgatgaa taaaacatga atttttattt | 240 |
| tcccttaagg tgtaacaagt gaaaagcaat ttgaagttgg taatgtttaa gaattatttt | 300 |
| aacagttttg gtcttctgtg taggcccttc attatatgtt gttggtatct gaagtagaag | 360 |
| aaactgaaat ctttaaaatt tgtcttgaat actggaatca tttggctgct gaactctata | 420 |
| gagagagtcc attctctaca tctgcctctc cgttgctttc tggaagtcaa cattttgatg | 480 |

-continued

```
ttcctcccag gagacagcta tatttgccca tgttattcaa ggtaacagag cggttggttg    540
agtgttcttc ctgttgcata ctgtggtttt gaggtctgaa tccaaatact tctaatctgt    600
gtaaataaat tagctataaa aagagaaccc aacaacttct ccatgagtgt ggaaaactag    660
aacatgaaag gagttgagtc tagaaccttg attctcaaga gtgtggtcct tctctcagta    720
tcaacattgg ttgtgatttc gttaggcaaa tcattggcc acctgccaat ctactaaacc     780
agagtctagg aatgagacac aggaaactcc tgtaacagaa gttggttaaa aaatcacat     840 taaaacacac ttaaataatt ataaagccat ttttgtagaa ttacagtgaa aaaaatttt     900 ttcttttgga gacagggtct tgctctgtgg ctcaggttgg agtgcagtgg cgtggtcata    960
gctcactaca atcttga                                                   977
```

```
<210> SEQ ID NO 12
<211> LENGTH: 1071
<212> TYPE: PRT
<213> ORGANISM: Mus musculus

<400> SEQUENCE: 12
```

```
Met Pro Ala Ile Met Thr Met Leu Ala Asp His Ala Ala Arg Gln Leu
1               5                   10                  15

Leu Asp Phe Ser Gln Lys Leu Asp Ile Asn Leu Leu Asp Asn Val Val
            20                  25                  30

Asn Cys Leu Tyr His Gly Glu Gly Ala Gln Gln Arg Met Ala Gln Glu
        35                  40                  45

Val Leu Thr His Leu Lys Glu His Pro Asp Ala Trp Thr Arg Val Asp
    50                  55                  60

Thr Ile Leu Glu Phe Ser Gln Asn Met Asn Thr Lys Tyr Tyr Gly Leu
65                  70                  75                  80

Gln Ile Leu Glu Asn Val Ile Lys Thr Arg Trp Lys Ile Leu Pro Arg
                85                  90                  95

Asn Gln Cys Glu Gly Ile Lys Lys Tyr Val Val Gly Leu Ile Ile Lys
            100                 105                 110

Thr Ser Ser Asp Pro Thr Cys Val Glu Lys Glu Lys Val Tyr Ile Gly
        115                 120                 125

Lys Leu Asn Met Ile Leu Val Gln Ile Leu Lys Gln Glu Trp Pro Lys
    130                 135                 140

His Trp Pro Thr Phe Ile Ser Asp Ile Val Gly Ala Ser Arg Thr Ser
145                 150                 155                 160

Glu Ser Leu Cys Gln Asn Asn Met Val Ile Leu Lys Leu Leu Ser Glu
                165                 170                 175

Glu Val Phe Asp Phe Ser Ser Gly Gln Ile Thr Gln Val Lys Ala Lys
            180                 185                 190

His Leu Lys Asp Ser Met Cys Asn Glu Phe Ser Gln Ile Phe Gln Leu
        195                 200                 205

Cys Gln Phe Val Met Glu Asn Ser Gln Asn Ala Pro Leu Val His Ala
    210                 215                 220

Thr Leu Glu Thr Leu Leu Arg Phe Leu Asn Trp Ile Pro Leu Gly Tyr
225                 230                 235                 240

Ile Phe Glu Thr Lys Leu Ile Ser Thr Leu Ile Tyr Lys Phe Leu Asn
                245                 250                 255

Val Pro Met Phe Arg Asn Val Ser Leu Lys Cys Leu Thr Glu Ile Ala
            260                 265                 270

Gly Val Ser Val Ser Gln Tyr Glu Glu Gln Phe Glu Thr Leu Phe Thr
```

-continued

```
                275                 280                 285
Leu Thr Met Met Gln Leu Lys Gln Met Leu Pro Leu Asn Thr Asn Ile
290                 295                 300
Arg Leu Ala Tyr Ser Asn Gly Lys Asp Asp Glu Gln Asn Phe Ile Gln
305                 310                 315                 320
Asn Leu Ser Leu Phe Leu Cys Thr Phe Leu Lys Glu His Gly Gln Leu
                325                 330                 335
Leu Glu Lys Arg Leu Asn Leu Arg Glu Ala Leu Met Glu Ala Leu His
                340                 345                 350
Tyr Met Leu Leu Val Ser Glu Val Glu Thr Glu Ile Phe Lys Ile
                355                 360                 365
Cys Leu Glu Tyr Trp Asn His Leu Ala Ala Glu Leu Tyr Arg Glu Ser
370                 375                 380
Pro Phe Ser Thr Ser Ala Ser Pro Leu Leu Ser Gly Ser Gln His Phe
385                 390                 395                 400
Asp Ile Pro Pro Arg Arg Gln Leu Tyr Leu Thr Val Leu Ser Lys Val
                405                 410                 415
Arg Leu Leu Met Val Ser Arg Met Ala Lys Pro Glu Glu Val Leu Val
                420                 425                 430
Val Glu Asn Asp Gln Gly Glu Val Val Arg Glu Phe Met Lys Asp Thr
                435                 440                 445
Asp Ser Ile Asn Leu Tyr Lys Asn Met Arg Glu Thr Leu Val Tyr Leu
450                 455                 460
Thr His Leu Asp Tyr Val Asp Thr Glu Ile Ile Met Thr Lys Lys Leu
465                 470                 475                 480
Gln Asn Gln Val Asn Gly Thr Glu Trp Ser Trp Lys Asn Leu Asn Thr
                485                 490                 495
Leu Cys Trp Ala Ile Gly Ser Ile Ser Gly Ala Met His Glu Glu Asp
                500                 505                 510
Glu Lys Arg Phe Leu Val Thr Val Ile Lys Asp Leu Leu Gly Leu Cys
                515                 520                 525
Glu Gln Lys Arg Gly Lys Asp Asn Lys Ala Ile Ile Ala Ser Asn Ile
530                 535                 540
Met Tyr Ile Val Gly Gln Tyr Pro Arg Phe Leu Arg Ala His Trp Lys
545                 550                 555                 560
Phe Leu Lys Thr Val Val Asn Lys Leu Phe Glu Phe Met His Glu Thr
                565                 570                 575
His Asp Gly Val Gln Asp Met Ala Cys Asp Thr Phe Ile Lys Ile Ala
                580                 585                 590
Gln Lys Cys Arg Arg His Phe Val Gln Val Gln Val Gly Glu Val Met
                595                 600                 605
Pro Phe Ile Asp Glu Ile Leu Asn Asn Ile Asn Thr Ile Ile Cys Asp
                610                 615                 620
Leu Gln Pro Gln Gln Val His Thr Phe Tyr Glu Ala Val Gly Tyr Met
625                 630                 635                 640
Ile Gly Ala Gln Thr Asp Gln Thr Val Gln Glu His Leu Ile Glu Lys
                645                 650                 655
Tyr Met Leu Leu Pro Asn Gln Val Trp Asp Ser Ile Ile Gln Gln Ala
                660                 665                 670
Thr Lys Asn Val Asp Ile Leu Lys Asp Pro Glu Thr Val Lys Gln Leu
                675                 680                 685
Gly Ser Ile Leu Lys Thr Asn Val Arg Ala Cys Lys Ala Val Gly His
                690                 695                 700
```

Pro Phe Val Ile Gln Leu Gly Arg Ile Tyr Leu Asp Met Leu Asn Val
705                 710                 715                 720

Tyr Lys Cys Leu Ser Glu Asn Ile Ser Ala Ile Gln Ala Asn Gly
            725                 730                 735

Glu Met Val Thr Lys Gln Pro Leu Ile Arg Ser Met Arg Thr Val Lys
            740                 745                 750

Arg Glu Thr Leu Lys Leu Ile Ser Gly Trp Val Ser Arg Ser Asn Asp
            755                 760                 765

Pro Gln Met Val Ala Glu Asn Phe Val Pro Pro Leu Leu Asp Ala Val
            770                 775                 780

Leu Ile Asp Tyr Gln Arg Asn Val Pro Ala Ala Arg Glu Pro Glu Val
785                 790                 795                 800

Leu Ser Thr Met Ala Ile Ile Val Asn Lys Leu Gly Gly His Ile Thr
                805                 810                 815

Ala Glu Ile Pro Gln Ile Phe Asp Ala Val Phe Glu Cys Thr Leu Asn
                820                 825                 830

Met Ile Asn Lys Asp Phe Glu Glu Tyr Pro Glu His Arg Thr Asn Phe
                835                 840                 845

Phe Leu Leu Leu Gln Ala Val Asn Ser His Cys Phe Pro Ala Phe Leu
850                 855                 860

Ala Ile Pro Pro Ala Gln Phe Lys Leu Val Leu Asp Ser Ile Ile Trp
865                 870                 875                 880

Ala Phe Lys His Thr Met Arg Asn Val Ala Asp Thr Gly Leu Gln Ile
                885                 890                 895

Leu Phe Thr Leu Leu Gln Asn Val Ala Gln Glu Glu Ala Ala Ala Gln
                900                 905                 910

Ser Phe Tyr Gln Thr Tyr Phe Cys Asp Ile Leu Gln His Ile Phe Ser
                915                 920                 925

Val Val Thr Asp Thr Ser His Thr Ala Gly Leu Thr Met His Ala Ser
930                 935                 940

Ile Leu Ala Tyr Met Phe Asn Leu Val Glu Glu Gly Lys Ile Ser Thr
945                 950                 955                 960

Pro Leu Asn Pro Gly Asn Pro Val Asn Asn Gln Met Phe Ile Gln Asp
                965                 970                 975

Tyr Val Ala Asn Leu Leu Lys Ser Ala Phe Pro His Leu Gln Asp Ala
                980                 985                 990

Gln Val Lys Leu Phe Val Thr Gly Leu Phe Ser Leu Asn Gln Asp Ile
            995                 1000                1005

Pro Ala Phe Lys Glu His Leu Arg Asp Phe Leu Val Gln Ile Lys
    1010                1015                1020

Glu Phe Ala Gly Glu Asp Thr Ser Asp Leu Phe Leu Glu Glu Arg
    1025                1030                1035

Glu Thr Ala Leu Arg Gln Ala Gln Glu Glu Lys His Lys Leu Gln
    1040                1045                1050

Met Ser Val Pro Gly Ile Leu Asn Pro His Glu Ile Pro Glu Glu
    1055                1060                1065

Met Cys Asp
    1070

<210> SEQ ID NO 13
<211> LENGTH: 119
<212> TYPE: DNA
<213> ORGANISM: Artificial Sequence
<220> FEATURE:

<223> OTHER INFORMATION: hCCNT1 HDR donor template

<400> SEQUENCE: 13
gtgttttttt atttagtaaa ttacctaagt aaagagatgc tatttgcttc attgcaggcg    60
tacgaagctg ccaagaaaac aaaagcagat gaccgaggaa cagatgaaaa gacttcaga   119

<210> SEQ ID NO 14
<211> LENGTH: 119
<212> TYPE: DNA
<213> ORGANISM: Artificial Sequence
<220> FEATURE:
<223> OTHER INFORMATION: hXPO1 donor template

<400> SEQUENCE: 14
tgctttctgg aagtcaacat tttgatgttc ctcccaggag acagctgtat ttgactgtgt    60
tatcaaaggt aacagagcgg ttggttgagt gttcttcctg ttgcatactg tggttttga   119

<210> SEQ ID NO 15
<211> LENGTH: 119
<212> TYPE: DNA
<213> ORGANISM: Artificial Sequence
<220> FEATURE:
<223> OTHER INFORMATION: hXPO1 donor template

<400> SEQUENCE: 15
attctctaca tctgcgtctc cgttgctttc tggaagtcaa catttgatg ttcctcccag    60 gagacagctg tatttgaccg tgttatcaaa ggtaacagag cggttgcttg agtgttctt   119

<210> SEQ ID NO 16
<211> LENGTH: 25
<212> TYPE: DNA
<213> ORGANISM: Artificial Sequence
<220> FEATURE:
<223> OTHER INFORMATION: CCNT1 forward screening primer

<400> SEQUENCE: 16
tgagattaga agtaggcttg agagg    25

<210> SEQ ID NO 17
<211> LENGTH: 25
<212> TYPE: DNA
<213> ORGANISM: Artificial Sequence
<220> FEATURE:
<223> OTHER INFORMATION: CCNT1 reverse screening primer

<400> SEQUENCE: 17
gctaaattct cactagtccg atgac    25

<210> SEQ ID NO 18
<211> LENGTH: 25
<212> TYPE: DNA
<213> ORGANISM: Artificial Sequence
<220> FEATURE:
<223> OTHER INFORMATION: XPO1 forward screening primer

<400> SEQUENCE: 18
ttctctcctc tgtgatggta cattt    25

```
<210> SEQ ID NO 19
<211> LENGTH: 25
<212> TYPE: DNA
<213> ORGANISM: Artificial Sequence
<220> FEATURE:
<223> OTHER INFORMATION: XPO1 reverse screening primer

<400> SEQUENCE: 19
tcaagattgt agtgagctat gacca                                              25
```

GENETICALLY MODIFIED GENES AND CELLS, AND METHODS OF USING SAME FOR SILENCING VIRUS GENE EXPRESSION

STATEMENT REGARDING FEDERALLY SPONSORED RESEARCH

This invention was made with government support under AI110221 and AI143800 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. The ASCII copy, created on Sep. 4, 2019, is named USPTO-190905-Nonpro_Patent_App-P180284US02-SEQ_LIST.txt and is 65,821 bytes in size.

FIELD OF THE INVENTION

Methods and tools for autologous T cell transplant to introduce amino acid changes in CCNT1 and/or XPO1 that permanently suppress HIV-1 gene expression in patient cells, and other purposes.

BACKGROUND

The human immunodeficiency virus type 1 (HIV-1) is the causative agent of the acquired immunodeficiency syndromes (AIDS). HIV-1 infects more than 1 million people in the United States and more than 35 million worldwide, causing ~1 million deaths annually. While combined anti-retroviral therapy (cART) can reduce viral load and slow progression AIDS, there is no vaccine or cure for life-long, persistent infection.

Highly active anti-retroviral therapy (HAART) was a major breakthrough in the treatment of human immunodeficiency virus (HIV) infection as it can effectively reduce viral load and support regeneration of cellular immunity, thereby considerably prolonging survival of HIV-infected patients. However, despite the effective suppression of virus replication, HIV persists, integrated into the host genome, and rebounds as soon as treatment is interrupted or drug-resistant virus emerges. Even with the most effective antiviral drug combinations, it has not been possible to "cure" HIV infection, and life-long antiviral therapy is required to prevent progression of immunodeficiency. This vital long-term treatment is expensive and limited by drug toxicity and viral resistance, and the number of patients for whom HAART fails is increasing. Moreover, even prolonged periods of successful HAART have failed to restore HIV-specific immune responses. Thus, novel therapeutic approaches are still urgently required.

Several therapeutic strategies involving the transfer of antiviral genes have been developed for HIV-1 infection. In clinical trials, T cells and hematopoietic stem cells have been targeted. See Trickett et al. 2002 (Trickett A E, Kwan Y L, Cameron B, Dwyer J M. Ex vivo expansion of functional T lymphocytes from HIV-infected individuals. J Immunol Methods. 2002 Apr. 1; 262(1-2):71-83), Lieberman et al. 1997 (Lieberman J, Skolnik P R, Parkerson G R 3rd, Fabry J A, Landry B, Bethel J, Kagan J. Safety of autologous, ex vivo-expanded human immunodeficiency virus (HIV)-specific cytotoxic T-lymphocyte infusion in HIV-infected patients. Blood. 1997 Sep. 15; 90(6):2196-206), van Lunzen et al. 2007 (van Lunzen J, Glaunsinger T, Stahmer I, von Baehr V, Baum C, Schilz A, Kuehlcke K, Naundorf S, Martinius H, Hermann F, Giroglou T, Newrzela S, Muller I, Brauer F, Brandenburg G, Alexandrov A, von Laer D. Transfer of autologous gene-modified T cells in HIV-infected patients with advanced immunodeficiency and drug-resistant virus. Mol Ther. 2007 May; 15(5):1024-33), Tebas et al. 2014 (Tebas P, Stein D, Tang W W, Frank I, Wang S Q, Lee G, Spratt S K, Surosky R T, Giedlin M A, Nichol G, Holmes M C, Gregory P D, Ando D G, Kalos M, Collman R G, Binder-Scholl G, Plesa G, Hwang W T, Levine B L, June C H. Gene editing of CCR5 in autologous CD4 T cells of persons infected with HIV. N Engl J Med. 2014 Mar. 6; 370(10):901-10), von Laer et al. 2006, (von Laer, D, Hasselmann, S and Hasselmann, K (2006). Gene therapy for HIV infection: what does it need to make it work? J Gene Med 8: 658-667), and Levine et al. 2006 (Levine, B L, Humeau, L M, Boyer J, Macgregor, R R, Rebello, T, Lu, X et al. (2006). Additional strategies are needed.

SUMMARY OF THE INVENTION

The present invention builds on observations that rodents and their cells are refractory to HIV-1 infection, due to structural differences in the rodent proteins that render them incompatible for complexing with HIV-1 regulatory proteins. The human CCNT1 (hCCNT1) transcription factor is recruited by the HIV-1 Tat protein to activate robust viral mRNA transcription in human cells, but mouse CCNT1 (mCCNT1) interacts poorly with Tat due to a single amino acid difference: a tyrosine at mCCNT1 position 261 that is a cysteine in hCCNT1. The human XPO1 (hXPO1, aka CRM1) nuclear export receptor is recruited by the viral Rev protein to intron-retaining viral mRNAs in human cells to activate mRNAs nuclear export, but murine XPO1 (mXPO1) interacts poorly with Rev/RNA complexes, a defect that maps to a cluster of mXPO1 species-specific amino acids: threonine-411, valine-412, and serine-414.

The present invention relates to tools and methods for permanently suppressing HIV-1 gene expression in cells through surgical editing of cellular genes to express CCNT1 and/or XPO1 with refractory residues. One method is based on autologous cell transplant, in which cells are removed from a patient, modified (edited) in vitro, and returned to the patient, where they can outcompete the infected cells. The method can be performed with patient-derived primary CD4+ T cells, precursors thereof, hematopoietic stem or progenitor cells, or other types of cells. The native hCCNT1 and/or hXPO1 can be edited to express hCCNT1 with a C261Y substitution and/or hXPO1 with P411T, M412V, and/or F414S substitutions, respectively. These edits render the cells resistant to HIV-1 gene expression in vivo, thus providing an HIV-1 cure-targeted strategy. Editing multiple target genes in the same cells or cell lines (e.g., both hCCNT1 and hXPO1) inactivates multiple essential virus-host interactions with even greater suppression of viral replication and reduces the chances of developing resistance.

The genes can be edited using gene editing tools such as CRISPR/Cas9, TALENs, etc., thereby generating permanent, homozygous edits that are heritable and can be introduced in any cell type, including hematopoietic stem cells or their HIV-susceptible progeny cells (including but not limited to CD4+ T cells, macrophages, dendritic cells, and astrocytes). The edits have little to no discernible impact on the natural cellular functions of these proteins outside the context of infection. Thus, the strategy yields low to no cytotoxicity.

The mutations proposed also offer resistance to other viruses (e.g., in humans, primates, and other animals or mammals), since those host factors are relevant for other lentiviral pathogens including HIV-2 and simian immunodeficiency viruses (SIVs) commonly used for AIDS vaccine research in NHP models; and also deltaretroviruses such as human T lymphotropic virus type 1 (HTLV-1).

Figure 7:
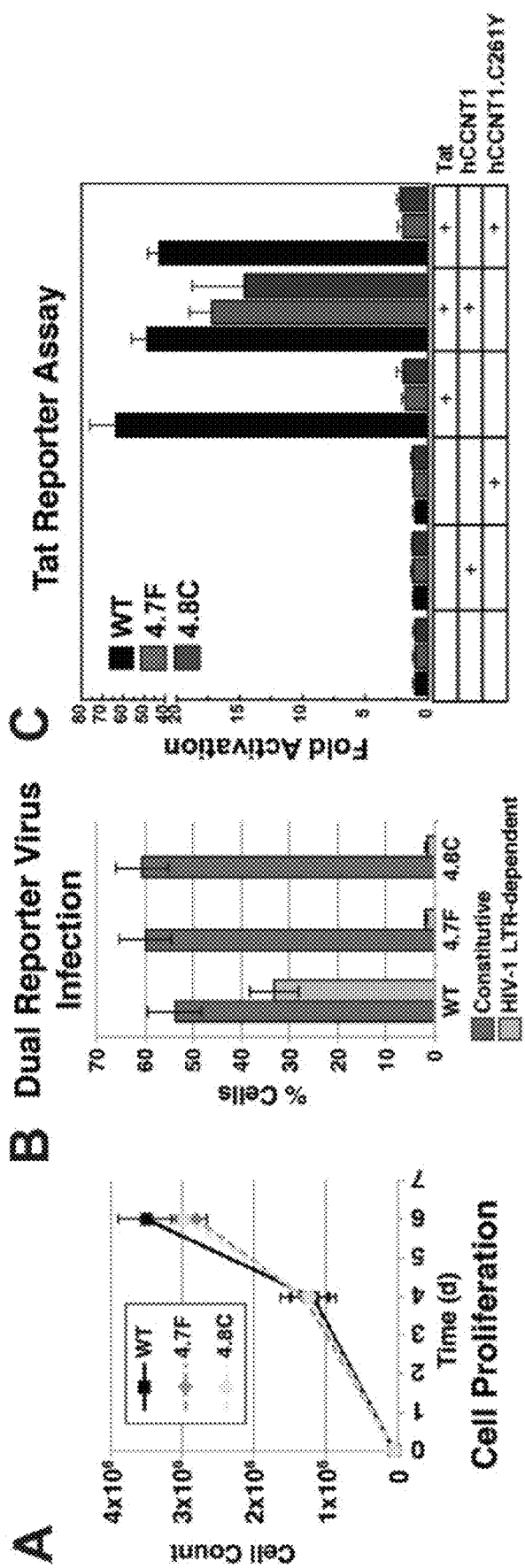
Figure 8:
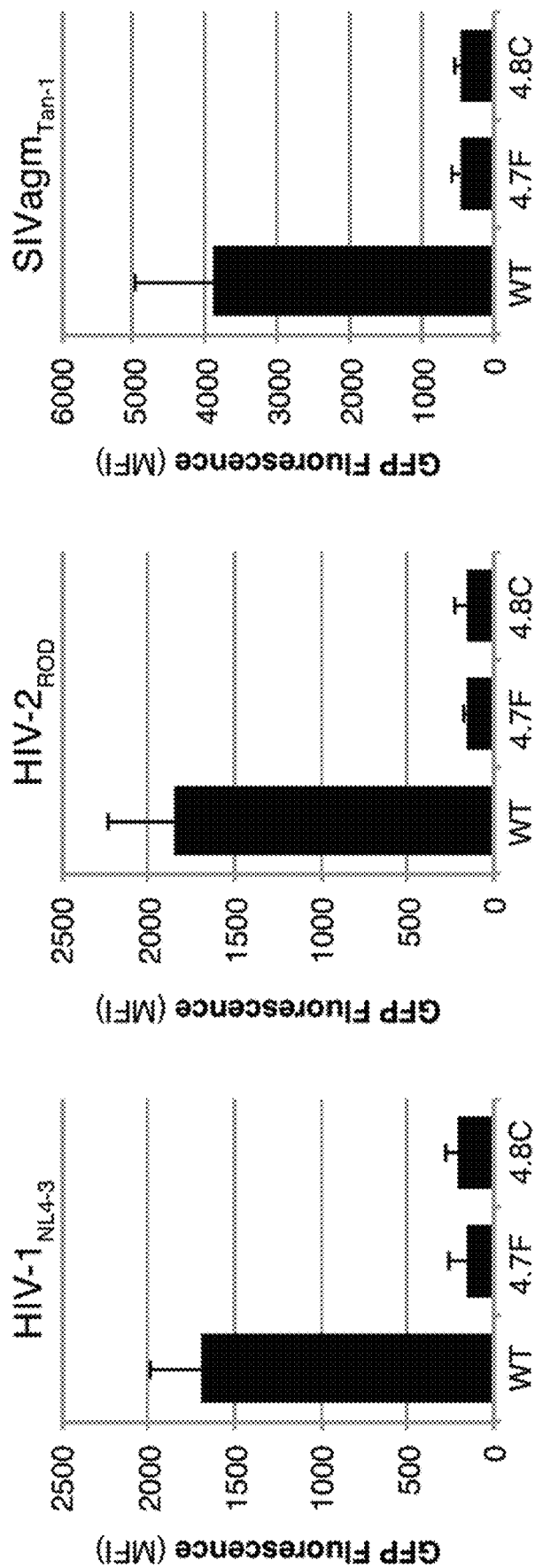
Figure 9A:
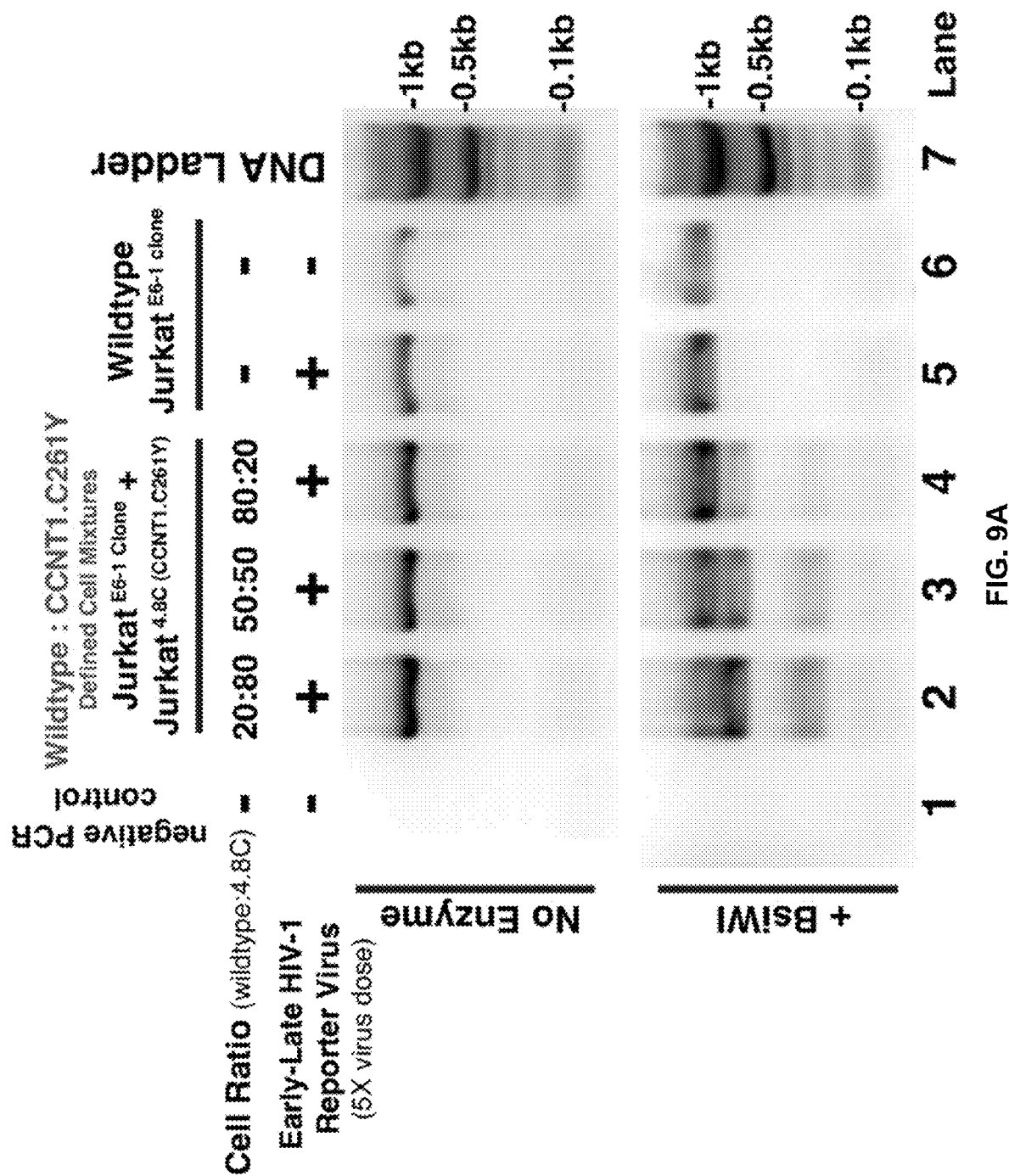
Figure 9B:
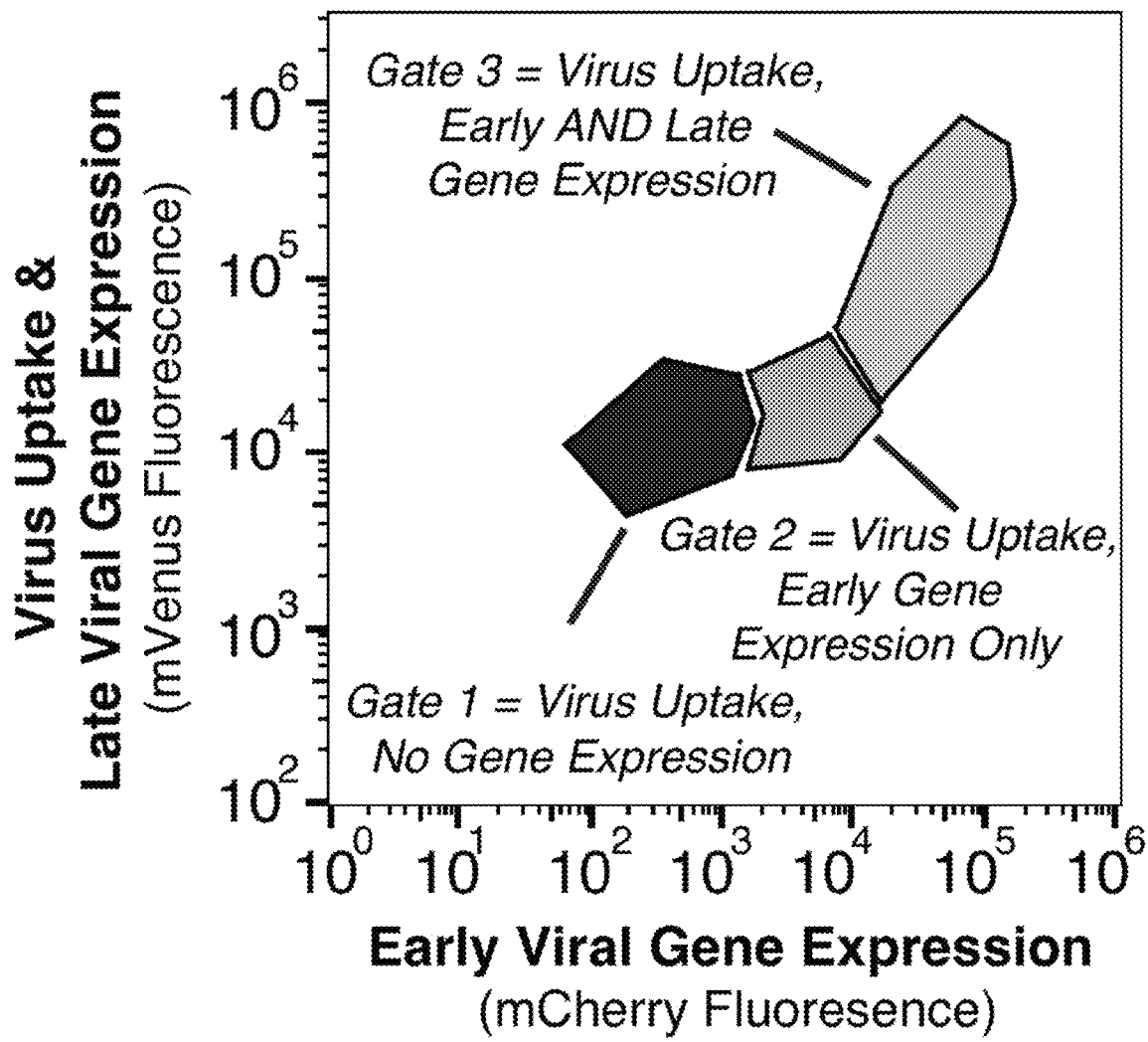
Figure 9C:
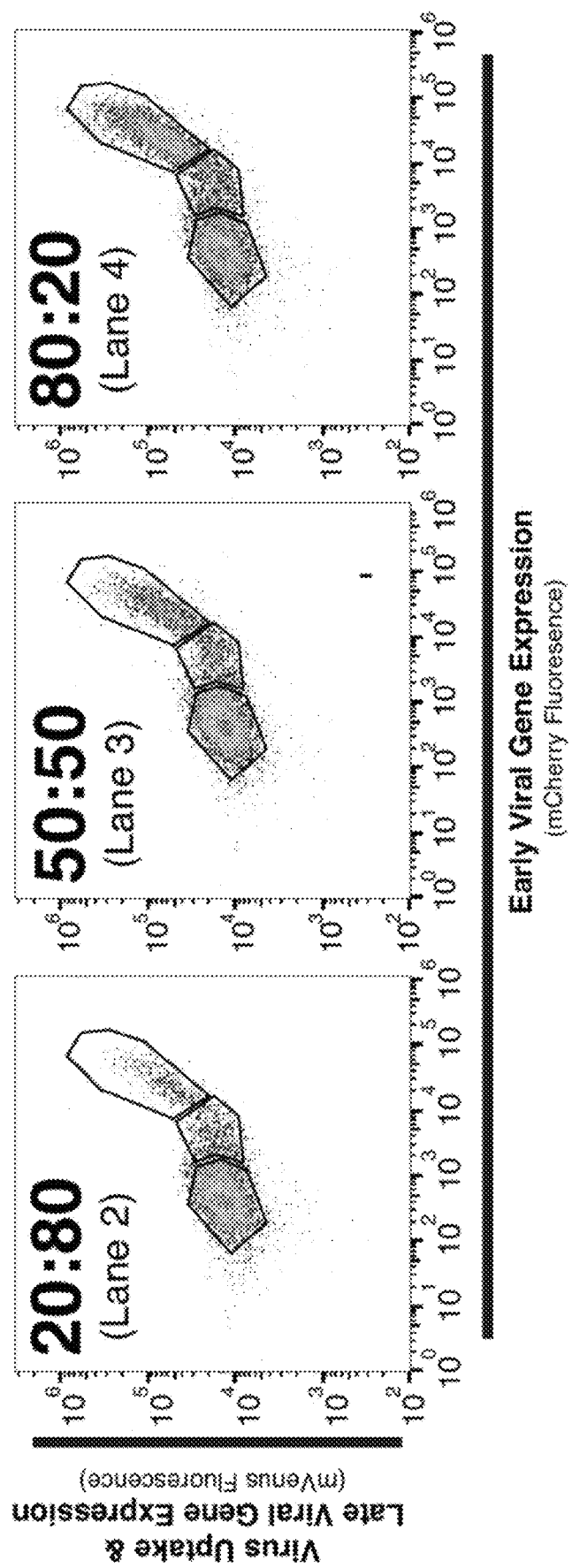
Figure 9D:
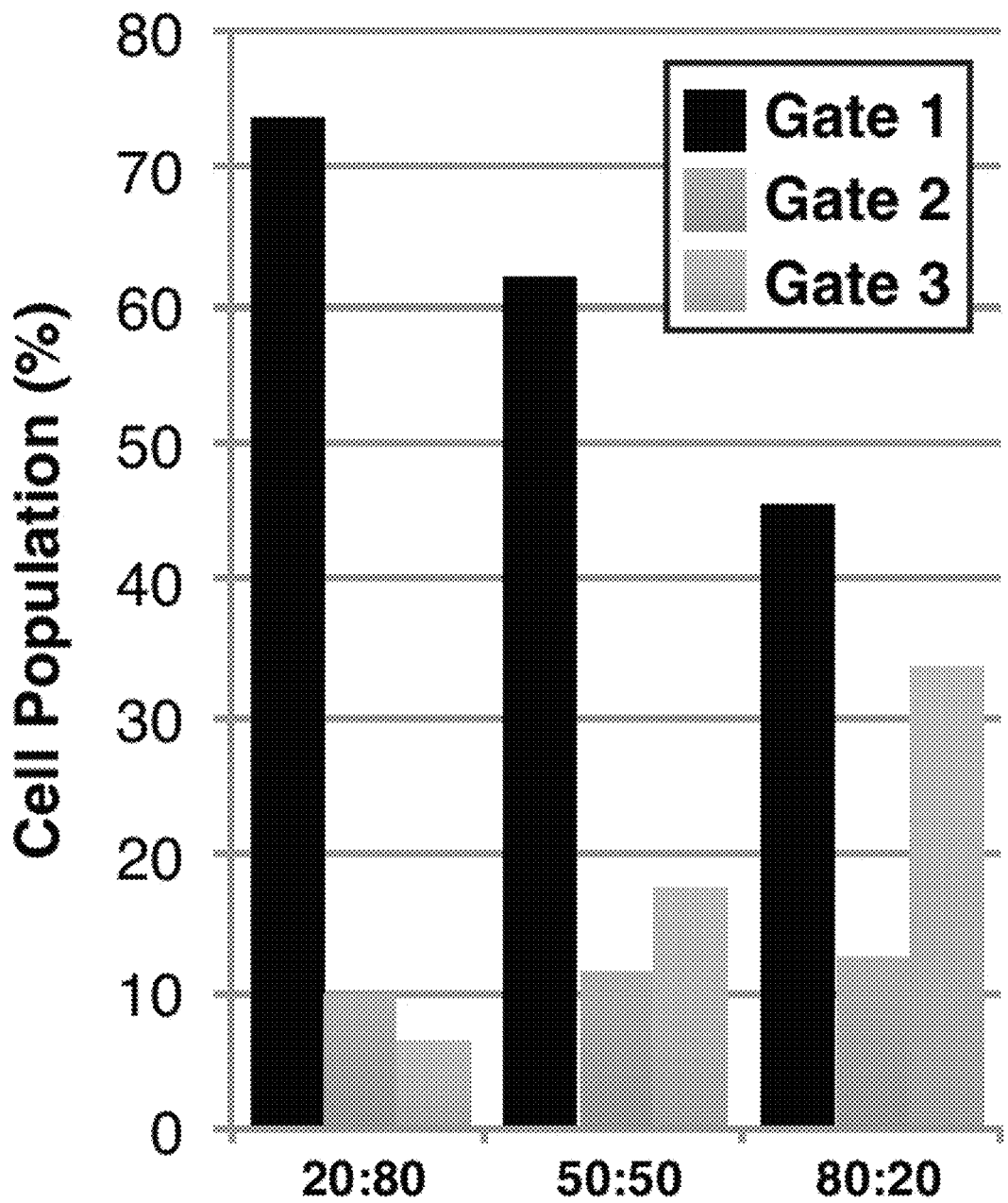

To date, there are no approved therapies for targeting HIV-1 following integration of the HIV-1 provirus (i.e., “after” infection). The present approach abolishes viral gene expression, virus particle production, and productive spread among cells, tissues, or people. Moreover, targeting species-specific protein features of CCNT1 or XPO1 is superior (i.e., less toxic) than other antiviral approaches that target virus-host interfaces because these particular protein features inhibit viral replication but do not play other essential roles in cell signaling.

The objects and advantages of the invention will appear more fully from the following detailed description of the preferred embodiment of the invention made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and 1B. An alignment of hCCNT1-C261Y (SEQ ID NO:1, shown as hCCNT1*), hCCNT1 (SEQ ID NO:3), and mCCNT1 (SEQ ID NO:6) as aligned by Clustal Omega (world wide web at ebi.ac.uk) (Sievers F, Wilm A, Dineen D, Gibson T J, Karplus K, Li W, Lopez R, McWilliam H, Remmert M, Riding J, Thompson J D, Higgins DG. Fast, scalable generation of high-quality protein multiple sequence alignments using Clustal Omega. Mol Syst Biol. 2011 Oct. 11; 7:539). An “*” (asterisk) indicates positions which have a single, fully conserved residue. A “:” (colon) indicates conservation between groups of strongly similar properties (scoring >0.5 in the Gonnet PAM 250 matrix). A “.” (period) indicates conservation between groups of weakly similar properties (scoring=<0.5 in the Gonnet PAM 250 matrix).

FIGS. 2A and 2B. An alignment of hXPO1-P411T-M412V-F414S (SEQ ID NO:7, shown as hXPO1*), hXPO1 (SEQ ID NO:9), and mXPO1 (SEQ ID NO:12) as aligned by Clustal Omega.

FIG. 3. Species-specific differences underpinning defects to HIV-1 Tat-CCNT1 and Rev-XPO1 interactions. (A) Summary of HIV-1's post-integration stages. (1) Host transcription factors activate low level HIV-1 transcription. (2) Early fully spiced viral mRNAs are translated to generate Tat and Rev. (3) Tat and Rev both translocate to the nucleus where Tat recruits pTEFb to upregulate transcriptional elongation and (4) Rev activates the nuclear export of late-stage, intron-retaining viral mRNAs and RNA genomes. (5) Full-length viral mRNAs are translated to generate Gag and Gag-Pol that encapsidate RNA genomes at virion assembly sites at the plasma membrane. B. Depiction of Tat (green) bound to CCNT1 (gold). In hCCNT1, C261 is thought to promote Tat activity by stabilizing a zinc bridge (purple). Figure based on PDB: 40R5. C. Depiction of XPO1 species-specific “patch” domain located between HEAT repeats 9 and 10. Mutation of hXPO1 T411, V412, and S414 to P411, M412, and F414 (as found in mXpo1) causes a reduction in Rev activity, potentially due to destabilization of a Rev-bound hXPO1 dimer.

FIG. 4. Editing of hCCNT1 using CRISPR-Cas9 to introduce C261Y substitution. The AGA TGC TAT TTG CTT CAT TGC AGG CAT GCG AGG CTG CCA AGA AA sequence corresponds to bases 688-731 of SEQ ID NO:5. The AGA TGC TAT TTG CTT CAT TGC AGG CgT aCG AaG CTG CCA AGA AA sequence corresponds to bases 35-78 of SEQ ID NO:13. The ACEAAKK sequence corresponds to residues 260-266 of SEQ ID NO:3. The AYEAAKK sequence corresponds to residues 260-266 of SEQ ID NO:1.

FIGS. 5A and 5B. Editing hXPO1 using CRISPR-Cas9 to introduce P411T, M412V, and F414S substitutions. The CAG CTA TAT TTG CCC ATG TTA TTC AAG GTA ACA GAG CGG TTG GTT sequence in FIG. 5A corresponds to bases 495-539 of SEQ ID NO:11. The CAG CTG TAT TTG ACT GTG TTA TCA AAG GTA ACA GAG CGG TTG GTT sequence in FIG. 5A corresponds to bases 42-86 of SEQ ID NO:14. The QLYLPMLFK sequence in FIG. 5A corresponds to residues 407-415 of SEQ ID NO:9. The QLYLTVLSK sequence in FIG. 5A corresponds to residues 407-415 of SEQ ID NO:7. The GCC TCT CCG TTG CTT TCT GGA AGT CAA sequence in FIG. 5B corresponds to bases 444-470 of SEQ ID NO:11. The CAG CTA TAT TTG CCC ATG TTA TTC AAG GTA ACA GAG CGG TTG GTT sequence in FIG. 5B corresponds to bases 495-539 of SEQ ID NO:11. The GCG TCT CCG TTG CTT TCT GGA AGT CAA sequence in FIG. 5B corresponds to bases 14-40 of SEQ ID NO:15. The CAG CTG TAT TTG ACC GTG TTA TCA AAG GTA ACA GAG CGG TTG CTT sequence in FIG. 5B corresponds to bases 65-109 of SEQ ID NO:15. The ASPLLSGSQ sequences in FIG. 5B correspond to residues 390-398 of each of SEQ ID NO:9 and SEQ ID NO:7. The QLYLPMLFK sequence in FIG. 5B corresponds to residues 407-415 of SEQ ID NO:9. The QLYLTVLSK sequence in FIG. 5B corresponds to residues 407-415 of SEQ ID NO:7.

FIG. 6. Stacking species-informed gene changes to block HIV-1 and other retroviruses. The approach modifies CCNT1 (C261Y) and XPO1 (edits P411T, M412V, F414S) either separately or in tandem to generate cells resistant to infection by HIV-1 and other retroviruses including HIV-2 and potentially HTLV.

FIG. 7. Human T cells can be rendered resistant to HIV-1 by modifying a single, species-specific hCCNT1 codon. A and B: Jurkat T cell lines bearing homozygous hCCNT1 alleles encoding the C261Y mutation (cell lines 4.7F and 4.8C) proliferate similarly to the parental cell line (A) but exhibit profound resistance to HIV-1 gene expression after infection with a dual fluorescent reporter virus expressing a constitutive (EF1a promoter-driven) RFP reporter (red, that confirms infection) and a Tat/LTR-driven GFP reporter (green) (B). C: Tat function is lost in hCCNT1-C261Y cells unless wild-type hCCNT1 is co-expressed in trans after transient transfection of these cells with plasmids encoding a Tat/LTR-driven firefly luciferase reporter with or without Tat and the indicated transgenes.

FIG. 8. Modified T cells exhibit broad-spectrum antiviral properties. Modified hCCNT1-C261Y cells (cell lines 4.7F and 4.8C) are refractory to HIV-2 and SIVagm gene expression.

FIGS. 9A-9D. Population-level analysis of HIV-1 resistance in heterogeneous cell mixtures. FIG. 9A: Genomic DNA analysis of prescribed mixtures of wild-type and modified hCCNT1-C261Y cells (cell line 4.8C). The relative abundance of hCCNT1-C261Y cells in each defined mixture (lanes 2, 3, and 4) is confirmed by polymerase chain reaction (PCR) targeting hCCNT1 genomic locus and subsequent DNA cleavage using BsiWI enzyme. BsiWI restriction enzyme sites are only present in DNA amplicons from hCCNT1-C261Y cells (compare lanes 5 and 6 to lanes 2, 3, and 4; also see FIG. 4 design scheme). FIG. 9B: Flow cytometric characterization of HIV-1 resistance. Using a HIV-1 reporter virus (encoding genes expressing mVenus and mCherry proteins) and the gating scheme shown, the number of infected cells exhibiting virus uptake (Gate 1, black), virus uptake with early gene expression only (Gate 2, orange), and virus uptake with early and late gene expression (Gate 3, gray) are quantified. FIGS. 9C and 9D: Flow cytometric analysis of defined mixtures of wild-type and modified hCCNT1-C261Y cells infected with a HIV-1 reporter virus. Example flow cytometry dot plots (FIG. 9C) and the percentage of infected cells present within each gate (FIG. 9D) are shown. Consistent with the previous data showing that hCCNT1-C261Y cells are resistant to both early and late HIV-1 gene expression (FIGS. 7B and 7C), cell mixtures containing a high abundance of hCCNT1-C261Y cells (e.g., 20:80, left panel) have a higher relative proportion of infected cells in Gate 1 (FIG. 9D, black bars). Conversely, cell mixtures containing a high abundance of wild-type cells (e.g., 80:20, right panel) have a higher relative proportion of infected cells in Gates 2 and 3 (FIG. 9D, orange and gray bars).

Figure 10A:
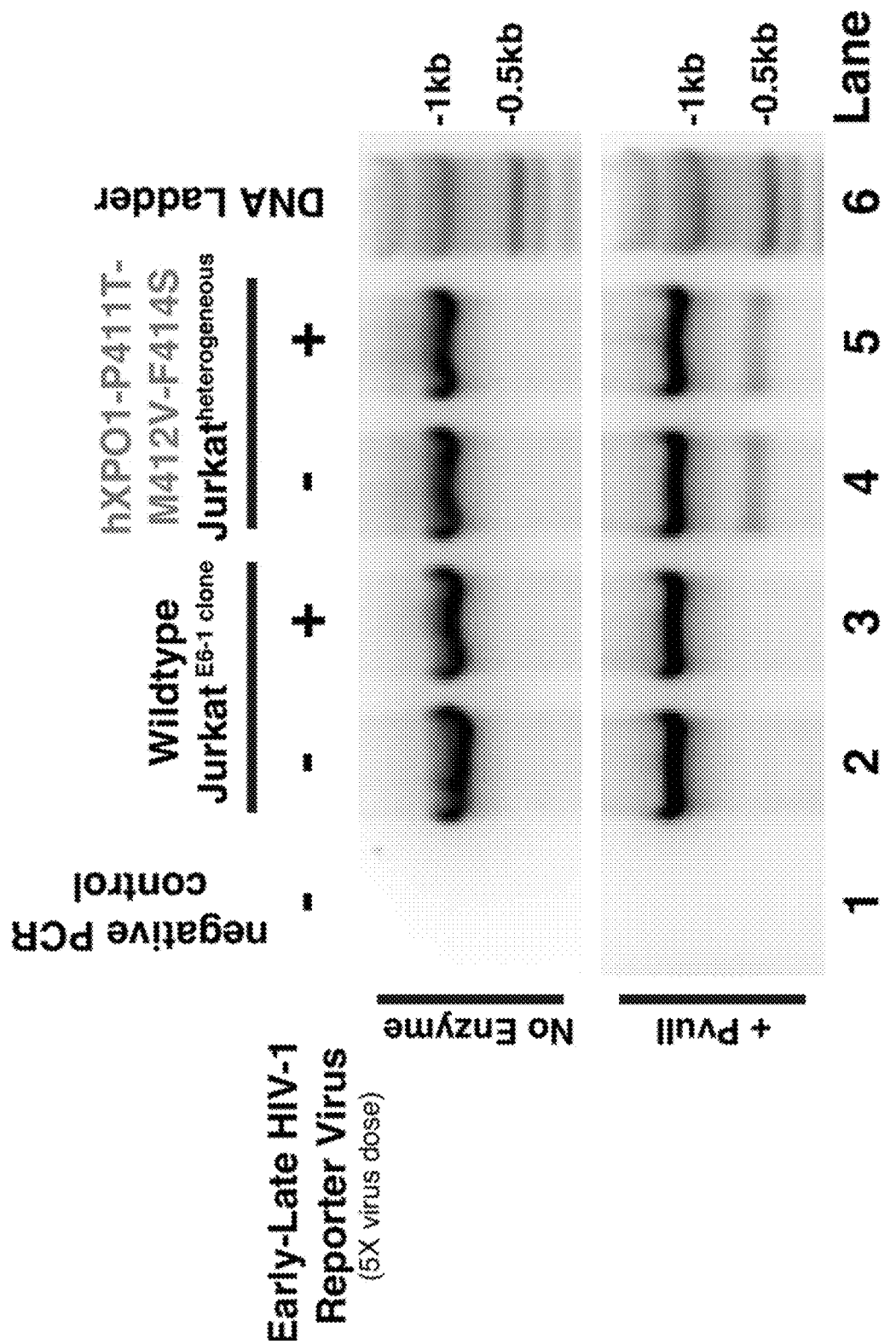
Figure 10B:
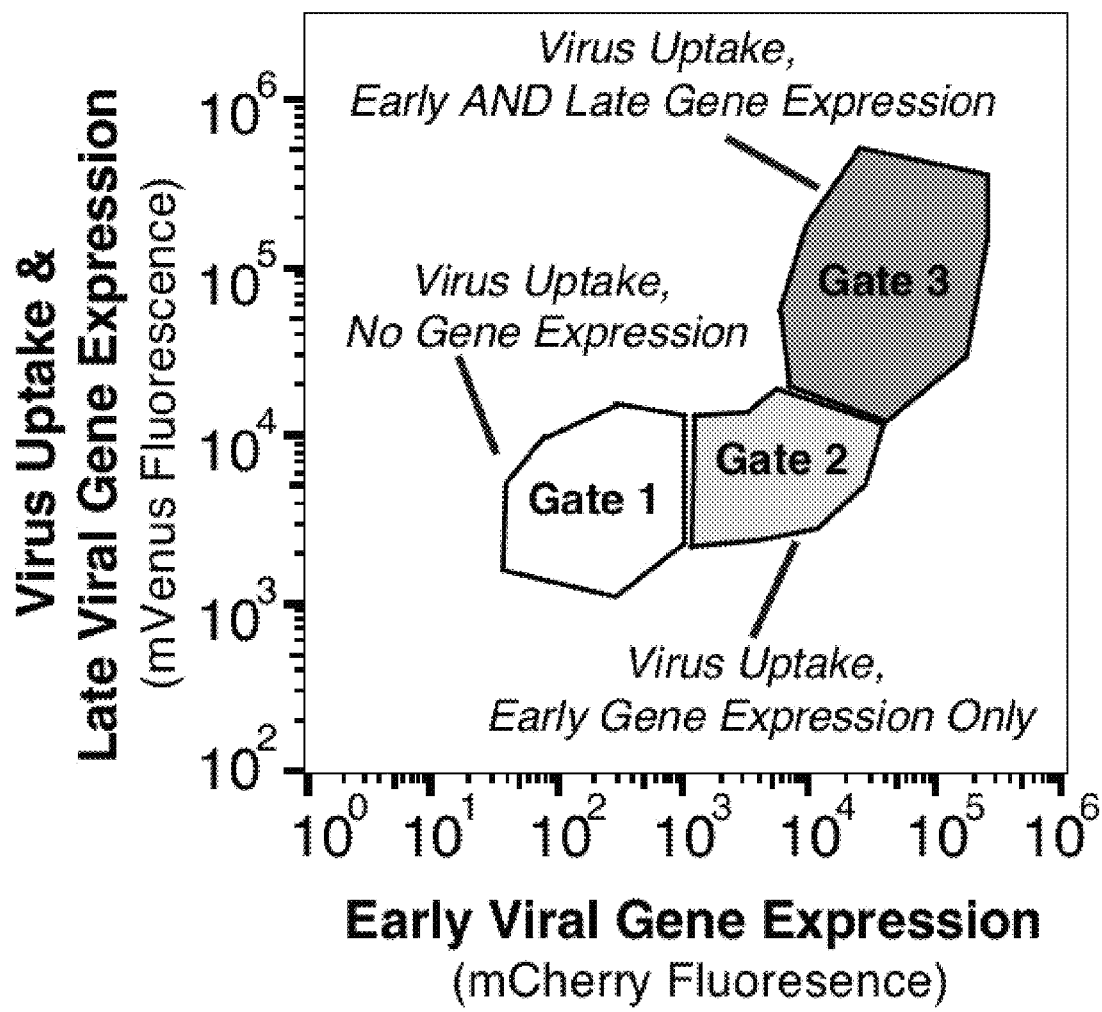
Figure 10C:
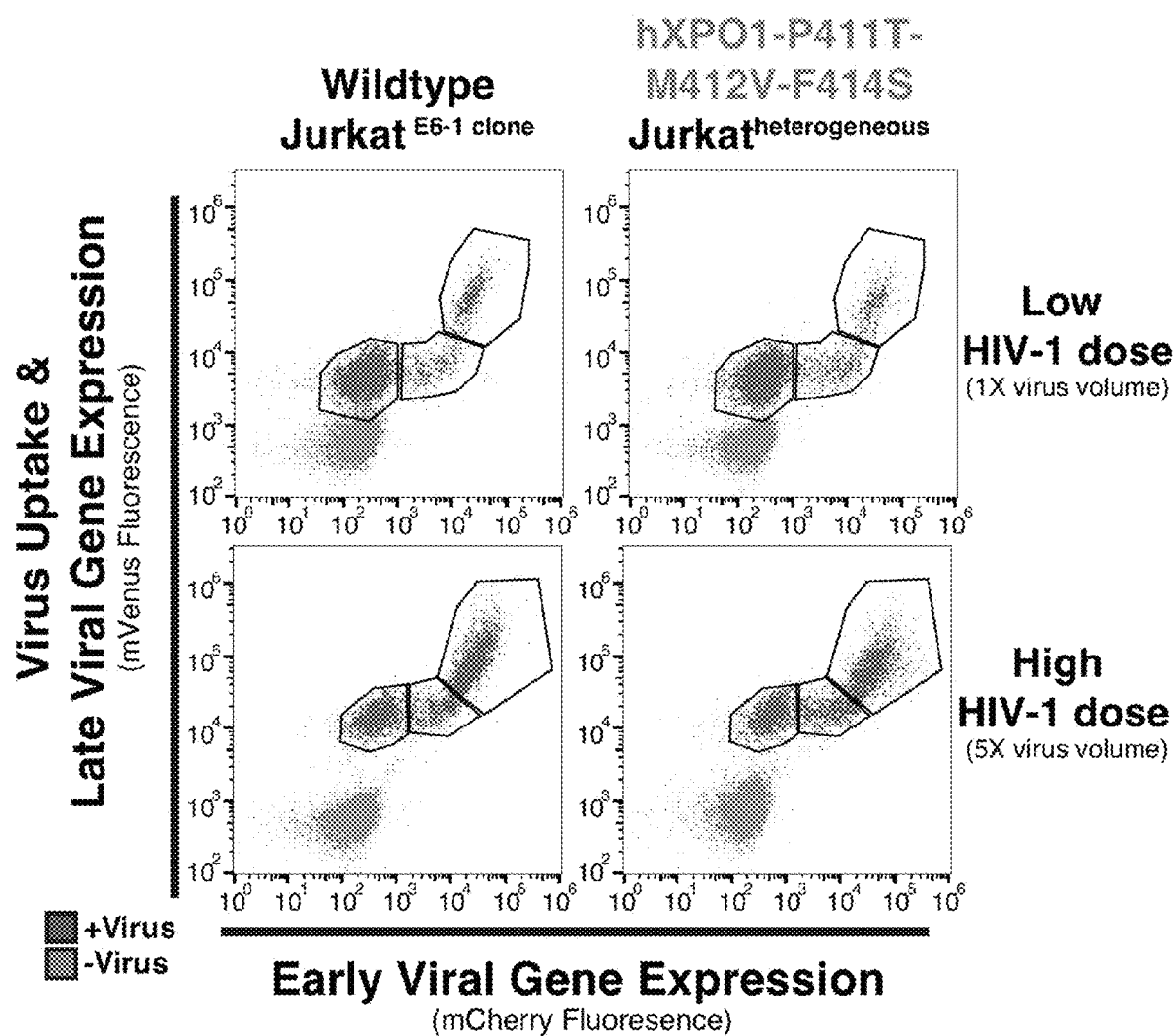
Figure 10D:
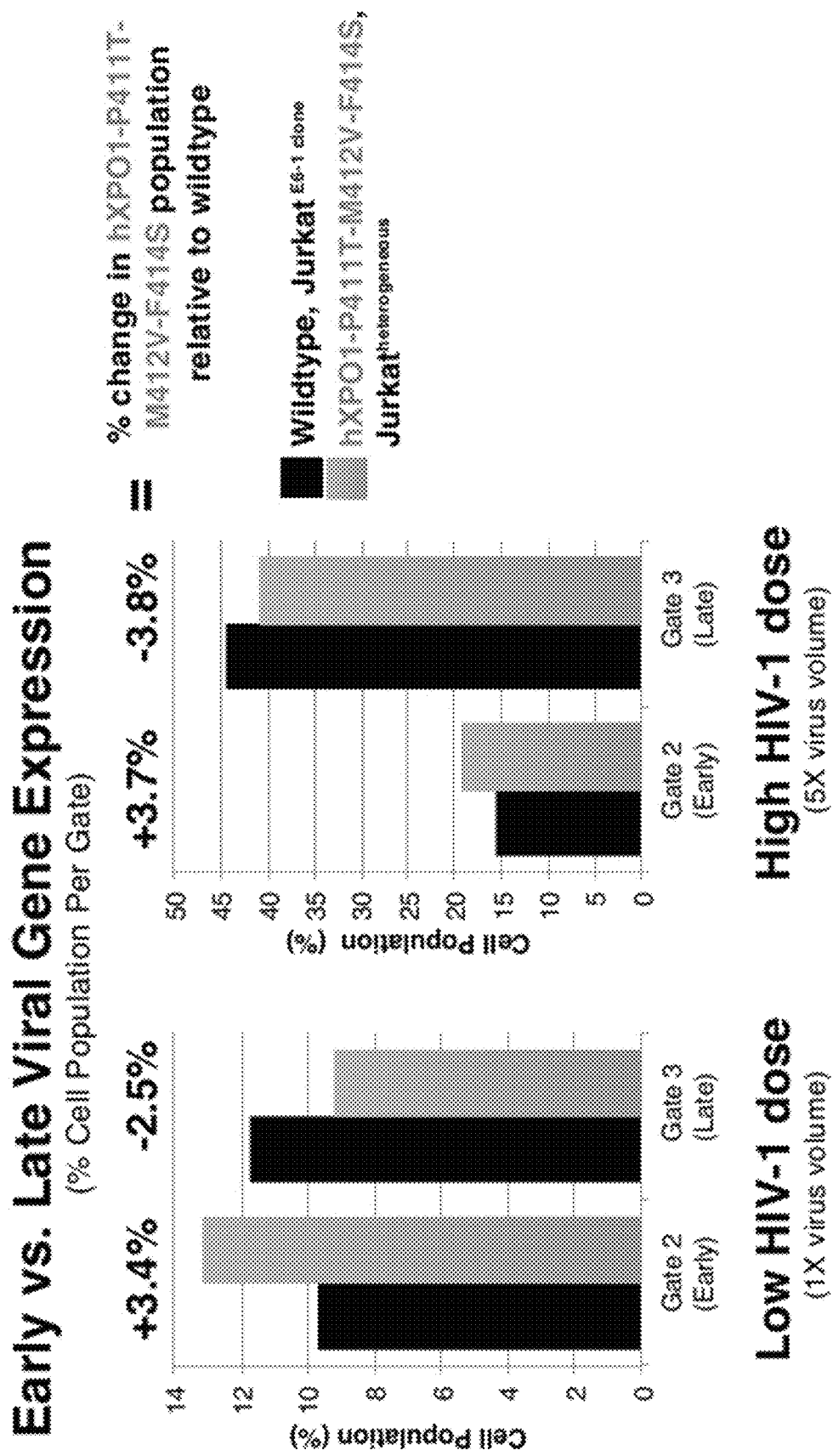

FIGS. 10A-10D. Human T cells treated to express hXPO1-P411T-M412V-F414S are refractory to viral late gene expression. FIG. 10A: Genomic DNA analysis of wild-type and heterogeneous, modified hXPO1-P411T-M412V-F414S cells. CRISPR-treated T cells exhibit detectable editing at XPO1 genomic locus in a subset of cells (0.97 kb DNA amplicons are digested by PvuII restriction enzyme and yield smaller ~0.49kb bands, lanes 4 and 5) but not in untreated, wild-type cells (lanes 2 and 3) (also see FIGS. 5A and/or 5B for design scheme). FIG. 10B: Flow cytometric characterization of HIV-1 resistance (as previously described in FIG. 9B). FIGS. 10C and 10D: Flow cytometric analysis of infected, heterogeneous human T cell populations treated to produce the hXPO1-P411T-M412V-F414S modification. Example flow cytometry dot plots (FIG. 10C) are shown, with uninfected control cell populations in blue and infected cell populations in red for both low (1×) and high (5×) HIV-1 reporter virus doses. The percentage of infected cells present within the early (Gate 2) and late (Gate 3) viral gene expression gates are shown (FIG. 10D) for each HIV-1 reporter virus dose. CRISPR-treated or wild-type control cells exhibiting early gene expression only or early and late gene expression were quantified (FIG. 10D, orange and black bars, respectively). At both infectious doses, treated cell populations had fewer cells expressing both early and late genes (late phase, gate 3) compared to the number of cells expressing only early genes (early phase, gate 2), consistent with a block to HIV-1 Rev function (i.e., the XPO1-mediated transition from early gene expression to early and late gene expression).

DETAILED DESCRIPTION OF THE INVENTION

Genetically Modified Genes

One aspect of the invention is a genetically modified CCNT1 gene. The genetically modified CCNT1 gene of the invention encodes a protein comprising a sequence with a sequence identity of at least about 80% with respect to SEQ ID NO:1 and includes a tyrosine at a position corresponding to position 261 of SEQ ID NO:1.

SEQ ID NO:1 represents hCCNT1-C261Y, which is a modified version of the human CCNT1 protein (hCCNT1, CCNT1, Cyclin-T1) comprising a substitution of a cysteine to a tyrosine at position 261 of hCCNT1 (C261Y). The genetically modified CCNT1 gene encoding SEQ ID NO:1 can be generated from the human CCNT1 gene encoding hCCNT1 by modifying the codon encoding the cysteine at position 261 in hCCNT1 to a codon encoding a tyrosine.

SEQ ID NO:1 is:

```
                                                (SEQ ID NO: 1)
MEGERKNNNKRWYFTREQLENSPSRRFGVDPDKELSYRQQAANLLQDMGQR

LNVSQLTINTAIVYMHRFYMIQSFTQFPGNSVAPAALFLAAKVEEQPKKLE

HVIKVAHTCLHPQESLPDTRSEAYLQQVQDLVILESIILQTLGFELTIDHP

HTHVVKCTQLVRASKDLAQTSYFMATNSLHLTTFSLQYTPPVVACVCIHLA

CKWSNWEIPVSTDGKHWWEYVDATVTLELLDELTHEFLQILEKTPNRLKRI

WNWRAYEAAKKTKADDRGTDEKTSEQTILNMISQSSSDTTIAGLMSMSTST

TSAVPSLPVSEESSSNLTSVEMLPGKRWLSSQPSFKLEPTQGHRTSENLAL

TGVDHSLPQDGSNAFISQKQNSKSVPSAKVSLKEYRAKHAEELAAQKRQLE

NMEANVKSQYAYAAQNLLSHHDSHSSVILKMPIEGSENPERPFLEKADKTA

LKMRIPVAGGDKAASSKPEEIKMRIKVHAAADKHNSVEDSVTKSREHKEKH

KTHPSNHHHHHNHHSHKHSHSQLPVGTGNKRPGDPKHSSQTSNLAHKTYSL

SSSFSSSSSTRKRGPSEETGGAVFDHPAKIAKSTKSSSLNFSFPSLPTMGQ

MPGHSSDTSGLSFSQPSCKTRVPHSKLDKGPTGANGHNTTQTIDYQDTVNM

LHSLLSAQGVQPTQPTAFEFVRPYSDYLNPRSGGISSRSGNTDKPRPPPLP

SEPPPPLPPLPK
```

An exemplary coding sequence encoding SEQ ID NO:1 is represented by SEQ ID NO:2:

```
                                                (SEQ ID NO: 2)
atggagggagagaggaagaacaacaacaaacggtggtatttcactcgagaa cagctggaaaatagcccatcccgtcgttttggcgtggacccagataaagaa ctttcttatcgccagcaggcggccaatctgcttcaggacatggggcagcgt cttaacgtctcacaattgactatcaacactgctatagtatacatgcatcga ttctacatgattcagtccttcacacagttccctggaaattctgtggctcca gcagccttgtttctagcagctaaagtggaggagcagcccaaaaaattggaa catgtcatcaaggtagcacatacttgtctccatcctcaggaatcccttcct gatactagaagtgaggcttatttgcaacaagttcaagatctggtcatttta gaaagcataattttgcagactttaggctttgaactaacaattgatcaccca catactcatgtagtaaagtgcactcaacttgttcgagcaagcaaggactta gcacagacttcttacttcatggcaaccaacagcctgcatttgaccacattt agcctgcagtacacacctcctgtggtggcctgtgtctgcattcacctggct tgcaagtggtccaattgggagatcccagtctcaactgacgggaagcactgg tgggagtatgttgacgccactgtgaccttggaacttttagatgaactgaca catgagtttctacagattttggagaaaactcccaacaggctcaaacgcatt
```

-continued
```
tggaattggagggcgtacgaagctgccaagaaaacaaaagcagatgaccga ggaacagatgaaaagacttcagagcagacaatcctcaatatgatttcccag agctcttcagacacaaccattgcaggtttaatgagcatgtcaacttctacc acaagtgcagtgccttccctgccagtctccgaagagtcatccagcaactta accagtgtggagatgttgccgggcaagcgttggctgtcctcccaaccttct ttcaaactagaacctactcagggtcatcggactagtgagaatttagcactt acaggagttgatcattccttaccacaggatggttcaaatgcatttatttcc cagaagcagaatagtaagagtgtgccatcagctaaagtgtcactgaaagaa taccgcgcgaagcatgcagaagaattggctgcccagaagaggcaactgag aacatggaagccaatgtgaagtcacaatatgcatatgctgcccagaatctc ctttctcatcatgatagccattcttcagtcattctaaaaatgcccatagag ggttcagaaaacccgagcggccttttctggaaaaggctgacaaaacagct ctcaaaatgagaatcccagtggcaggtggagataaagctgcgtcttcaaaa ccagaggagataaaaatgcgcataaaagtccatgctgcagctgataagcac aattctgtagaggacagtgttacaaagagccgagagcacaaagaaaagcac aagactcacccatctaatcatcatcatcataatcaccactcacacaag cactctcattcccaacttccagttggtactgggaacaaacgtcctggtgat ccaaaacatagtagccagacaagcaacttagcacataaaacctatagcttg tctagttcttttcctcttccagttctactcgtaaaaggggaccctctgaa gagactggagggctgtgtttgatcatccagccaagattgccaagagtact aaatcctcttccctaaatttctccttcccttcacttcctacaatgggtcag atgcctgggcatagctcagacacaagtggcctttccttttcacagcccagc tgtaaaactcgtgtccctcattcgaaactggataaagggccactggggcc aatggtcacaacacgacccagacaatagactatcaagacactgtgaatatg cttcactccctgctcagtgcccagggtgttcagcccactcagcctactgca tttgaatttgttcgtccttatagtgactatctgaatcctcggtctggtgga atctcctcgagatctggcaatacagacaaaccccggccaccacctctgcca tcagaacctcctccaccacttccaccccttcctaagtaa
```

The amino acid sequence of an exemplary hCCNT1 is represented by SEQ ID NO:3:

```
                                        (SEQ ID NO: 3)
MEGERKNNNKRWYFTREQLENSPSRRFGVDPDKELSYRQQAANLLQDMGQR

LNVSQLTINTAIVYMHRFYMIQSFTQFPGNSVAPAALFLAAKVEEQPKKLE

HVIKVAHTCLHPQESLPDTRSEAYLQQVQDLVILESIILQTLGFELTIDHP

HTHVVKCTQLVRASKDLAQTSYFMATNSLHLTTFSLQYTPPVVACVCIHLA

CKWSNWEIPVSTDGKHWWEYVDATVTLELLDELTHEFLQILEKTPNRLKRI

WNWRACEAAKKTKADDRGTDEKTSEQTILNMISQSSSDTTIAGLMSMSTST

TSAVPSLPVSEESSSNLTSVEMLPGKRWLSSQPSFKLEPTQGHRTSENLAL

TGVDHSLPQDGSNAFISQKQNSKSVPSAKVSLKEYRAKHAEELAAQKRQLE

NMEANVKSQYAYAAQNLLSHHDSHSSVILKMPIEGSENPERPFLEKADKTA
```

-continued
```
LKMRIPVAGGDKAASSKPEEIKMRIKVHAAADKHNSVEDSVTKSREHKEKH

KTHPSNHHHHHNHHSHKHSHSQLPVGTGNKRPGDPKHSSQTSNLAHKTYSL

SSSFSSSSSTRKRGPSEETGGAVFDHPAKIAKSTKSSSLNFSFPSLPTMGQ

MPGHSSDTSGLSFSQPSCKTRVPHSKLDKGPTGANGHNTTQTIDYQDTVNM

LHSLLSAQGVQPTQPTAFEFVRPYSDYLNPRSGGISSRSGNTDKPRPPPLP

SEPPPPLPPLPK
```

Various isoforms or variants of hCCNT1 include modifications to SEQ ID NO:3 in which positions 181-184 include a sequence or arginine-threonine-aspartic acid-threonine (RTDT) in place of serine-leucine-histidine-leucine (SLHL), position 77 includes arginine (R) in place of glutamine (Q), position 362 includes arginine (R) in place of histidine (H), and/or position 541 includes cysteine (C) in place of arginine (R). Any of these modifications can be included in the protein encoded by the genetically modified CCNT1 gene of the invention.

A coding sequence of the exemplary hCCNT1 is represented by SEQ ID NO:4:

```
                                         (SEQ ID NO: 4)
atggagggagagaggaagaacaacaacaaacggtggtatttcactcgagaa cagctggaaaatagcccatcccgtcgttttggcgtggacccagataaagaa ctttcttatcgccagcaggcggccaatctgcttcaggacatggggcagcgt cttaacgtctcacaattgactatcaacactgctatagtatacatgcatcga ttctacatgattcagtccttcacacagttccctggaaattctgtggctcca gcagccttgtttctagcagctaaagtggaggagcagcccaaaaaattggaa catgtcatcaaggtagcacatacttgtctccatcctcaggaatcccttcct gatactagaagtgaggcttatttgcaacaagttcaagatctggtcatttta gaaagcataattttgcagactttaggctttgaactaacaattgatcaccca catactcatgtagtaaagtgcactcaacttgttcgagcaagcaaggactta gcacagacttcttacttcatggcaaccaacagcctgcatttgaccacattt agcctgcagtacacacctcctgtggtggcctgtgtctgcattcacctggct tgcaagtggtccaattgggagatcccagtctcaactgacgggaagcactgg tgggagtatgttgacgccactgtgaccttggaacttttagatgaactgaca catgagtttctacagattttggagaaaactcccaacaggctcaaacgcatt tggaattggagggcatgcgaggctgccaagaaaacaaaagcagatgaccga ggaacagatgaaaagacttcagagcagacaatcctcaatatgatttcccag agctcttcagacacaaccattgcaggtttaatgagcatgtcaacttctacc acaagtgcagtgccttccctgccagtctccgaagagtcatccagcaactta accagtgtggagatgttgccgggcaagcgttggctgtcctcccaaccttct ttcaaactagaacctactcagggtcatcggactagtgagaatttagcactt acaggagttgatcattccttaccacaggatggttcaaatgcatttatttcc cagaagcagaatagtaagagtgtgccatcagctaaagtgtcactgaaagaa taccgcgcgaagcatgcagaagaattggctgcccagaagaggcaactgag aacatggaagccaatgtgaagtcacaatatgcatatgctgcccagaatctc ctttctcatcatgatagccattcttcagtcattctaaaaatgcccatagag
```

-continued

```
ggttcagaaaaccccgagcggccttttctggaaaaggctgacaaaacagct ctcaaaatgagaatcccagtggcaggtggagataaagctgcgtcttcaaaa ccagaggagataaaaatgcgcataaaagtccatgctgcagctgataagcac aattctgtagaggacagtgttacaaagagccgagagcacaagaaaagcac aagactcacccatctaatcatcatcatcataatcaccactcacacaag cactctcattcccaacttccagttggtactgggaacaaacgtcctggtgat ccaaaacatagtagccagacaagcaacttagcacataaaacctatagcttg tctagttcttttcctcttccagttctactcgtaaaaggggaccctctgaa gagactggaggggctgtgtttgatcatccagccaagattgccaagagtact aaatcctcttccctaaatttctccttcccttcacttcctacaatgggtcag atgcctgggcatagctcagacacaagtggcctttccttttcacagcccagc tgtaaaactcgtgtccctcattcgaaactggataaagggcccactggggcc aatggtcacaacacgacccagacaatagactatcaagacactgtgaatatg cttcactccctgctcagtgcccagggtgttcagcccactcagcctactgca tttgaatttgttcgtccttatagtgactatctgaatcctcggtctggtgga atctcctcgagatctggcaatacagacaaaccccggccaccacctctgcca tcagaacctcctccaccacttccacccctcctaagtaa
```

The sequence of a portion of an exemplary human CCNT1 gene that can be edited to generate an exemplary modified CCNT1 gene is represented by SEQ ID NO:5:

```
                                       (SEQ ID NO: 5)
TGAGATTAGAAGTAGGCTTGAGAGGCCGGGCATGGTGGCTCATGCCTGTAG

TCCCAGCACTTTGGGAGGCCAAGGCAGGCGGATCAACTGAGGTCAGGAGTT

CGAGACCAGCCTGGCCAACATGGTGAAACCTCGTCTCTACTAAAAATACAA

AAATTAGCCAGGCATGGTGATGCACACCTGTAGTTCCAGCTACTTGGGAGG

CTGAGACAGGAGAATCGCTTGAACTCGGGACGTTAGGTTGCAGTGAGCCGA

GATTGTGCCACTGCACTCCAGCCTGGATGACAAAGTGAGACTCTGTCTCAA

ACAAACAAACAAACAAAAAACAACAGTAACAACAAAAAAGAAGTAGGCTTG

AGAGCACATCTTTTACTTTAGCATAAAACCTCACCAAAATTTCTAGAACTC

AGTTATGGACTAACTATAATCATAAGCGAAGGCATGGATGTTCATGTATGA

ATTTTAGATAAGCATAGATTCTTTGTTGTTATTATTGCTTTGTAACGTTTG

GATAGATTGCTGTGACTCTTAATTGAAGGTTTTAAAATCTTCTCTTGATGG

TAATATTTATTGGATTACATGTTAGGATAGCCTCCTGCCTGTGGCCTATCC

AGAACTTCCAGTGTTGCTGCAAGTACAATCTACTCATCTCAGTGTTTTTTT

ATTTAGTAAATTACCTAAGTAAAGAGATGCTATTTGCTTCATTGCAGGCAT

GCGAGGCTGCCAAGAAAACAAAAGCAGATGACCGAGGAACAGATGAAAAGA

CTTCAGAGCAGACAATCCTCAATATGATTTCCCAGAGCTCTTCAGACACAA

CCATTGCAGGTTTAATGAGCATGTCAACTTCTACCACAAGTGCAGTGCCTT

CCCTGCCAGTCTCCGAAGAGTCATCCAGCAACTTAACCAGTGTGGAGATGT

TGCCGGGCAAGCGTTGGCTGTCCTCCCAACCTTCTTTCAAACTAGAACCTA

CTCAGGGTCATCGGACTAGTGAGAATTTAGC
```

Exemplary methods for performing the editing are described in the following examples.

The tyrosine at position 261 of the protein encoded by the genetically modified CCNT1 gene of the invention is modeled after the tyrosine at position 261 of the mouse CCNT1 protein (mCCNT1, Ccnt1), which is represented by SEQ ID NO:6:

```
                                              (SEQ ID NO: 6)
MEGERKNNNKRWYFTREQLENSPSRRFGVDSDKELSYRQQAANLLQDMGQR

LNVSQLTINTAIVYMHRFYMIQSFTQFHRYSMAPAALFLAAKVEEQPKKLE

HVIKVAHTCLHPQESLPDTRSEAYLQQVQDLVILESIILQTLGFELTIDHP

HTHVVKCTQLVRASKDLAQTSYFMATNSLHLTTFSLQYTPPVVACVCIHLA

CKWSNWEIPVSTDGKHWWEYVDATVTLELLDELTHEFLQILEKTPSRLKRI

RNWRAYQAAMKTKPDDRGADENTSEQTILNMISQTSSDTTIAGLMSMSTAS

TSAVPSLPSSEESSSSLTSVDMLQGERWLSSQPPPFKLEAAQGHRTSESLAL

IGVDHSLQQDGSSAFGSQKQASKSVPSAKVSLKEYRAKHAEELAAQKRQLE

NMEANVKSQYAYAAQNLLSHDSHSSVILKMPIESSENPERPFLDKADKSAL

KMRLPVASGDKAVSSKPEEIKMRIKVHSAGDKHNSIEDSVTKSREHKEKQR

THPSNHHHHNHHSHRHSHLQLPAGPVSKRPSDPKHSSQTSTLAHKTYSLS

STLSSSSSTRKRGPPEETGAAVFDHPAKIAKSTKSSLNFPFPPLPTMTQLP

GHSSDTSGLPFSQPSCKTRVPHMKLDKGPPGANGHNATQSIDYQDTVNMLH

SLLSAQGVQPTQAPAFEFVHSYGEYMNPRAGAISSRSGTTDKPRPPPLPSE

PPPPLPPLPK
```

An alignment of hCCNT1-C261Y (SEQ ID NO:1, shown as hCCNT1*), hCCNT1 (SEQ ID NO:3), and mCCNT1 (SEQ ID NO:6) as aligned by Clustal Omega using default parameters is shown in FIGS. 1A and 1B.

With the exception of Y261, the genetically modified CCNT1 gene may encode a number of differences with respect to mCCNT1 or native CCNT1 proteins. These differences may comprise at least one, some, or all of: an amino acid other than glutamic acid at a position corresponding to position 3 of SEQ ID NO:1; an amino acid other than leucine at a position corresponding to position 29 of SEQ ID NO:1; an amino acid other than serine at a position corresponding to position 31 of SEQ ID NO:1; an amino acid other than leucine and/or asparagine at a position corresponding to position 37 of SEQ ID NO:1; an amino acid other than histidine at a position corresponding to position 79 of SEQ ID NO:1; an amino acid other than arginine and glutamine and/or tyrosine at a position corresponding to position 80 of SEQ ID NO:1; an amino acid other than tyrosine at a position corresponding to position 81 of SEQ ID NO:1; an amino acid other than methionine at a position corresponding to position 83 of SEQ ID NO:1; an amino acid other than alanine at a position corresponding to position 110 of SEQ ID NO:1; an amino acid other than tyrosine at a position corresponding to position 113 of SEQ ID NO:1; an amino acid other than serine at a position corresponding to position 250 of SEQ ID NO:1; an amino acid other than arginine at a position corresponding to position 256 of SEQ ID NO:1; an amino acid other than glutamine at a position corresponding to position 262 of SEQ ID NO:1; an amino acid other than methionine, arginine, and/or glutamine at a position corresponding to position 265 of SEQ ID NO:1; an amino acid other than proline at a position corresponding to position 269 of SEQ ID NO:1; an amino acid other than alanine at a position corresponding to position 274 of SEQ ID NO:1; an amino acid other than threonine and/or alanine at a position corresponding to position 276 of SEQ ID NO:1; an amino acid other than asparagine at a position corresponding to position 277 of SEQ ID NO:1; an amino acid other than threonine at a position corresponding to position 290 of SEQ ID NO:1; an amino acid other than alanine at a position corresponding to position 304 of SEQ ID NO:1; an amino acid other than alanine and/or threonine at a position corresponding to position 305 of SEQ ID NO:1; an amino acid other than serine at a position corresponding to position 306 of SEQ ID NO:1; an amino acid other than alanine at a position corresponding to position 307 of SEQ ID NO:1; an amino acid other than arginine and/or valine at a position corresponding to position 313 of SEQ ID NO:1; an amino acid other than serine, alanine, and/or valine at a position corresponding to position 315 of SEQ ID NO:1; an amino acid other than serine at a position corresponding to position 322 of SEQ ID NO:1; an amino acid other than asparagine at a position corresponding to position 325 of SEQ ID NO:1; an amino acid other than aspartic acid at a position corresponding to position 327 of SEQ ID NO:1; an amino acid other than glutamine at a position corresponding to position 330 of SEQ ID NO:1; an amino acid other than glutamic acid at a position corresponding to position 332 of SEQ ID NO:1; an amino acid other than proline at a position corresponding to position 340 of SEQ ID NO:1; an amino acid other than alanine at a position corresponding to position 345 of SEQ ID NO:1; an amino acid other than alanine at a position corresponding to position 346 of SEQ ID NO:1; an amino acid other than serine at a position corresponding to position 354 of SEQ ID NO:1; an amino acid other than isoleucine and/or methionine at a position corresponding to position 358 of SEQ ID NO:1; an amino acid other than glutamine at a position corresponding to position 365 of SEQ ID NO:1; an amino acid other than serine at a position corresponding to position 370 of SEQ ID NO:1; an amino acid other than glycine at a position corresponding to position 373 of SEQ ID NO:1; an amino acid other than alanine at a position corresponding to position 378 of SEQ ID NO:1; an amino acid other than serine at a position corresponding to position 443 of SEQ ID NO:1; an amino acid other than aspartic acid at a position corresponding to position 453 of SEQ ID NO:1; an amino acid other than serine and/or alanine at a position corresponding to position 458 of SEQ ID NO:1; an amino acid other than leucine at a position corresponding to position 464 of SEQ ID NO:1; an amino acid other than serine at a position corresponding to position 468 of SEQ ID NO:1; an amino acid other than valine at a position corresponding to position 473 of SEQ ID NO:1; an amino acid other than serine at a position corresponding to position 488 of SEQ ID NO:1; an amino acid other than glycine at a position corresponding to position 490 of SEQ ID NO:1; an amino acid other than isoleucine at a position corresponding to position 496 of SEQ ID NO:1; an amino acid other than glutamine at a position corresponding to position 510 of SEQ ID NO:1; an amino acid other than arginine at a position corresponding to position 511 of SEQ ID NO:1; an amino acid other than arginine at a position corresponding to position 527 of SEQ ID NO:1; an amino acid other than leucine at a position corresponding to position 531 of SEQ ID NO:1; an amino acid other than alanine at a position corresponding to position 535 of SEQ ID NO:1; an amino acid other than proline at a position corresponding to position 537 of SEQ ID NO:1; an amino acid other than valine at a position corresponding to position 538 of SEQ ID NO:1; an amino acid other than serine at a position corresponding to position 539 of SEQ ID NO:1; an amino acid other than serine at a position corresponding to position 543 of SEQ ID NO:1; an amino acid other than threonine at a position corresponding to position 553 of SEQ ID NO:1; an amino acid other than threonine at a position corresponding to position 564 of SEQ ID NO:1; an amino acid other than leucine at a position corresponding to position 565 of SEQ ID NO:1; an amino acid other than proline at a position corresponding to position 577 of SEQ ID NO:1; an amino acid other than alanine at a position corresponding to position 582 of SEQ ID NO:1; an amino acid other than proline at a position corresponding to position 603 of SEQ ID NO:1; an amino acid other than proline at a position corresponding to position 606 of SEQ ID NO:1; an amino acid other than threonine and/or alanine at a position corresponding to position 611 of SEQ ID NO:1; an amino acid other than leucine at a position corresponding to position 613 of SEQ ID NO:1; an amino acid other than proline at a position corresponding to position 624 of SEQ ID NO:1; an amino acid other than methionine at a position corresponding to position 637 of SEQ ID NO:1; an amino acid other than proline at a position corresponding to position 644 of SEQ ID NO:1; an amino acid other than alanine at a position corresponding to position 651 of SEQ ID NO:1; an amino acid other than serine at a position corresponding to position 654 of SEQ ID NO:1; an amino acid other than alanine at a position corresponding to position 678 of SEQ ID NO:1; an amino acid other than proline at a position corresponding to position 679 of SEQ ID NO:1; an amino acid other than aspartic acid at a position corresponding to position 682 of SEQ ID NO:1; an amino acid other than histidine at a position corresponding to position 685 of SEQ ID NO:1; an amino acid other than serine at a position corresponding to position 686 of SEQ ID NO:1; an amino acid other than glycine at a position corresponding to position 688 of SEQ ID NO:1; an amino acid other than glutamic acid at a position corresponding to position 689 of SEQ ID NO:1; an amino acid other than methionine at a position corresponding to position 691 of SEQ ID NO:1; an amino acid other than alanine at a position corresponding to position 695 of SEQ ID NO:1; an amino acid other than alanine at a position corresponding to position 697 of SEQ ID NO:1; an amino acid other than methionine at a position corresponding to position 698 of SEQ ID NO:1; an amino acid other than threonine at a position corresponding to position 704 of SEQ ID NO:1; and an amino acid other than leucine at a position corresponding to position 710 of SEQ ID NO:1.

In some versions, the differences encoded by the genetically modified CCNT1 gene with respect to mCCNT1 or other native CCNT1 proteins may comprise at least one, some, or all of: proline at a position corresponding to position 31 of SEQ ID NO:1; tyrosine at a position corresponding to position 37 of SEQ ID NO:1; proline at a position corresponding to position 79 of SEQ ID NO:1; glycine at a position corresponding to position 80 of SEQ ID NO:1; asparagine at a position corresponding to position 81 of SEQ ID NO:1; valine at a position corresponding to position 83 of SEQ ID NO:1; threonine at a position corresponding to position 110 of SEQ ID NO:1; asparagine at a position corresponding to position 250 of SEQ ID NO:1; tryptophan at a position corresponding to position 256 of SEQ ID NO:1; glutamic acid at a position corresponding to position 262 of SEQ ID NO:1; lysine at a position corresponding to position 265 of SEQ ID NO:1; alanine at a position corresponding to position 269 of SEQ ID NO:1;

threonine at a position corresponding to position 274 of SEQ ID NO:1; lysine at a position corresponding to position 277 of SEQ ID NO:1; serine at a position corresponding to position 290 of SEQ ID NO:1; serine at a position corresponding to position 305 of SEQ ID NO:1; threonine at a position corresponding to position 306 of SEQ ID NO:1; threonine at a position corresponding to position 307 of SEQ ID NO:1; leucine at a position corresponding to position 313 of SEQ ID NO:1; valine at a position corresponding to position 315 of SEQ ID NO:1; serine at a position corresponding to position 316 of SEQ ID NO:1; asparagine at a position corresponding to position 322 of SEQ ID NO:1; serine at a position corresponding to position 325 of SEQ ID NO:1; glutamic acid at a position corresponding to position 327 of SEQ ID NO:1; proline at a position corresponding to position 330 of SEQ ID NO:1; lysine at a position corresponding to position 332 of SEQ ID NO:1; serine at a position corresponding to position 340 of SEQ ID NO:1; proline at a position corresponding to position 345 of SEQ ID NO:1; threonine at a position corresponding to position 346 of SEQ ID NO:1; asparagine at a position corresponding to position 354 of SEQ ID NO:1; threonine at a position corresponding to position 358 of SEQ ID NO:1; proline at a position corresponding to position 365 of SEQ ID NO:1; asparagine at a position corresponding to position 370 of SEQ ID NO:1; isoleucine at a position corresponding to position 373 of SEQ ID NO:1; asparagine at a position corresponding to position 378 of SEQ ID NO:1; histidine at a position corresponding to position 429 of SEQ ID NO:1; glycine at a position corresponding to position 443 of SEQ ID NO:1; glutamic acid at a position corresponding to position 453 of SEQ ID NO:1; threonine at a position corresponding to position 458 of SEQ ID NO:1; isoleucine at a position corresponding to position 464 of SEQ ID NO:1; glycine at a position corresponding to position 468 of SEQ ID NO:1; alanine at a position corresponding to position 473 of SEQ ID NO:1; alanine at a position corresponding to position 488 of SEQ ID NO:1; alanine at a position corresponding to position 490 of SEQ ID NO:1; valine at a position corresponding to position 496 of SEQ ID NO:1; histidine at a position corresponding to position 510 of SEQ ID NO:1; lysine at a position corresponding to position 511 of SEQ ID NO:1; lysine at a position corresponding to position 527 of SEQ ID NO:1; serine at a position corresponding to position 531 of SEQ ID NO:1; valine at a position corresponding to position 535 of SEQ ID NO:1; threonine at a position corresponding to position 537 of SEQ ID NO:1; glycine at a position corresponding to position 538 of SEQ ID NO:1; asparagine at a position corresponding to position 539 of SEQ ID NO:1; glycine at a position corresponding to position 543 of SEQ ID NO:1; asparagine at a position corresponding to position 553 of SEQ ID NO:1; serine at a position corresponding to position 564 of SEQ ID NO:1; phenylalanine at a position corresponding to position 565 of SEQ ID NO:1; serine at a position corresponding to position 577 of SEQ ID NO:1; glycine at a position corresponding to position 582 of SEQ ID NO:1; serine at a position corresponding to position 599 of SEQ ID NO:1; serine at a position corresponding to position 603 of SEQ ID NO:1; serine at a position corresponding to position 606 of SEQ ID NO:1; glycine at a position corresponding to position 611 of SEQ ID NO:1; methionine at a position corresponding to position 613 of SEQ ID NO:1; serine at a position corresponding to position 624 of SEQ ID NO:1; serine at a position corresponding to position 637 of SEQ ID NO:1; threonine at a position corresponding to position 644 of SEQ ID NO:1; threonine at a position corresponding to position 651 of SEQ ID NO:1; threonine at a position corresponding to position 654 of SEQ ID NO:1; proline at a position corresponding to position 678 of SEQ ID NO:1; threonine at a position corresponding to position 679 of SEQ ID NO:1; glutamic acid at a position corresponding to position 682 of SEQ ID NO:1; arginine at a position corresponding to position 685 of SEQ ID NO:1; proline at a position corresponding to position 686 of SEQ ID NO:1; serine at a position corresponding to position 688 of SEQ ID NO:1; aspartic acid at a position corresponding to position 689 of SEQ ID NO:1; leucine at a position corresponding to position 691 of SEQ ID NO:1; serine at a position corresponding to position 695 of SEQ ID NO:1; glycine at a position corresponding to position 697 of SEQ ID NO:1; isoleucine at a position corresponding to position 698 of SEQ ID NO:1; asparagine at a position corresponding to position 704 of SEQ ID NO:1; and proline at a position corresponding to position 710 of SEQ ID NO:1.

In some versions, the genetically modified CCNT1 gene encodes a protein comprising a sequence with a sequence identity of at least about 85%, at least about 90%, at least about 91%, at least about 92%, at least about 93%, at least about 94%, at least about 95.0%, at least about 95.1%, at least about 95.2%, at least about 95.3%, at least about 95.4%, at least about 95.5%, at least about 95.6%, at least about 95.7%, at least about 95.8%, at least about 95.9%, 96.0%, at least about 96.1%, at least about 96.2%, at least about 96.3%, at least about 96.4%, at least about 96.5%, at least about 96.6%, at least about 96.7%, at least about 96.8%, at least about 96.9%, 97.0%, at least about 97.1%, at least about 97.2%, at least about 97.3%, at least about 97.4%, at least about 97.5%, at least about 97.6%, at least about 97.7%, at least about 97.8%, at least about 97.9%, 98.0%, at least about 98.1%, at least about 98.2%, at least about 98.3%, at least about 98.4%, at least about 98.5%, at least about 98.6%, at least about 98.7%, at least about 98.8%, at least about 98.9%, 99.0%, at least about 99.1%, at least about 99.2%, at least about 99.3%, at least about 99.4%, at least about 99.5%, at least about 99.6%, at least about 99.7%, at least about 99.8%, at least about 99.9% or more with respect to SEQ ID NO:1.

Another aspect of the invention is a genetically modified XPO1 gene. The genetically modified XPO1 gene of the invention encodes a protein comprising a sequence with a sequence identity of at least about 80% with respect to SEQ ID NO:7 and includes at least one of a threonine at a position corresponding to position 411 of SEQ ID NO:7, a valine at a position corresponding to position 412 of SEQ ID NO:7, and a serine at a position corresponding to position 414 of SEQ ID NO:7.

SEQ ID NO:7 represents hXPO1-P411T-M412V-F414S, which is a modified version of the human XPO1 protein (hXPO1, XPO1, Exportin-1) comprising a substitution of a proline to a threonine at position 411 of hXPO1 (P411T), a substitution of a methionine to a valine at position 412 of hXPO1 (M412V), and a substitution of a phenylalanine to a serine at position 414 of hXPO1 (F414S). The genetically modified XPO1 gene encoding SEQ ID NO:7 can be generated from the human XPO1 gene encoding hXPO1 by modifying the codon encoding the proline at position 411 in hXPO1 to a codon encoding a threonine, modifying the codon encoding the methionine at position 412 in hXPO1 to a codon encoding a valine, and modifying the codon encoding the phenylalanine at position 414 in hXPO1 to a codon encoding a serine.

SEQ ID NO:7 is:

(SEQ ID NO: 7)
MPAIMTMLADHAARQLLDFSQKLDINLLDNVVNCLYHGEGAQQRMAQEVLT
HLKEHPDAWTRVDTILEFSQNMNTKYYGLQILENVIKTRWKILPRNQCEGI
KKYVVGLIIKTSSDPTCVEKEKVYIGKLNMILVQILKQEWPKHWPTFISDI
VGASRTSESLCQNNMVILKLLSEEVFDFSSGQITQVKSKHLKDSMCNEFSQ
IFQLCQFVMENSQNAPLVHATLETLLRFLNWIPLGYIFETKLISTLIYKFL
NVPMFRNVSLKCLTEIAGVSVSQYEEQFVTLFTLTMMQLKQMLPLNTNIRL
AYSNGKDDEQNFIQNLSLFLCTFLKEHDQLIEKRLNLRETLMEALHYMLLV
SEVEETEIFKICLEYWNHLAAELYRESPFSTSASPLLSGSQHFDVPPRRQL
YLTVLSKVRLLMVSRMAKPEEVLVVENDQGEVVREFMKDTDSINLYKNMRE
TLVYLTHLDYVDTERIMTEKLHNQVNGTEWSWKNLNTLCWAIGSISGAMHE
EDEKRFLVTVIKDLLGLCEQKRGKDNKAIIASNIMYIVGQYPRFLRAHWKF
LKTVVNKLFEFMHETHDGVQDMACDTFIKIAQKCRRHFVQVQVGEVMPFID
EILNNINTIICDLQPQQVHTFYEAVGYMIGAQTDQTVQEHLIEKYMLLPNQ
VWDSIIQQATKNVDILKDPETVKQLGSILKINVRACKAVGHPFVIQLGRIY
LDMLNVYKCLSENISAAIQANGEMVTKQPLIRSMRTVKRETLKLISGWVSR
SNDPQMVAENFVPPLLDAVLIDYQRNVPAAREPEVLSTMAIIVNKLGGHIT
AEIPQIFDAVFECTLNMINKDFEEYPEHRTNFFLLLQAVNSHCFPAFLAIP
PTQFKLVLDSIIWAFKHTMRNVADTGLQILFTLLQNVAQEEAAAQSFYQTY
FCDILQHIFSVVTDTSHTAGLTMHASILAYMFNLVEEGKISTSLNPGNPVN
NQIFLQEYVANLLKSAFFHLQDAQVKLFVTGLFSLNQDIPAFKEHLRDFLV
QIKEFAGEDTSDLFLEEREIALRQADEEKHKRQMSVPGIFNPHEIPEEMCD

An exemplary coding sequence encoding SEQ ID NO:7 is represented by SEQ ID NO:8:

(SEQ ID NO: 8)
ATGCCAGCAATTATGACAATGTTAGCAGACCATGCAGCTCGTCAGCTGCTT
GATTTCAGCCAAAAACTGGATATCAACTTATTAGATAATGTGGTGAATTGC
TTATACCATGGAGAAGGAGCCCAGCAAAGAATGGCTCAAGAAGTACTGACA
CATTTAAAGGAGCATCCTGATGCTTGGACAAGAGTCGACACAATTTTGGAA
TTTTCTCAGAATATGAATACGAAATACTATGGACTACAAATTTTGGAAAAT
GTGATAAAAACAAGGTGGAAGATTCTTCCAAGGAACCAGTGCGAAGGAATA
AAAAAATACGTTGTTGGCCTCATTATCAAGACGTCATCTGACCCAACTTGT
GTAGAGAAAGAAAAGGTGTATATCGGAAAATTAAATATGATCCTTGTTCAG
ATACTGAAACAAGAATGGCCCAAACATTGGCCAACTTTTATCAGTGATATT
GTTGGAGCAAGTAGGACCAGCGAAAGTCTCTGTCAAAATAATATGGTGATT
CTTAAACTCTTGAGTGAAGAAGTATTTGATTTCTCAGTGGACAGATAACC
CAAGTCAAATCTAAGCATTTAAAAGACAGCATGTGCAATGAATTCTCACAG
ATATTTCAACTGTGTCAGTTTGTAATGGAAAATTCTCAAAATGCTCCACTT
GTACATGCAACCTTGGAAACATTGCTCAGATTTCTGAACTGGATTCCCCTG
GGATATATTTTTGAGACCAAATTAATCAGCACATTGATTTATAAGTTCCTG
AATGTTCCAATGTTTCGAAATGTCTCTCTGAAGTGCCTCACTGAGATTGCT
GGTGTGAGTGTAAGCCAATATGAAGAACAATTTGTAACACTATTTACTCTG
ACAATGATGCAACTAAAGCAGATGCTTCCTTTAAATACCAATATTCGACTT
GCGTACTCAAATGGAAAAGATGATGAACAGAACTTCATTCAAAATCTCAGT
TTGTTTCTCTGCACCTTTCTTAAGGAACATGATCAACTTATAGAAAAAGA
TTAAATCTCAGGGAAACTCTTATGGAGGCCCTTCATTATATGTTGTTGGTA
TCTGAAGTAGAAGAAACTGAAATCTTTAAAATTTGTCTTGAATACTGGAAT
CATTTGGCTGCTGAACTCTATAGAGAGAGTCCATTCTCTACATCTGCGTCT
CCGTTGCTTTCTGGAAGTCAACATTTTGATGTTCCTCCCAGGAGACAGCTG
TATTTGACCGTGTTATCAAAGGTCCGTTTATTAATGGTTAGTCGAATGGCT
AAACCAGAGGAAGTATTGGTTGTAGAGAATGATCAAGGAGAAGTTGTGAGA
GAATTCATGAAGGATACAGATTCCATAAATTTGTATAAGAATATGAGGGAA
ACATTGGTTTATCTTACTCATCTGGATTATGTAGATACAGAAAGAATAATG
ACAGAGAAGCTTCACAATCAAGTGAATGGTACAGAGTGGTCATGGAAAAAT
TTGAATACATTGTGTTGGGCAATAGGCTCCATTAGTGGAGCAATGCATGAA
GAGGACGAAAAACGATTTCTTGTTACTGTTATAAAGGATCTATTAGGATTA
TGTGAACAGAAAAGAGGCAAAGATAATAAAGCTATTATTGCATCAAATATC
ATGTACATAGTAGGTCAATACCCACGTTTTTTGAGAGCTCACTGGAAATTT
CTGAAGACTGTAGTTAACAAGCTGTTCGAATTCATGCATGAGACCCATGAT
GGAGTCCAGGATATGGCTTGTGATACTTTCATTAAAATAGCCCAAAAATGC
CGCAGGCATTTCGTTCAGGTTCAGGTTGGAGAAGTGATGCCATTTATTGAT
GAAATTTTGAACAACATTAACACTATTATTTGTGATCTTCAGCCTCAACAG
GTTCATACGTTTTATGAAGCTGTGGGGTACATGATTGGTGCACAAACAGAT
CAAACAGTACAAGAACACTTGATAGAAAAGTACATGTTACTCCCTAATCAA
GTGTGGGATAGTATAATCCAGCAGGCAACCAAAAATGTGGATATACTGAAA
GATCCTGAAACAGTCAAGCAGCTTGGTAGCATTTTGAAAACAAATGTGAGA
GCCTGCAAAGCTGTTGGACACCCCTTTGTAATTCAGCTTGGAAGAATTTAT
TTAGATATGCTTAATGTATACAAGTGCCTCAGTGAAAATATTTCTGCAGCT
ATCCAAGCTAATGGTGAAATGGTTACAAAGCAACCATTGATTAGAAGTATG
CGAACTGTAAAAAGGGAAACTTTAAAGTTAATATCTGGTTGGGTGAGCCGA
TCCAATGATCCACAGATGGTCGCTGAAAATTTTGTTCCCCCTCTGTTGGAT
GCAGTTCTCATTGATTATCAGAGAAATGTCCCAGCTGCTAGAGAACCAGAA
GTGCTTAGTACTATGGCCATAATTGTCAACAAGTTAGGGGGACATATAACA
GCTGAAATACCTCAAATATTTGATGCTGTTTTTGAATGCACATTGAATATG
ATAAATAAGGACTTTGAAGAATATCCTGAACATAGAACGAACTTTTTCTTA
CTACTTCAGGCTGTCAATTCTCATTGTTTCCCAGCATTCCTTGCTATTCCA
CCTACACAGTTTAAACTTGTTTTGGATTCCATCATTTGGGCTTTCAAACAT
ACTATGAGGAATGTCGCAGATACGGGCTTACAGATACTTTTTACACTCTTA
CAAAATGTTGCACAAGAAGAGCTGCAGCTCAGAGTTTTTATCAAACTTAT
TTTTGTGATATTCTCCAGCATATCTTTTCTGTTGTGACAGACACTTCACAT
ACTGCTGGTTTAACAATGCATGCATCAATTCTTGCATATATGTTTAATTTG

GTTGAAGAAGGAAAAATAAGTACATCATTAAATCCTGGAAATCCAGTTAAC

AACCAAATCTTTCTTCAGGAATATGTGGCTAATCTCCTTAAGTCGGCCTTC

CCTCACCTACAAGATGCTCAAGTAAAGCTCTTTGTGACAGGGCTTTTCAGC

TTAAATCAAGATATTCCTGCTTTCAAGGAACATTTAAGAGATTTCCTAGTT

CAAATAAAGGAATTTGCAGGTGAAGACACTTCTGATTTGTTTTTGGAAGAG

AGAGAAATAGCCCTACGGCAGGCTGATGAAGAGAAACATAAACGTCAAATG

TCTGTCCCTGGCATCTTTAATCCACATGAGATTCCAGAAGAAATGTGTGAT

TAA

The amino acid sequence of an exemplary hXPO1 is represented by SEQ ID NO:9:

(SEQ ID NO: 9)
MPAIMTMLADHAARQLLDFSQKLDINLLDNVVNCLYHGEGAQQRMAQEVLT

HLKEHPDAWTRVDTILEFSQNMNTKYYGLQILENVIKTRWKILPRNQCEGI

KKYVVGLIIKTSSDPTCVEKEKVYIGKLNMILVQILKQEWPKHWPTFISDI

VGASRTSESLCQNNMVILKLLSEEVFDFSSGQITQVKSKHLKDSMCNEFSQ

IFQLCQFVMENSQNAPLVHATLETLLRFLNWIPLGYIFETKLISTLIYKFL

NVPMFRNVSLKCLTEIAGVSVSQYEEQFVTLFTLTMMQLKQMLPLNTNIRL

AYSNGKDDEQNFIQNLSLFLCTFLKEHDQLIEKRLNLRETLMEALHYMLLV

SEVEETEIFKICLEYWNHLAAELYRESPFSTSASPLLSGSQHFDVPPRRQL

YLPMLFKVRLLMVSRMAKPEEVLVVENDQGEVVREFMKDTDSINLYKNMRE

TLVYLTHLDYVDTERIMTEKLHNQVNGTEWSWKNLNTLCWAIGSISGAMHE

EDEKRFLVTVIKDLLGLCEQKRGKDNKAIIASNIMYIVGQYPRFLRAHWKF

LKTVVNKLFEFMHETHDGVQDMACDTFIKIAQKCRRHFVQVQVGEVMPFID

EILNNINTIICDLQPQQVHTFYEAVGYMIGAQTDQTVQEHLIEKYMLLPNQ

VWDSIIQQATKNVDILKDPETVKQLGSILKTNVRACKAVGHPFVIQLGRIY

LDMLNVYKCLSENISAAIQANGEMVTKQPLIRSMRTVKRETLKLISGWVSR

SNDPQMVAENFVPPLLDAVLIDYQRNVPAAREPEVLSTMAIIVNKLGGHIT

AEIPQIFDAVFECTLNMINKDFEEYPEHRTNFFLLLQAVNSHCFPAFLAIP

PTQFKLVLDSIIWAFKHTMRNVADTGLQILFTLLQNVAQEEAAAQSFYQTY

FCDILQHIFSVVTDTSHTAGLTMHASILAYMFNLVEEGKISTSLNPGNPVN

NQIFLQEYVANLLKSAFFHLQDAQVKLFVTGLFSLNQDIPAFKEHLRDFLV

QIKEFAGEDTSDLFLEEREIALRQADEEKHKRQMSVPGIFNPHEIPEEMCD

Various isoforms or variants of hXPO1 include modifications to SEQ ID NO:9 in which position 406 includes glycine (G) in place of arginine (R), position 953 includes glycine (G) in place of valine (V), and/or position 989 includes isoleucine (I) in place of leucine (L). Any of these modifications can be included in the protein encoded by the genetically modified XPO1 gene of the invention.

A coding sequence of the exemplary hXPO1 is represented by SEQ ID NO:10:

(SEQ ID NO: 10)
ATGCCAGCAATTATGACAATGTTAGCAGACCATGCAGCTCGTCAGCTGCTT

GATTTCAGCCAAAAACTGGATATCAACTTATTAGATAATGTGGTGAATTGC

TTATACCATGGAGAAGGAGCCCAGCAAAGAATGGCTCAAGAAGTACTGACA

CATTTAAAGGAGCATCCTGATGCTTGGACAAGAGTCGACACAATTTTGGAA

TTTTCTCAGAATATGAATACGAAATACTATGGACTACAAATTTTGGAAAAT

GTGATAAAAACAAGGTGGAAGATTCTTCCAAGGAACCAGTGCGAAGGAATA

AAAAAATACGTTGTTGGCCTCATTATCAAGACGTCATCTGACCCAACTTGT

GTAGAGAAAGAAAAGGTGTATATCGGAAAATTAAATATGATCCTTGTTCAG

ATACTGAAACAAGAATGGCCCAAACATTGGCCAACTTTTATCAGTGATATT

GTTGGAGCAAGTAGGACCAGCGAAAGTCTCTGTCAAAATAATATGGTGATT

CTTAAACTCTTGAGTGAAGAAGTATTTGATTTCTCTAGTGGACAGATAACC

CAAGTCAAATCTAAGCATTTAAAAGACAGCATGTGCAATGAATTCTCACAG

ATATTTCAACTGTGTCAGTTTGTAATGGAAAATTCTCAAAATGCTCCACTT

GTACATGCAACCTTGGAAACATTGCTCAGATTTCTGAACTGGATTCCCCTG

GGATATATTTTTGAGACCAAATTAATCAGCACATTGATTTATAAGTTCCTG

AATGTTCCAATGTTTCGAAATGTCTCTCTGAAGTGCCTCACTGAGATTGCT

GGTGTGAGTGTAAGCCAATATGAAGAACAATTTGTAACACTATTTACTCTG

ACAATGATGCAACTAAAGCAGATGCTTCCTTTAAATACCAATATTCGACTT

GCGTACTCAAATGGAAAAGATGATGAACAGAACTTCATTCAAAATCTCAGT

TTGTTTCTCTGCACCTTTCTTAAGGAACATGATCAACTTATAGAAAAAAGA

TTAAATCTCAGGGAAACTCTTATGGAGGCCCTTCATTATATGTTGTTGGTA

TCTGAAGTAGAAGAAACTGAAATCTTTAAAATTTGTCTTGAATACTGGAAT

CATTTGGCTGCTGAACTCTATAGAGAGTCCATTCTCTACATCTGCCTCT

CCGTTGCTTTCTGGAAGTCAACATTTTGATGTTCCTCCCAGGAGACAGCTA

TATTTGCCCATGTTATTCAAGGTCCGTTTATTAATGGTTAGTCGAATGGCT

AAACCAGAGGAAGTATTGGTTGTAGAGAATGATCAAGGAGAAGTTGTGAGA

GAATTCATGAAGGATACAGATTCCATAAATTTGTATAAGAATATGAGGGAA

ACATTGGTTTATCTTACTCATCTGGATTATGTAGATACAGAAAGAATAATG

ACAGAGAAGCTTCACAATCAAGTGAATGGTACAGAGTGGTCATGGAAAAAT

TTGAATACATTGTGTTGGGCAATAGGCTCCATTAGTGGAGCAATGCATGAA

GAGGACGAAAAACGATTTCTTGTTACTGTTATAAAGGATCTATTAGGATTA

TGTGAACAGAAAAGAGGCAAAGATAATAAAGCTATTATTGCATCAAATATC

ATGTACATAGTAGGTCAATACCCACGTTTTTTGAGAGCTCACTGGAAATTT

CTGAAGACTGTAGTTAACAAGCTGTTCGAATTCATGCATGAGACCCATGAT

GGAGTCCAGGATATGGCTTGTGATACTTTCATTAAAATAGCCCAAAAATGC

CGCAGGCATTTCGTTCAGGTTCAGGTTGGAGAAGTGATGCCATTTATTGAT

GAAATTTTGAACAACATTAACACTATTATTTGTGATCTTCAGCCTCAACAG

GTTCATACGTTTTATGAAGCTGTGGGGTACATGATTGGTGCACAAACAGAT

-continued

```
CAAACAGTACAAGAACACTTGATAGAAAAGTACATGTTACTCCCTAATCAA

GTGTGGGATAGTATAATCCAGCAGGCAACCAAAAATGTGGATATACTGAAA

GATCCTGAAACAGTCAAGCAGCTTGGTAGCATTTTGAAAACAAATGTGAGA

GCCTGCAAAGCTGTTGGACACCCCTTTGTAATTCAGCTTGGAAGAATTTAT

TTAGATATGCTTAATGTATACAAGTGCCTCAGTGAAAATATTTCTGCAGCT

ATCCAAGCTAATGGTGAAATGGTTACAAAGCAACCATTGATTAGAAGTATG

CGAACTGTAAAAAGGGAAACTTTAAAGTTAATATCTGGTTGGGTGAGCCGA

TCCAATGATCCACAGATGGTCGCTGAAAATTTTGTTCCCCCTCTGTTGGAT

GCAGTTCTCATTGATTATCAGAGAAATGTCCCAGCTGCTAGAGAACCAGAA

GTGCTTAGTACTATGGCCATAATTGTCAACAAGTTAGGGGGACATATAACA

GCTGAAATACCTCAAATATTTGATGCTGTTTTTGAATGCACATTGAATATG

ATAAATAAGGACTTTGAAGAATATCCTGAACATAGAACGAACTTTTTCTTA

CTACTTCAGGCTGTCAATTCTCATTGTTTCCCAGCATTCCTTGCTATTCCA

CCTACACAGTTTAAACTTGTTTTGGATTCCATCATTTGGGCTTTCAAACAT

ACTATGAGGAATGTCGCAGATACGGGCTTACAGATACTTTTTACACTCTTA

CAAAATGTTGCACAAGAAGAAGCTGCAGCTCAGAGTTTTTATCAAACTTAT

TTTTGTGATATTCTCCAGCATATCTTTTCTGTTGTGACAGACACTTCACAT

ACTGCTGGTTTAACAATGCATGCATCAATTCTTGCATATATGTTTAATTTG

GTTGAAGAAGGAAAAATAAGTACATCATTAAATCCTGGAAATCCAGTTAAC

AACCAAATCTTTCTTCAGGAATATGTGGCTAATCTCCTTAAGTCGGCCTTC

CCTCACCTACAAGATGCTCAAGTAAAGCTCTTTGTGACAGGGCTTTTCAGC

TTAAATCAAGATATTCCTGCTTTCAAGGAACATTTAAGAGATTTCCTAGTT

CAAATAAAGGAATTTGCAGGTGAAGACACTTCTGATTTGTTTTTGGAAGAG

AGAGAAATAGCCCTACGGCAGGCTGATGAAGAGAAACATAAACGTCAAATG

TCTGTCCCTGGCATCTTTAATCCACATGAGATTCCAGAAGAAATGTGTGAT

TAA
```

The sequence of a portion of an exemplary human XPO1 gene that can be edited to generate an exemplary genetically modified XPO1 gene is represented by SEQ ID NO:11:

```
                                            (SEQ ID NO: 11)
TTCTCTCCTCTGTGATGGTACATTTGGGTTGTGATACCACTTATTGGCACC

CAAGGCCTTTTAAATAAATGTCGTTCCATTAGGAGACATGATAAAAATACA

TATTGATCAACTACTATGTGAGAGATTTTTGAAGTGCTTTAGGGCATGTCA

GAAGAAGCAGAGTTACTCCAGAGTTTGCTGTCTATTTGATAAGTATTGAAA

TCTGAGTTGTGATGAATAAAACATGAATTTTTATTTTCCCTTAAGGTGTAA

CAAGTGAAAAGCAATTTGAAGTTGGTAATGTTTAAGAATTATTTTAACAGT

TTTGGTCTTCTGTGTAGGCCCTTCATTATATGTTGTTGGTATCTGAAGTAG

AAGAAACTGAAATCTTTAAAATTTGTCTTGAATACTGGAATCATTTGGCTG

CTGAACTCTATAGAGAGAGTCCATTCTCTACATCTGCCTCTCCGTTGCTTT

CTGGAAGTCAACATTTTGATGTTCCTCCCAGGAGACAGCTATATTTGCCCA

TGTTATTCAAGGTAACAGAGCGGTTGGTTGAGTGTTCTTCCTGTTGCACAC

TGTGGTTTTGAGGTCTGAATCCAAATACTTCTAATCTGTGTAAATAAATTA

GCTATAAAAAGAGAACCCAACAACTTCTCCATGAGTGTGGAAAACTAGAAC

ATGAAAGGAGTTGAGTCTAGAACCTTGATTCTCAAGAGTGTGGTCCTTCTC

TCAGTATCAACATTGGTTGTGATTTCGTTAGGCAAATTCATTGGCCACCTG

CCAATCTACTAAACCAGAGTCTAGGAATGAGACACAGGAAACTCCTGTAAC

AGAAGTTGGTTAAAAAAATCACATTAAAACACACTTAAATAATTATAAAGC

CATTTTTGTAGAATTACAGTGAAAAAAAATTTTTTCTTTTGGAGACAGGGT

CTTGCTCTGTGGCTCAGGTTGGAGTGCAGTGGCGTGGTCATAGCTCACTAC

AATCTTGA
```

Exemplary methods for performing the editing are described in the following examples.

The threonine at position 411, the valine at position 412, and/or the serine at position 414 of the protein encoded by the genetically modified XPO1 gene of the invention are modeled after the threonine at position 411, the valine at position 412, and/or the serine at position 414 of the mouse XPO1 protein (mXPO1, Xpo1), which is represented by SEQ ID NO:12:

```
                                            (SEQ ID NO: 12)
MPAIMTMLADHAARQLLDFSQKLDINLLDNVVNCLYHGEGAQQRMAQEVLT

HLKEHPDAWTRVDTILEFSQNMNTKYYGLQILENVIKTRWKILPRNQCEGI

KKYVVGLIIKTSSDPTCVEKEKVYIGKLNMILVQILKQEWPKHWPTFISDI

VGASRTSESLCQNNMVILKLLSEEVFDFSSGQITQVKAKHLKDSMCNEFSQ

IFQLCQFVMENSQNAPLVHATLETLLRFLNWIPLGYIFETKLISTLIYKFL

NVPMFRNVSLKCLTEIAGVSVSQYEEQFETLFTLTMMQLKQMLPLNTNIRL

AYSNGKDDEQNFIQNLSLFLCTFLKEHGQLLEKRLNLREALMEALHYMLLV

SEVEETEIFKICLEYWNHLAAELYRESPFSTSASPLLSGSQHFDIPPRRQL

YLTVLSKVRLLMVSRMAKPEEVLVVENDQGEVVREFMKDTDSINLYKNMRE

TLVYLTHLDYVDTEIIMTKKLQNQVNGTEWSWKNLNTLCWAIGSISGAMHE

EDEKRFLVTVIKDLLGLCEQKRGKDNKAIIASNIMYIVGQYPRFLRAHWKF

LKTVVNKLFEFMHETHDGVQDMACDTFIKIAQKCRRHFVQVQVGEVMPFID

EILNNINTIICDLQPQQVHTFYEAVGYMIGAQTDQTVQEHLIEKYMLLPNQ

VWDSIIQQATKNVDILKDPETVKQLGSILKTNVRACKAVGHPFVIQLGRIY

LDMLNVYKCLSENISAAIQANGEMVTKQPLIRSMRTVKRETLKLISGWVSR

SNDPQMVAENFVPPLLDAVLIDYQRNVPAAREPEVLSTMAIIVNKLGGHIT

AEIPQIFDAVFECTLNMINKDFEEYPEHRTNFFLLLQAVNSHCFPAFLAIP

PAQFKLVLDSIIWAFKHTMRNVADTGLQILFTLLQNVAQEEAAAQSFYQTY

FCDILQHIFSVVTDTSHTAGLTMHASILAYMFNLVEEGKISTPLNPGNPVN

NQMFIQDYVANLLKSAFFHLQDAQVKLFVTGLFSLNQDIPAFKEHLRDFLV

QIKEFAGEDTSDLFLEERETALRQAQEEKHKLQMSVPGILNPHEIPEEMCD
```

An alignment of hXPO1-P411T-M412V-F414S (SEQ ID NO:7, shown as hXPO1*), hXPO1 (SEQ ID NO:9), and mXPO1 (SEQ ID NO:12) as aligned by Clustal Omega using default parameters is shown in FIGS. 2A and 2B.

With the exception of T411, V412, and/or S414, the genetically modified XPO1 gene may encode a number of differences with respect to mXPO1 or other native XPO1 proteins. These differences may comprise at least one, some, or all of: an amino acid other than aspartic acid at a position corresponding to position 100 of SEQ ID NO:7; an amino acid other than alanine at a position corresponding to position 118 of SEQ ID NO:7; an amino acid other than glycine at a position corresponding to position 151 of SEQ ID NO:7; an amino acid other than alanine at a position corresponding to position 191 of SEQ ID NO:7; an amino acid other than serine at a position corresponding to position 215 of SEQ ID NO:7; an amino acid other than glutamic acid at a position corresponding to position 284 of SEQ ID NO:7; an amino acid other than valine at a position corresponding to position 306 of SEQ ID NO:7; an amino acid other than glycine at a position corresponding to position 334 of SEQ ID NO:7; an amino acid other than leucine at a position corresponding to position 337 of SEQ ID NO:7; an amino acid other than alanine at a position corresponding to position 346 of SEQ ID NO:7; an amino acid other than isoleucine at a position corresponding to position 402 of SEQ ID NO:7; an amino acid other than isoleucine at a position corresponding to position 474 of SEQ ID NO:7; an amino acid other than lysine at a position corresponding to position 478 of SEQ ID NO:7; an amino acid other than glutamine at a position corresponding to position 481 of SEQ ID NO:7; an amino acid other than alanine at a position corresponding to position 869 of SEQ ID NO:7; an amino acid other than glycine at a position corresponding to position 909 of SEQ ID NO:7; an amino acid other than proline at a position corresponding to position 961 of SEQ ID NO:7; an amino acid other than serine at a position corresponding to position 966 of SEQ ID NO:7; an amino acid other than serine at a position corresponding to position 969 of SEQ ID NO:7; an amino acid other than valine and/or methionine at a position corresponding to position 972 of SEQ ID NO:7; an amino acid other than isoleucine at a position corresponding to position 974 of SEQ ID NO:7; an amino acid other than aspartic acid at a position corresponding to position 976 of SEQ ID NO:7; an amino acid other than threonine at a position corresponding to position 1040 of SEQ ID NO:7; an amino acid other than glycine at a position corresponding to position 1043 of SEQ ID NO:7; an amino acid other than glutamine at a position corresponding to position 1046 of SEQ ID NO:7; an amino acid other than leucine at a position corresponding to position 1052 of SEQ ID NO:7; and an amino acid other than leucine at a position corresponding to position 1060 of SEQ ID NO:7.

In some versions, the differences encoded by the genetically modified XPO1 gene with respect to mXPO1 or other native XPO1 proteins may comprise at least one, some, or all of: glutamic acid at a position corresponding to position 100 of SEQ ID NO:7; threonine at a position corresponding to position 118 of SEQ ID NO:7; serine at a position corresponding to position 151 of SEQ ID NO:7; serine at a position corresponding to position 191 of SEQ ID NO:7; asparagine at a position corresponding to position 215 of SEQ ID NO:7; valine at a position corresponding to position 284 of SEQ ID NO:7; leucine at a position corresponding to position 306 of SEQ ID NO:7; aspartic acid at a position corresponding to position 334 of SEQ ID NO:7; isoleucine at a position corresponding to position 337 of SEQ ID NO:7; threonine at a position corresponding to position 346 of SEQ ID NO:7; valine at a position corresponding to position 402 of SEQ ID NO:7; arginine at a position corresponding to position 474 of SEQ ID NO:7; glutamic acid at a position corresponding to position 478 of SEQ ID NO:7; histidine at a position corresponding to position 481 of SEQ ID NO:7; threonine at a position corresponding to position 869 of SEQ ID NO:7; alanine at a position corresponding to position 909 of SEQ ID NO:7; serine at a position corresponding to position 961 of SEQ ID NO:7; asparagine at a position corresponding to position 966 of SEQ ID NO:7; asparagine at a position corresponding to position 969 of SEQ ID NO:7; isoleucine at a position corresponding to position 972 of SEQ ID NO:7; leucine at a position corresponding to position 974 of SEQ ID NO:7; glutamic acid at a position corresponding to position 976 of SEQ ID NO:7; isoleucine at a position corresponding to position 1040 of SEQ ID NO:7; arginine at a position corresponding to position 1043 of SEQ ID NO:7; aspartic acid at a position corresponding to position 1046 of SEQ ID NO:7; arginine at a position corresponding to position 1052 of SEQ ID NO:7; and phenylalanine at a position corresponding to position 1060 of SEQ ID NO:7.

In some versions, the genetically modified XPO1 gene encodes a protein comprising a sequence with a sequence identity of at least about 85%, at least about 90%, at least about 91%, at least about 92%, at least about 93%, at least about 94%, at least about 95.0%, at least about 95.1%, at least about 95.2%, at least about 95.3%, at least about 95.4%, at least about 95.5%, at least about 95.6%, at least about 95.7%, at least about 95.8%, at least about 95.9%, 96.0%, at least about 96.1%, at least about 96.2%, at least about 96.3%, at least about 96.4%, at least about 96.5%, at least about 96.6%, at least about 96.7%, at least about 96.8%, at least about 96.9%, 97.0%, at least about 97.1%, at least about 97.2%, at least about 97.3%, at least about 97.4%, at least about 97.5%, at least about 97.6%, at least about 97.7%, at least about 97.8%, at least about 97.9%, 98.0%, at least about 98.1%, at least about 98.2%, at least about 98.3%, at least about 98.4%, at least about 98.5%, at least about 98.6%, at least about 98.7%, at least about 98.8%, at least about 98.9%, 99.0%, at least about 99.1%, at least about 99.2%, at least about 99.3%, at least about 99.4%, at least about 99.5%, at least about 99.6%, at least about 99.7%, at least about 99.8%, at least about 99.9% or more with respect to SEQ ID NO:7.

Throughout the specification, a reference may be made using an abbreviation of a gene name or a polypeptide name, but it is understood that such an abbreviated gene or polypeptide name represents the genus of genes or polypeptides, respectively. Such gene names include all genes encoding the same polypeptide and homologous polypeptides having the same physiological function. Polypeptide names include all polypeptides that have the same activity (e.g., that catalyze the same fundamental chemical reaction).

Unless otherwise indicated, the accession numbers referenced herein are derived from the NCBI database (National Center for Biotechnology Information) maintained by the National Institute of Health, U.S.A.

EC numbers are established by the Nomenclature Committee of the International Union of Biochemistry and Molecular Biology (NC-IUBMB) (available on the world wide web at chem.qmul/ac/uk/iubmb/enzyme/. The EC numbers referenced herein are derived from the KEGG Ligand database, maintained by the Kyoto Encyclopedia of Genes and Genomics, sponsored in part by the University of Tokyo.

The term "alignment" refers to a method of comparing two or more polynucleotides or polypeptide sequences for the purpose of determining their relationship to each other. Alignments are typically performed by computer programs that apply various algorithms; however it is also possible to perform an alignment by hand. Alignment programs typically iterate through potential alignments of sequences and score the alignments using substitution tables, employing a variety of strategies to reach a potential optimal alignment score. Commonly-used alignment algorithms include, but are not limited to, CLUSTALW, (see, Thompson J. D., Higgins D. G., Gibson T. J., CLUSTAL W: improving the sensitivity of progressive multiple sequence alignment through sequence weighting, position-specific gap penalties and weight matrix choice, Nucleic Acids Research 22: 4673-4680, 1994); CLUSTALV, (see, Larkin M. A., et al., CLUSTALW2, ClustalW and ClustalX version 2, Bioinformatics 23(21): 2947-2948, 2007); Jotun-Hein, Muscle et al., MUSCLE: a multiple sequence alignment method with reduced time and space complexity, BMC Bioinformatics 5: 113, 2004); Mafft, Kalign, ProbCons, and T-Coffee (see Notredame et al., T-Coffee: A novel method for multiple sequence alignments, Journal of Molecular Biology 302: 205-217, 2000). Exemplary programs that implement one or more of the above algorithms include, but are not limited to MegAlign from DNAStar (DNAStar, Inc. 3801 Regent St. Madison, Wis. 53705), MUSCLE, T-Coffee, CLUSTALX, CLUSTALV, JalView, Phylip, and Discovery Studio from Accelrys (Accelrys, Inc., 10188 Telesis Ct, Suite 100, San Diego, Calif. 92121). In a non-limiting example, MegAlign is used to implement the CLUSTALW alignment algorithm with the following parameters: Gap Penalty 10, Gap Length Penalty 0.20, Delay Divergent Seqs (30%) DNA Transition Weight 0.50, Protein Weight matrix Gonnet Series, DNA Weight Matrix IUB.

The term "consensus sequence" or "canonical sequence" refers to an archetypical amino acid sequence against which all variants of a particular protein or sequence of interest are compared. Either term also refers to a sequence that sets forth the nucleotides that are most often present in a polynucleotide sequence of interest. For each position of a protein, the consensus sequence gives the amino acid that is most abundant in that position in the sequence alignment.

The term "conservative substitutions" or "conserved substitutions" refers to, for example, a substitution of an amino acid with a conservative variant. The proteins encoded by the genetically modified CCNT1 and XPO1 genes may comprise one or more conservative substitutions for any residue at any position, except for the tyrosine at the position corresponding to position 261 of SEQ ID NO:1 in the genetically modified CCNT1 gene and the threonine at the position corresponding to position 411 of SEQ ID NO:7, the valine at the position corresponding to position 412 of SEQ ID NO:7, and the serine at the position corresponding to position 414 of SEQ ID NO:7 in the genetically modified XPO1 gene.

"Conservative variant" refers to residues that are functionally similar to a given residue. Amino acids within the following groups are conservative variants of one another: glycine, alanine, serine, and proline (very small); alanine, isoleucine, leucine, methionine, phenylalanine, valine, proline, and glycine (hydrophobic); alanine, valine, leucine, isoleucine, methionine (aliphatic-like); cysteine, serine, threonine, asparagine, tyrosine, and glutamine (polar); phenylalanine, tryptophan, tyrosine (aromatic); lysine, arginine, and histidine (basic); aspartate and glutamate (acidic); alanine and glycine; asparagine and glutamine; arginine and lysine; isoleucine, leucine, methionine, and valine; and serine and threonine.

The terms "corresponds to" or "corresponding to" refer to an amino acid residue or position in a first protein sequence being positionally equivalent to an amino acid residue or position in a second reference protein sequence by virtue of the fact that the residue or position in the first protein sequence aligns to the residue or position in the reference sequence using bioinformatic techniques, for example, using the methods described herein for preparing a sequence alignment. The corresponding residue in the first protein sequence is then assigned the position number in the second reference protein sequence.

The term "deletion," when used in the context of an amino acid sequence, means a deletion in or a removal of one or more residues from the amino acid sequence of a precursor protein, resulting in a mutant protein having at least one less amino acid residue as compared to the precursor protein. The term can also be used in the context of a nucleotide sequence, which means a deletion in or removal of a nucleotide from the polynucleotide sequence of a precursor polynucleotide.

The term "expressed genes" refers to genes that are transcribed into messenger RNA (mRNA) and then translated into protein, as well as genes that are transcribed into types of RNA, such as transfer RNA (tRNA), ribosomal RNA (rRNA), and regulatory RNA, which are not translated into protein.

"Gene" refers to a polynucleotide (e.g., a DNA segment), which encodes a polypeptide, and may include regions preceding and following the coding regions as well as intervening sequences (introns) between individual coding segments (exons).

The term "homologous genes" refers to a pair of genes from different but related species, which correspond to each other and which are identical or similar to each other. The term encompasses genes that are separated by the speciation process during the development of new species) (e.g., orthologous genes), as well as genes that have been separated by genetic duplication (e.g., paralogous genes).

The term "endogenous protein" refers to a protein that is native to or naturally occurring in a cell. "Endogenous polynucleotide" refers to a polynucleotide that is in the cell and was not introduced into the cell using recombinant engineering techniques, for example, a gene that was present in the cell when the cell was originally isolated from nature. Conversely, the term "heterologous" refers to a protein or a polynucleotide that does not naturally occur in a host cell.

The term "homologous recombination" refers to the exchange of DNA fragments between two DNA molecules or paired chromosomes at sites of identical or nearly identical nucleotide sequences. In certain embodiments, chromosomal integration is homologous recombination.

The term "homologous sequences" as used herein refers to a polynucleotide or polypeptide sequence having, for example, about 100%, about 99% or more, about 98% or more, about 97% or more, about 96% or more, about 95% or more, about 94% or more, about 93% or more, about 92% or more, about 91% or more, about 90% or more, about 88% or more, about 85% or more, about 80% or more, about 75% or more, about 70% or more, about 65% or more, about 60% or more, about 55% or more, about 50% or more, about 45% or more, or about 40% or more sequence identity to another polynucleotide or polypeptide sequence when optimally aligned for comparison. In particular embodiments, homologous sequences can retain the same type and/or level of a particular activity of interest. In some embodiments, homologous sequences have between 85% and 100% sequence identity, whereas in other embodiments there is between 90% and 100% sequence identity. In particular embodiments, there is 95% and 100% sequence identity.

"Homology" refers to sequence similarity or sequence identity. Homology is determined using standard techniques known in the art (see, e.g., Smith and Waterman, Adv. Appl. Math., 2:482, 1981; Needleman and Wunsch, J. Mol. Biol., 48:443, 1970; Pearson and Lipman, Proc. Natl. Acad. Sci. USA 85:2444, 1988; programs such as GAP, BESTFIT, FASTA, and TFASTA in the Wisconsin Genetics Software Package (Genetics Computer Group, Madison, Wis.); and Devereux et al., Nucl. Acid Res., 12:387-395, 1984). A non-limiting example includes the use of the BLAST program (Altschul et al., Gapped BLAST and PSI-BLAST: a new generation of protein database search programs, Nucleic Acids Res. 25:3389-3402, 1997) to identify sequences that can be said to be "homologous." A recent version such as version 2.2.16, 2.2.17, 2.2.18, 2.2.19, or the latest version, including sub-programs such as blastp for protein-protein comparisons, blastn for nucleotide-nucleotide comparisons, tblastn for protein-nucleotide comparisons, or blastx for nucleotide-protein comparisons, and with parameters as follows: Maximum number of sequences returned 10,000 or 100,000; E-value (expectation value) of 1e-2 or 1e-5, word size 3, scoring matrix BLOSUM62, gap cost existence 11, gap cost extension 1, may be suitable. An E-value of 1e-5, for example, indicates that the chance of a homologous match occurring at random is about 1 in 10,000, thereby marking a high confidence of true homology.

The term "identical," in the context of two polynucleotide or polypeptide sequences, means that the residues in the two sequences are the same when aligned for maximum correspondence, as measured using a sequence comparison or analysis algorithm such as those described herein. For example, if when properly aligned, the corresponding segments of two sequences have identical residues at 5 positions out of 10, it is said that the two sequences have a 50% identity. Most bioinformatic programs report percent identity over aligned sequence regions, which are typically not the entire molecules. If an alignment is long enough and contains enough identical residues, an expectation value can be calculated, which indicates that the level of identity in the alignment is unlikely to occur by random chance.

The term "insertion," when used in the context of a polypeptide sequence, refers to an insertion in the amino acid sequence of a precursor polypeptide, resulting in a mutant polypeptide having an amino acid that is inserted between two existing contiguous amino acids, i.e., adjacent amino acids residues, which are present in the precursor polypeptide. The term "insertion," when used in the context of a polynucleotide sequence, refers to an insertion of one or more nucleotides in the precursor polynucleotide between two existing contiguous nucleotides, i.e., adjacent nucleotides, which are present in the precursor polynucleotides.

The term "introduced" refers to, in the context of introducing a polynucleotide sequence into a cell, any method suitable for transferring the polynucleotide sequence into the cell. Such methods for introduction include but are not limited to protoplast fusion, transfection, transformation, conjugation, and transduction (see, e.g., Ferrari et al., Genetics, in Hardwood et al, (eds.), Bacillus, Plenum Publishing Corp., pp. 57-72, 1989).

The term "isolated" or "purified" means a material that is removed from its original environment, for example, the natural environment if it is naturally occurring. A material is said to be "purified" when it is present in a particular composition in a higher or lower concentration than the concentration that exists prior to the purification step(s). For example, with respect to a composition normally found in a naturally occurring or wild type organism, such a composition is "purified" when the final composition does not include some material from the original matrix. As another example, a naturally occurring polynucleotide or polypeptide present in a living animal is not isolated, but the same polynucleotide or polypeptide, separated from some or all of the coexisting materials in the natural system, is isolated, whether such process is through genetic engineering or mechanical separation. Such polynucleotides can be parts of vectors. Alternatively, such polynucleotides or polypeptides can be parts of compositions. Such polynucleotides or polypeptides can be considered "isolated" because the vectors or compositions comprising thereof are not part of their natural environments. In another example, a polynucleotide or protein is said to be purified if it gives rise to essentially one band in an electrophoretic gel or a blot.

The term "mutation" refers to, in the context of a polynucleotide, a modification to the polynucleotide sequence resulting in a change in the sequence of a polynucleotide with reference to a precursor polynucleotide sequence. A mutant polynucleotide sequence can refer to an alteration that does not change the encoded amino acid sequence, for example, with regard to codon optimization for expression purposes, or that modifies a codon in such a way as to result in a modification of the encoded amino acid sequence. Mutations can be introduced into a polynucleotide through any number of methods known to those of ordinary skill in the art, including random mutagenesis, site-specific mutagenesis, oligonucleotide directed mutagenesis, gene shuffling, directed evolution techniques, combinatorial mutagenesis, site saturation mutagenesis among others.

"Mutation" or "mutated" means, in the context of a protein, a modification to the amino acid sequence resulting in a change in the sequence of a protein with reference to a precursor protein sequence. A mutation can refer to a substitution of one amino acid with another amino acid, an insertion or a deletion of one or more amino acid residues. A mutation can also be a truncation (e.g., a deletion or interruption) in a sequence or a subsequence from the precursor sequence. A mutation may also be an addition of a subsequence (e.g., two or more amino acids in a stretch, which are inserted between two contiguous amino acids in a precursor protein sequence) within a protein, or at either terminal end of a protein, thereby increasing the length of (or elongating) the protein. A mutation can be made by modifying the DNA sequence corresponding to a precursor protein. Mutations can be introduced into a protein sequence by known methods in the art, for example, by creating synthetic DNA sequences that encode the mutation with reference to precursor proteins, or chemically altering the protein itself. A "mutant" as used herein is a protein comprising a mutation.

A "naturally-occurring equivalent," in the context of the present invention, refers to a naturally occurring gene or protein, or a portion thereof that comprises a naturally occurring residue.

The term "operably linked," in the context of a polynucleotide sequence, refers to the placement of one polynucleotide sequence into a functional relationship with another polynucleotide sequence. For example, a DNA encoding a secretory leader (e.g., a signal peptide) is operably linked to a DNA encoding a polypeptide if it is expressed as a preprotein that participates in the secretion of the polypeptide. A promoter or an enhancer is operably linked to a coding sequence if it affects the transcription of the sequence. A ribosome binding site is operably linked to a coding sequence if it is positioned so as to facilitate translation. Generally, "operably linked" means that the DNA sequences being linked are contiguous, and, in the case of a secretory leader, contiguous and in the same reading frame.

The term "optimal alignment" refers to the alignment giving the highest overall alignment score.

"Overexpressed" or "overexpression" in a host cell occurs if the enzyme is expressed in the cell at a higher level than the level at which it is expressed in a corresponding wild-type cell.

The terms "percent sequence identity," "percent amino acid sequence identity," "percent gene sequence identity," and/or "percent polynucleotide sequence identity," with respect to two polypeptides, polynucleotides and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

A "promoter" is a polynucleotide sequence that functions to direct transcription of a downstream coding sequence. In preferred embodiments, the promoter is appropriate to the host cell in which the target coding sequence is being expressed. The promoter, together with other transcriptional and translational regulatory polynucleotide sequences (also termed "control sequences") is necessary to express a given coding sequence in a gene. In general, the transcriptional and translational regulatory sequences include, but are not limited to, promoter sequences, ribosomal binding sites, transcriptional start and stop sequences, translational start and stop sequences, and enhancer or activator sequences.

The terms "protein" and "polypeptide" are used interchangeably herein. The 3-letter code as well as the 1-letter code for amino acid residues as defined in conformity with the IUPAC-IUB Joint Commission on Biochemical Nomenclature (JCBN) is used throughout this disclosure. It is also understood that a polypeptide may be coded for by more than one polynucleotide sequence due to the degeneracy of the genetic code.

The term "recombinant," when used to modify the term "gene" or "protein" herein, is used synonymously with "genetically modified" and refers to a gene or protein comprising a heterologous (i.e., non-native or non-naturally occurring) sequence. The term "recombinant," when used to modify the term "cell" herein, is used synonymously with "genetically modified" and refers to a cell that has been modified to comprise a heterologous polynucleotide sequence, or that the cell is derived from a cell so modified. Thus, for example, recombinant cells express genes that are not found in identical form within the native (non-recombinant) form of the cells or express, as a result of deliberate human intervention, native genes that are otherwise abnormally expressed, underexpressed or not expressed at all. The terms "recombination," "recombining," and generating a "recombined" polynucleotide refer generally to the assembly of two or more polynucleotide fragments wherein the assembly gives rise to a chimeric polynucleotide made from the assembled parts.

The terms "regulatory segment," "regulatory sequence," or "expression control sequence" refer to a polynucleotide sequence that is operatively linked with another polynucleotide sequence that encodes the amino acid sequence of a polypeptide chain to effect the expression of that encoded amino acid sequence. The regulatory sequence can inhibit, repress, promote, or even drive the expression of the operably linked polynucleotide sequence encoding the amino acid sequence.

The term "substantially identical," in the context of two polynucleotides or two polypeptides refers to a polynucleotide or polypeptide that comprises at least 70% sequence identity, for example, at least 75%, at least 80%, at least 85%, at least 90%, at least 91%, at least 92%, at least 93%, at least 94%, at least 95%, at least 96%, at least 97%, at least 98%, or at least 99% sequence identity as compared to a reference sequence using the programs or algorithms (e.g., BLAST, ALIGN, CLUSTAL) using standard parameters.

"Substantially purified" means molecules that are at least about 60% free, preferably at least about 75% free, about 80% free, about 85% free, and more preferably at least about 90% free from other components with which they are naturally associated. As used herein, the term "purified" or "to purify" also refers to the removal of contaminants from a sample.

"Substitution" means replacing an amino acid in the sequence of a precursor protein with another amino acid at a particular position, resulting in a mutant of the precursor protein.

The term "transformed" or "stably transformed" cell refers to a cell that has a non-native (heterologous) polynucleotide sequence integrated into its genome or as an episomal plasmid that is maintained for at least two generations.

"Variant" is used interchangeably herein with "mutant."

"Vector" refers to a polynucleotide construct designed to introduce polynucleotides into one or more cell types. Vectors include cloning vectors, expression vectors, shuttle vectors, plasmids, cassettes and the like. In some embodiments, the polynucleotide construct comprises a polynucleotide sequence encoding a thioesterase (e.g., a precursor or a mature thioesterase) that is operably linked to a suitable prosequence (e.g., a secretory pro-sequence) capable of effecting the expression of the polynucleotide or gene in a suitable host.

"Wild-type" means, in the context of gene or protein, a polynucleotide or protein sequence that occurs in nature. In some embodiments, the wild-type sequence refers to a sequence of interest that is a starting point for protein engineering.

Genetically Modified Cells

Another aspect of the invention is directed to genetically modified cells.

The genetically modified cells of the invention are cells comprising one or more copies of the genetically modified genes of the invention. Specifically, the genetically modified cells of the invention may comprise one or more genetically modified CCNT1 genes of the invention, one or more genetically modified XPO1 genes of the invention, or one or more genetically modified CCNT1 genes of the invention and one or more genetically modified XPO1 genes of the invention. The genetically modified cells of the invention may comprise two or more, three or more, or four or more of one or both of the genetically modified CCNT1 and XPO1 genes of the invention. Each genetically modified CCNT1 and XPO1 gene present in the cell may be identical or different with respect to any other genetically modified CCNT1 and XPO1 gene(s) present in the cell.

The genetically modified CCNT1 and XPO1 genes may be incorporated in a chromosome in the cell or may be present extrachromosomally, such as on an extrachromosomal plasmid.

In some versions, the genetically modified cell is devoid of any native CCNT1 and/or XPO1 genes. Accordingly, the genetically modified cell may be devoid of any CCNT1 gene having an amino acid other than a tyrosine at a position corresponding to position 261 of SEQ ID NO:1; any XPO1 gene having an amino acid other than a threonine at a position corresponding to position 411 of SEQ ID NO:7, an amino acid other than a methionine at a position corresponding to position 412 of SEQ ID NO:7, and/or an amino acid other than a phenylalanine at a position corresponding to position 414 of SEQ ID NO:7; or any CCNT1 gene having an amino acid other than a tyrosine at a position corresponding to position 261 of SEQ ID NO:1 and any XPO1 gene having an amino acid other than a threonine at a position corresponding to position 411 of SEQ ID NO:7, an amino acid other than a methionine at a position corresponding to position 412 of SEQ ID NO:7, and/or an amino acid other than a phenylalanine at a position corresponding to position 414 of SEQ ID NO:7.

The genetically modified CCNT1 and/or XPO1 genes may replace one, some, or all or the native CCNT1 and/or XPO1 genes in the cell. In some versions, one, some or all of the native CCNT1 and/or XPO1 genes in the cell are directly edited to generate the genetically modified CCNT1 and/or XPO1 genes of the invention. The native genes can be edited using any gene editing tools known in the art, including CRISPR/Cas9, TALENS, etc. Exemplary methods of editing native CCNT1 and XPO1 genes to genetically modified CCNT1 and XPO1 genes of the invention are provided in the following examples.

The genetically modified cell may be a mammalian cell. In some versions, the cell is a primate cell. In some versions, the cell is a simian cell. In some versions, the cell is a human cell. In some versions, the cell is a non-human simian cell. In some versions, the cell is a feline cell. In some versions, the cell is a bovine cell.

The genetically modified cell may be a primary cell or may be an immortalized or transformed cell from a cell line.

The genetically modified cell may be an immune cell or a precursor of an immune cell. Exemplary immune cells (in various levels of generality) include white blood cells, leukocytes, lymphocytes, granulocytes, agranulocytes, myeloid cells, lymphoid cells, innate lymphoid cells, neutrophils, eosinophils (acidophilus), basophils, lymphocytes, monocytes, B cells, T cells, natural killer cells, macrophages, Kupffer cells, dendritic cells, mast cells, CD4+ T cells, CD8+ T cells, γδ T cells, regulatory (suppressor) T cells. Markers for the above-referenced immune cells are well known in the art.

"Precursor" as applied to a particular cell type herein refers to a cell capable of differentiating (whether in vivo, in vitro, or ex vivo) into a particular given cell. Exemplary immune cell precursors include hematopoietic stem cells, pluripotent stem cells, multipotent progenitors, myeloid progenitors, lymphoid progenitors, myeloblasts, monocytes, small lymphocytes, B cell progenitors, and T cell progenitors. Markers for the above-referenced cells are well known in the art.

In some versions of the invention, the genetically modified cell is a T cell or a precursor thereof. Exemplary T cells include CD4+ T cells, CD8+ T cells, γδ T cells, regulatory (suppressor) T cells. Exemplary precursors of T cells include hematopoietic stem cells, pluripotent stem cells, multipotent progenitors, lymphoid progenitors, and T cell progenitors. Markers for the above-referenced cells are well known in the art.

In some versions, the genetically modified cell may be a neuron or a precursor of a neuron and/or a glial cell or a precursor of a glial cell. In some versions, the genetically modified cell may be an astrocyte.

In some versions of the invention, the genetically modified cell is of a cell type susceptible to infection with a virus or a precursor of a cell type susceptible to infection with a virus. The phrase "of a cell type susceptible to infection with a virus" as applied to a particular genetically modified cell means that the cell type in unmodified form is susceptible to infection with the virus, whether or not the particular genetically modified cell itself is susceptible to infection with the virus. The term "susceptible" in the phrase "of a cell type susceptible to infection with a virus" means that the cell is capable of being infected with a virus. The term "infected" in the phrase "of a cell type susceptible to infection with a virus" means that the virus is capable of entering a cell of the cell type and, at least in the case of retroviruses, integrating part or all of its genome (in DNA form) into the cell's genome as a provirus.

In some versions, the virus to which the cell type of the genetically modified cell is susceptible to infection is a lentivirus. In some versions, the lentivirus is a primate immunodeficiency virus. Exemplary primate immunodeficiency viruses to which the cell type of the genetically modified cell is susceptible to infection include human immunodeficiency virus (HIV), such as HIV-1 and HIV-2, and simian immunodeficiency virus (SIV). In some versions, the lentivirus is a feline immunodeficiency virus. In some versions, the lentivirus is a bovine immunodeficiency virus.

In some versions, the virus to which the cell type of the genetically modified cell is susceptible to infection is a deltaretrovirus. In some versions, the deltaretrovirus is a primate T-lymphotropic virus. Exemplary primate T-lymphotropic viruses to which the cell type of the genetically modified cell is susceptible to infection include human T-lymphotropic virus (HTLV), including HTLV-1, HTLV-2, HTLV-3, and HTLV-4, and simian T-lymphotropic virus (STLV), including STLV-1, STLV-2, STLV-3, and STLV-5.

Methods of Treatment

Another aspect of the invention is directed to methods of treating subjects infected with a lentivirus. The methods include introducing a genetically modified cell of the invention in a subject infected with a lentivirus.

The lentivirus to which the treated subject is infected may comprise any lentivirus, including any of those explicitly described herein.

The term "introduce" used with respect to treating a subject encompasses introducing genetically modified cells generated outside the body of the subject (in vitro or ex vivo) into the body, as well as generating genetically modified cells inside the body of the subject (in vivo). In some versions, the introducing comprises introducing the cell into the bloodstream of the subject. In some versions, the introducing comprises injecting or infusing the cell into the bloodstream of the subject.

The genetically modified cell introduced in the subject may comprise any genetically modified cell of the invention.

The genetically modified cell introduced in the subject is preferably of a cell type susceptible to infection with the lentivirus or a precursor of a cell type susceptible to infection with the lentivirus.

The genetically modified subject may be a mammal. In some versions, the subject is a primate. In some versions, the subject is a simian. In some versions, the subject is a human. In some versions, the subject is a non-human simian. In some versions, the subject is a feline. In some versions, the subject is a bovine. In some versions, the subject is a canine.

The genetically modified cell may be a mammalian cell. In some versions, the cell is a primate cell. In some versions, the cell is a simian cell. In some versions, the cell is a human cell. In some versions, the cell is non-human simian cell. In some versions the cell is a feline cell. In some versions the cell is a bovine cell. In some versions, the cell is a canine cell.

In some versions, the genetically modified cell is autologous to the treated subject. In some versions, the genetically modified cell is non-autologous to the treated subject.

The terms "treating," or "ameliorating" and similar terms used herein may include prophylaxis and full or partial treatment. The terms may also include reducing symptoms, ameliorating symptoms, reducing the severity of symptoms, reducing the incidence of the disease, or any other change in the condition of the patient, which improves the therapeutic outcome. In some versions of the invention, the treating comprises increasing the proportion of genetically modified cells in the subject over a period of time. The period of time may comprise from 1 day, to a month, several months, or a year or more. In some versions of the invention, the treating comprises reducing the viral load of the lentivirus in the subject.

Some versions of the invention comprise isolating a cell from the subject, genetically modifying a native CCNT1 and/or XPO1 gene in the cell to generate a genetically modified cell of the invention, and introducing the genetically modified cell in the subject. Some versions may further comprise expanding the genetically modified cells ex vivo prior to introducing the expanded genetically modified cells in the subject. In exemplary versions, the subject is a human, the lentivirus is a primate immunodeficiency virus, such as HIV-1 or HIV-2, and the cell is a $CD4^+$ T cell.

Methods for isolating cells from a subject, expanding the cells ex vivo after genetic modification, and introducing the expanded cells in the subject are well known in the art. See Tricket et al. 2002 (Trickett A E, Kwan Y L, Cameron B, Dwyer J M. Ex vivo expansion of functional T lymphocytes from HIV-infected individuals. J Immunol Methods. 2002 Apr. 1; 262(1-2):71-83), Lieberman et al. 1997 (Lieberman J, Skolnik P R, Parkerson G R 3rd, Fabry J A, Landry B, Bethel J, Kagan J. Safety of autologous, ex vivo-expanded human immunodeficiency virus (HIV)-specific cytotoxic T-lymphocyte infusion in HIV-infected patients. Blood. 1997 Sep. 15; 90(6):2196-206), van Lunzen et al. 2007 (van Lunzen J, Glaunsinger T, Stahmer I, von Baehr V, Baum C, Schilz A, Kuehlcke K, Naundorf S, Martinius H, Hermann F, Giroglou T, Newrzela S, Müller I, Brauer F, Brandenburg G, Alexandrov A, von Laer D. Transfer of autologous gene-modified T cells in HIV-infected patients with advanced immunodeficiency and drug-resistant virus. Mol Ther. 2007 May. 15(5):1024-33), Tebas et al. 2014 (Tebas P, Stein D, Tang W W, Frank I, Wang S Q, Lee G, Spratt S K, Surosky R T, Giedlin M A, Nichol G, Holmes M C, Gregory P D, Ando D G, Kalos M, Collman R G, Binder-Scholl G, Plesa G, Hwang W T, Levine B L, June CH. Gene editing of CCR5 in autologous CD4 T cells of persons infected with HIV. N Engl J Med. 2014 Mar. 6; 370(10):901-10), von Laer et al. 2006, (von Laer, D, Hasselmann, S and Hasselmann, K (2006). Gene therapy for HIV infection: what does it need to make it work? J Gene Med 8: 658-667), and Levine et al. 2006 (Levine, B L, Humeau, L M, Boyer J, Macgregor, R R, Rebello, T, Lu, X et al. (2006). Gene transfer in humans using a conditionally replicating lentiviral vector. Proc Natl Acad Sci USA 103: 17372-17377).

An exemplary method for isolating cells from a subject, expanding the cells ex vivo after genetic modification, and introducing the expanded cells is as follows. Patients undergo lymphapheresis, and about $1.0 \times 10^{10}$ or more mononuclear cells are collected. After overnight storage, cells are washed with a CytoMate device (Baxter, Heidelberg, Germany) and incubated with magnetic beads labeled with anti-CD8 antibodies (Miltenyi Biotech, Bergisch-Gladbach, Germany) for 30 minutes. After a second wash step, CD8+ cells are depleted using the CliniMacs (Miltenyi Biotech). A maximum of $2.5 \times 10^8$ CD3+ cells are then incubated with anti-$CD3^3/_a$nti-CD28-coated Xcyte Dynabeads (Xcyte Therapies, Seattle, WA) at a CD3+cell to bead ratio of 1:3 for 30 minutes on a lab rotator. Labeled cells are then enriched via the MaxSep permanent magnet (Baxter) and carefully resuspended in X-Vivo 15 medium (Cambrex) complemented with 100 U/ml rhIL-2 (Chiron, Munich, Germany), 2 mM 1-glutamine (Cambrex), 5% human serum (Cambrex), and 20 mM HEPES (Invitrogen, Karlsruhe, Germany) at a cell density of $5 \times 10^5$ cells/ml and seeded into tissue culture bags (Baxter). A mixture of antivirals (1 µM nelfinavir (Viracept), Roche, Basel, Switzerland; 0.33 µM amprenavir (Agenerase), GlaxoSmithKline, Munich, Germany; 10 µg/ml T-20 (Fuzeon), Roche) are added to the cell suspension to avoid viral replication. After 4 days of culture at 37° C. and 5% $CO_2$, Xcyte Dynabeads are removed from the cell suspension. Cells are then subject to gene editing to generate the genetically modified cells of the invention. After gene editing, the cells are expanded for a maximum of 7 days in a static culture until the required cell number is achieved. Finally, the remaining Xcyte Dynabeads are removed and cells are harvested with a Cyto-Mate device and cryopreserved in dimethyl sulfoxide (WAK Chemie, Steinbach, Germany), PlasmaLyte A (Baxter), Plasmasteril (6% hydroxyethyl starch; Fresenius Kabi, Bad Homburg, Germany), and human serum albumin (20%, Baxter) for long-term storage. The genetically modified cells are infused in the patient in an amount of from about $1 \times 10^8$ to about $1 \times 10^{12}$, such as from about $1 \times 10^9$ to about $1 \times 10^{11}$. Amounts above and below these amounts are also acceptable.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Editing Host Factors to Silence HIV Gene Expression
Methods

Cell lines and cell culture. Jurkat E6.1 T-lymphocyte (J.E6-1) cells were obtained from the American Type Culture Collection (ATCC) and were cultured in RPMI 1640 medium (Gibco) supplemented with 10% fetal bovine serum (FBS, Sigma), 1% L-glutamine (Sigma), and 1% penicillin-streptomycin antibiotics. 293T cells were cultured in Dulbecco's modified Eagle's medium (DMEM) supplemented with 10% fetal bovine serum, 1% L-glutamine and penicillin-streptomycin antibiotics. Cells were maintained at 37° C. and 5% $CO_2$ in a humidified incubator.

Gene Editing. CRISPR-Cas9 and homology directed repair (HDR) were used to edit hCCNT1 and hXPO1 to generate genetically modified CCNT1 and XPO1 genes of the invention.

Figure 4:
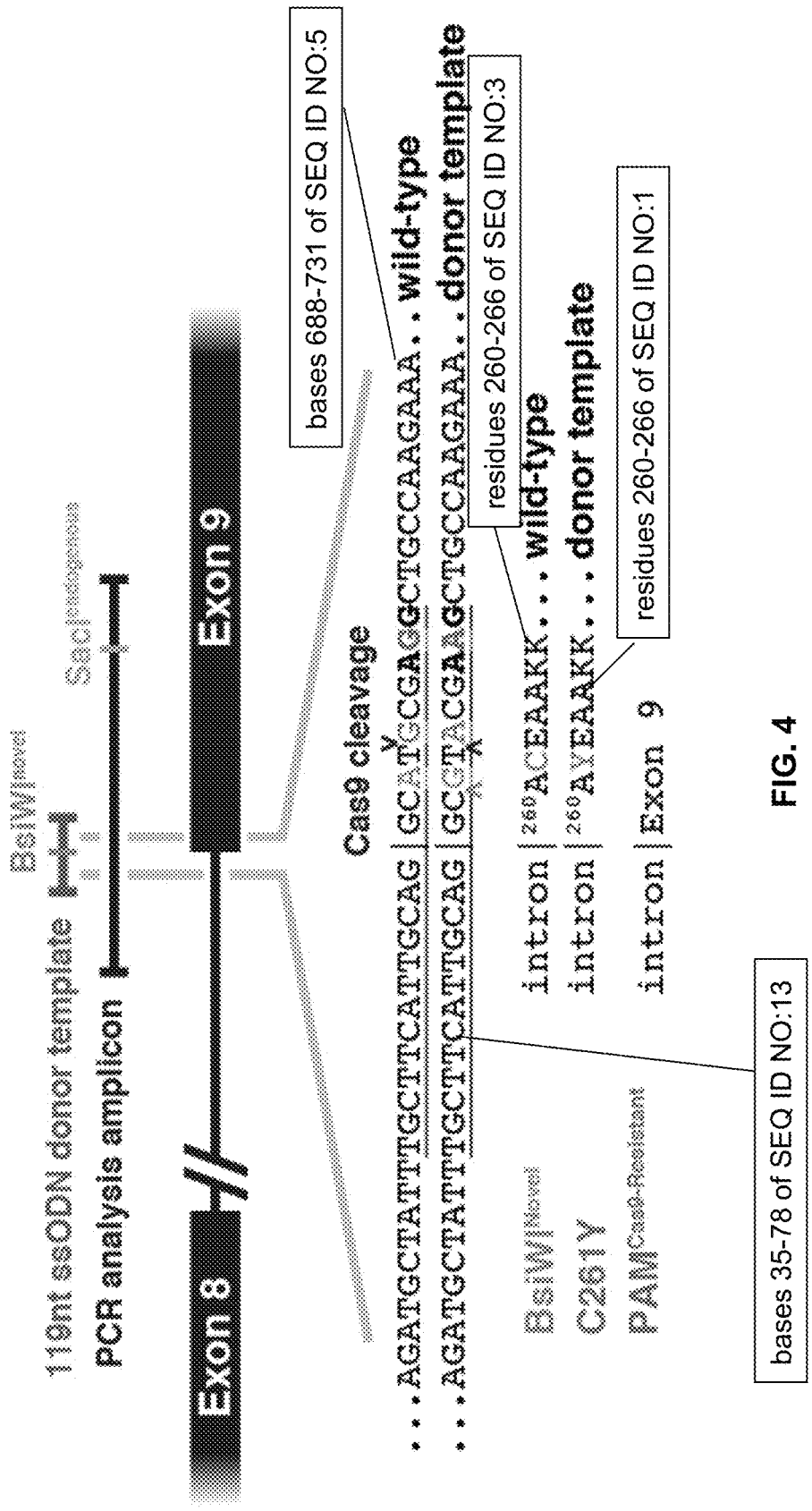

The method used for editing hCCNT1 is depicted in FIG. 4. The HDR donor template for editing hCCNT1 had a sequence represented by SEQ ID NO:13

(SEQ ID NO: 13)
GTGTTTTTTTATTTAGTAAATTACCTAAGTAAAGAGATGCTATTTGCTTCA

TTGCAGGCgTaCGAaGCTGCCAAGAAAACAAAAGCAGATGACCGAGGAACA

GATGAAAAGACTTCAGA

Figure 5A:
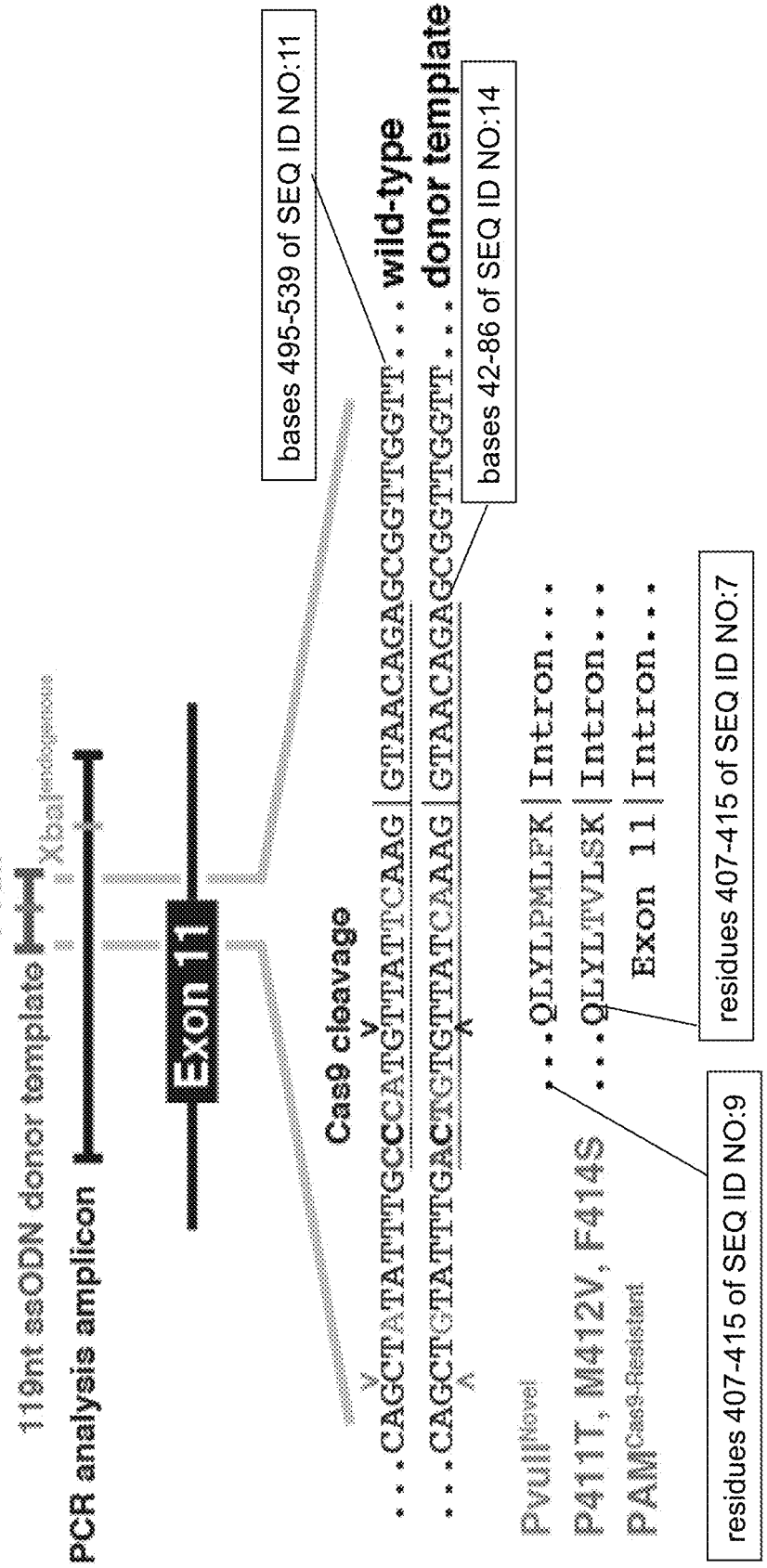
Figure 5B:
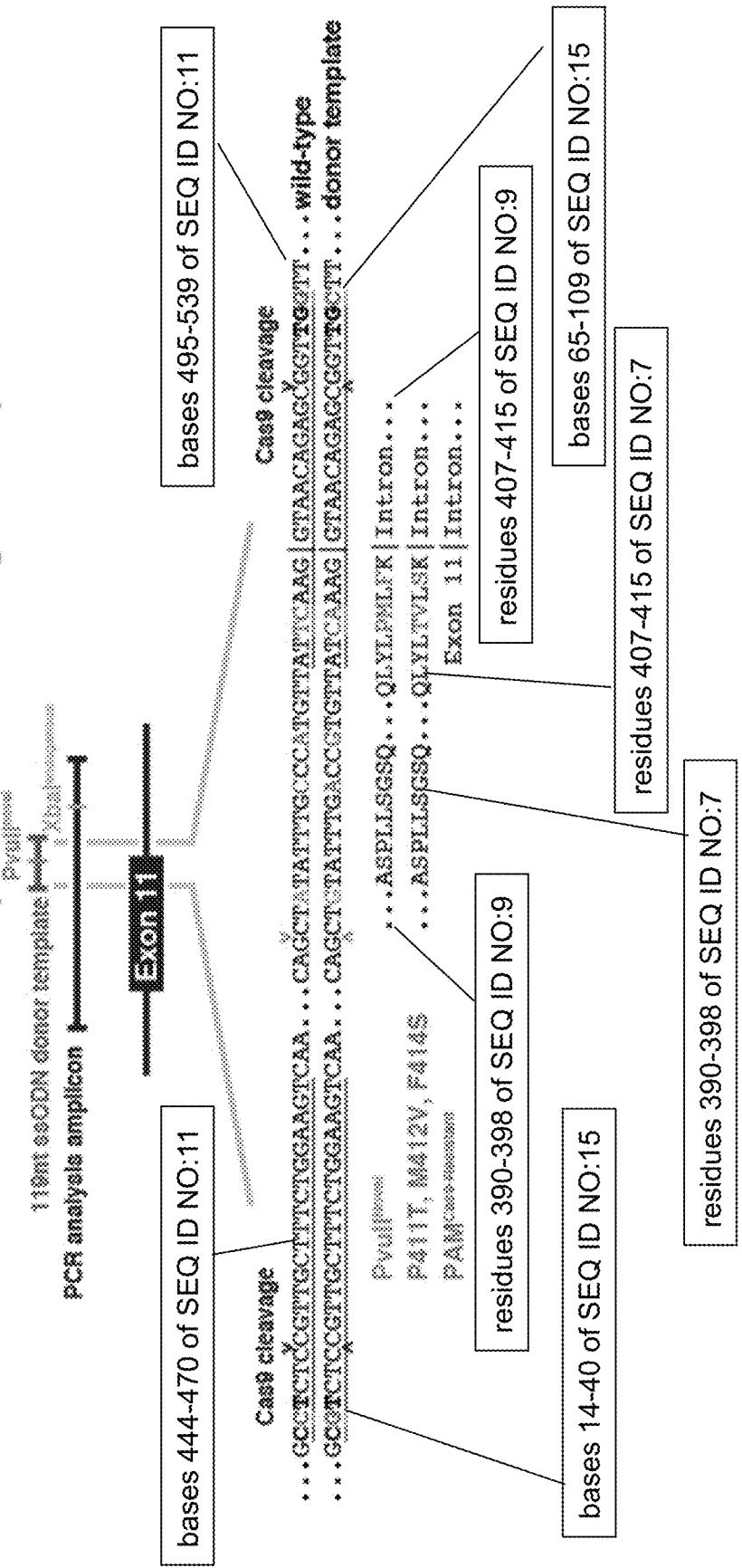

Methods for editing hXPO1 are depicted in FIGS. 5A and 5B. These methods used two different donor templates. The donor template used in the method depicted in FIG. 5A had a sequence represented by SEQ ID NO:14:

(SEG ID NO: 14)
TGCTTTCTGGAAGTCAACATTTTGATGTTCCTCCCAGGAGACAGCTGTAT

TTGACTGTGTTATCAAAGGTAACAGAGCGGITGGITGAGTGTTCTICCTG

TTGCATACTGTGGTTTTGA

The donor template used in the method depicted in FIG. 5B had a sequence represented by SEQ ID NO:15:

(SEQ ID NO: 15)
ATTCTCTACATCTGCgTCTCCGTTGCTTTCTGGAAGTCAACATTTTGATGT

TCCTCCCAGGAGACAGCTgTATTTGaccgtgttatcaAAGGTAACAGAGCG

GTTGcTTGAGTGTTCTT

Alt-R™ recombinant S.p. Cas9 nuclease-3NLS (IDT, #1074181), Alt-R™ CRISPR-Cas9 crRNA (IDT, custom ordered), ATTO™-550 labeled Alt-R™ tracrRNA (IDT, #1075928), and Alt-RT$^M$ Cas9 Electroporation Enhancer reagent (IDT, #1075915), and nuclease-free IDTE pH 7.5 buffer (IDT, #11-01-02-02) were prepared according to the manufacturer's instructions as described in Integrated fDNA Technologies User Guide ("Alt-R™ CRISPR-Cas9 System: Delivery of ribonucleoprotein complexes in Jurkat T cells using Neon® Transfection System," published on the world wide web at idtdna.com). The indicated 119-nt single-stranded oligodeoxynucleotide (ssODN) templates for homology-directed repair (HDR) were custom ordered (Sigma) and prepared as a 100 uM stock solution in TE buffer.

Jurkat cell culture preparations, crRNA:tracrRNA duplex preparations, and ribonucleoprotein (RNP) complex preparations were performed according to the reagent manufacturer's instructions in the Integrated DNA Technologies User Guide. The electroporations and final delivered material mixtures were performed according to the manufacturer's instructions in the Integrated DNA Technologies User Guide with slight modification to include ssODN HDR donor templates.

For each electroporation reaction, the crRNA:tracrRNA duplexes were assembled by combining 2.2 μL 200 μM crRNA stock, 2.2 μL 200 μM tracrRNA stock, and 5.6 nuclease-free IDTE buffer for a final volume of 10 μL. Combined reagents were heated to 95° C. for 5 minutes in a bench-top thermocycler and removed to passively cool to room temperature.

For each electroporation reaction, the ribonucleoprotein (RNP) complexes were assembled by combining 0.3 μL rCas9 and 0.2 μL resuspension buffer R for a final volume of 0.5 μL which was subsequently mixed with 0.5 μL of the prepared crRNA:tracrRNA duplex mixtures. This 1 μL total RNP mixture was incubated for approximately 15 minutes at room temperature.

For each electroporation reaction, $5 \times 10^5$ Jurkat cells were washed with 1× PBS and resuspended in 8 μL resuspension buffer R (Invitrogen). 8 μL cell suspensions were combined with 1 μL of the prepared total RNP mixture, 2 μL of the prepared 10.8 μM Electroporation Enhancer, and 1 uL 100 μM ssODN HDR template for a total of 12 μL total. Negative controls for genome editing were included by substituting the crRNA:tracrRNA duplexes from the total RNP mixture with 10 μL nuclease-free IDTE buffer.

These reagents were delivered to J.E6-1 cells using the Neon® Transfection System and Neon® Transfection 10 μL Kit (Invitrogen) according to manufacturer's instructions in the Integrated DNA Technologies User Guide. Electroporation parameters were 1600 V, 10-ms pulse width, 3 pulses and electroporated cells were cultured post-electroporation in pre-warmed antibiotic-free media (RPMI 1640 supplemented with 10% FBS) according to the manufacturer's instructions. Cells were subsequently either bulk-sorted by fluorescence-associated cell sorting (FACS) to concentrate ATTO™-550 positive cells in antibiotic-replete media (RPMI 1640 supplemented with 10% FBS and 1% penicillin-streptomycin-L-glutamine) or unsorted cell cultures were directly screened for ssODN-mediated HDR. Cell populations exhibiting positive HDR sequences based on described screening strategies were subsequently single-cell cloned, screened, and subsequently analyzed.

Cell proliferation assays. $5.0 \times 10^4$ cells per 1 mL were plated in 12-well tissue culture dishes and maintained under normal (37° C./5% $CO_2$) culture conditions. At 4 and 6 days post-plating, cells were resuspended to homogenized suspensions and stained with trypan blue (Sigma) to label any dead cells with unstained cells and enumerated using a hemacytometer.

Preparation of virus stocks. 2-color HIV-1 latency reporter virus ("Dual Reporter Virus") stocks were generated by co-transfecting 293T producer cells using polyethylenimine (PEI; catalog no. 23966. Polysciences, Inc.) and the following plasmids at a 4:2:1 ratio: pE-/EF1a-mChe/ eGFP reporter (Calvanese et al. 2013), 2000 ng psPax2, and 1000 ng pMD.G encoding VSV-G (Ory et al. 1996). Media was exchanged 6 h post-transfection with cell culture supernatants harvested at 48 h, filtered to prevent cell contamination, aliquoted, and stored at −20° C.

For single-round primate lentivirus reporter stocks, 293T cells were co-transfected with plasmids encoding HIV-2.ROD and SIVagm.Tan-1 Env-deficient eGFP-encoding lentiviral reporters (Kane et al. 2013) at a 9:1 ratio with pMD.G encoding VSV-G.

2-color HIV-1 gene expression reporter virus ("Early-Late Reporter Virus") stocks were generated by co-transfecting 293T producer cells using PEI, as above, and the following plasmids at a 4:4:1 ratio: pNL4-3 E-R-/Gag(MA-mVenus-CA)/mChe (Knoener et al., 2017; 3×CFP gene cassette exchanged for a single mVenus reporter gene using standard molecular cloning techniques), psPax2, and pMD.G encoding VSV-G.

For all virus preparation transfections, media was exchanged at approximately 4 hours post-transfection with cell culture supernatants harvested at approximately 48 hours post-transfection, filtered to prevent cell contamination, aliquoted, and stored at ~20° C.

Viral infectivity and gene expression assays. For reporter virus experiments, $1.0 \times 10^6$ cells were infected with equivalent amounts of virus at a multiplicity of infection of ~0.5, with cells transferred to microcentrifuge tubes at 24 hours post-infection, pelleted by centrifugation (500×G for 10 min at RT), washed with 1× PBS, and resuspended in fresh medium. 36 h post-treatment with DMSO, cells were transferred to fresh microcentrifuge tubes and pelleted by centrifugation (500×G for 10 min at RT). Supernatants were removed and cells were subsequently washed twice with 1× PBS, stained with Ghost 780 cell viability dye (Tonbo Biosciences) and washed according to the manufacturer's instructions, fixed with 4% reconstituted paraformaldehyde (PFA) and washed thrice with 1× PBS. Cells were analyzed using an analysis flow cytometer (LSRII, BD biosciences) gating for single, viable cells.

For early-late reporter virus experiments, $1.0 \times 10^6$ cells were infected with equivalent amounts of virus at a multiplicity of infection of ~0.1 or ~0.5. 48 hours post-infection, cells were transferred to microcentrifuge tubes and pelleted by centrifugation (500×G for 10 min at RT). Supernatants were removed and cells were subsequently washed twice with 1× PBS, stained with Ghost 780 cell viability dye (Tonbo Biosciences, San Diego, CA), and washed according to the manufacturer's instructions, fixed with 4% reconstituted paraformaldehyde (PFA) and washed thrice with 1× PBS. Cells were analyzed using an analysis flow cytometer (Attune N×T, Thermo Fisher Scientific, Waltham, MA) gating for single, viable cells.

All flow cytometry plots and gated cell statistics were generated using flow cytometry analysis software (FlowJo, world wide web at flojo.com).

Transfection-based Tat activity assay. For transient promoter activation assays, Jurkat cells ($5.0 \times 10^5$ cells per well) were transfected using the Neon electroporation system (Invitrogen) following manufacturer's instructions using 1600 volts, a pulse width of 10 ms and 3 pulses. Each transfection mix consisted of 75 ng of plasmid encoding an HIV-1 U3 Tat/TAR-responsive secreted gaussia luciferase (gLuc) reporter (Nekhai et al. 2006), 250 ng of pmCherry expression plasmid (pmCherry-C1, Takara Bio), 75 ng of a cypridina expression plasmid (tk-Cluc, New England Biolabs, NEB) with or without plasmids encoding CCNT1 variants or Tat expression plasmids at 1200 and 25 ng/well, respectively. Vector plasmid DNA or Calf thymus DNA (NEB) was used to maintain a constant 2.5 plasmid DNA per transfection. 24 hours post-transfection, 10 μl of media was removed, diluted with 40 μl of PBS and assayed for secreted gaussia luciferase (gluc) by injecting 30 μl coelenterazine solution (Renilla luciferase assay system, Promega, Madison, WI), waiting 1.6 s and then reading luminescence for 1 s. Secreted cypridina luciferase (cLuc) activity from the internal control plasmid was determined using the cypridina Luciferase kit (NEB) according to the manufacturer's instructions using the same injection conditions as for gLuc. The activity of the retroviral promoter in each well was then determined as the ratio of gLuc:cLuc.

Analysis of genomic DNA modifications to CCNT1 and XPO1. Genomic DNA was extracted from prepared bulk heterogeneous or clonal Jurkat cell lines. Briefly, Jurkat cells were washed with phosphate-buffered saline (PBS) in microcentrifuge tubes, resuspended in 10 μL 1× polymerase chain reaction (PCR) buffer (GoTaq Green Buffer, Promega) in standard PCR tubes, and subjected to a single freeze-thaw cycle at −80° C. 1 μL proteinase K (New England BioLabs, NEB) were added to each tube and incubated at 65° C. for 60 min, 95° C. for 15 min, and were maintained at 4° C. During 4° C. hold, the remaining 40 μL for a 50 μL PCR reaction (GoTaq Flexi Kit, Promega) were added to each tube, using the following CCNT1 or XPO1 primer sets:

CCNT1 forward screening primer: 5'-TGA GAT TAG AAG TAG GCT TGA GAG G-3' (SEQ ID NO:16). CCNT1 reverse screening primer: 5'-GCT AAA TTC TCA CTA GTC CGA TGA C-3' (SEQ ID NO:17). XPO1 forward screening primer: 5'-TTC TCT CCT CTG TGA TGG TAC ATT T-3' (SEQ ID NO:18). XPO1 reverse screening primer: 5'-TCA AGA TTG TAG TGA GCT ATG ACC A-3' (SEQ ID NO:19).

CCNT1 or XPO1 genomic loci amplicons were amplified using the following PCR cycle conditions: CCNT1 PCR cycle conditions: 98° C. for 2 min, 98° C. for 15 sec, 66° C. for 45 sec, 72° C. for 2 min, repeat steps 2-4 an additional 35 times, 72° C. for 10 min, 4° C. hold. XPO1 PCR cycle conditions: 98° C. for 2 min, 98° C. for 15 sec, 60° C. for 45 sec, 72° C. for 2 min, repeat steps 2-4 an additional 35 times, 72° C. for 10 min, 4° C. hold.

Restriction enzyme digestion reactions containing candidate CCNT1 genomic DNA amplicons were carried out following the manufacturer's recommended protocol with BsiWI-HF enzyme (NEB) or no enzyme controls. Predicted BsiWI digestion products were based on the FIG. 4 design scheme: 712 bp and 288 bp. Restriction enzyme digestion reactions containing candidate XPO1 genomic DNA amplicons were carried out following the manufacturer's recommended protocol with PvuII enzyme (NEB) or no enzyme controls. Predicted PvuII digestion products were based on the FIG. 5A or FIG. 5B design scheme: 497 bp and 480 bp.

DNA amplicons and/or DNA products following restriction enzyme digestion were resolved using standard agarose gel electrophoresis.

Results

The invention encompasses the generation of primary mammalian cells or cell lines wherein orthologs of conserved genes known to regulate human immunodeficiency virus type 1 (HIV-1) gene expression are altered at their native loci within chromosomes in order to render the cells intrinsically resistant to HIV-1 replication in vitro and in vivo. This strategy also blocks replication of other important human retroviral pathogens including HIV type 2 (HIV-2) and human T lymphotropic virus types 1 and 2 (HTLV-1 and HTLV-2), as well as related retroviruses of the genuses lentiviridae and deltaretoviridae that cause immunodeficiency, cancers, or other diseases in other animals. The invention is premised on our discovery that blocks to HIV-1 replication observed in mice can be made manifest in human cells using a gene knock-in strategy, with little to no discernable effect on host biology.

In people infected with HIV-1, the human CCNT1 (hCCNT1) transcription factor is recruited by the viral Tat protein to the viral promoter in order to activate robust viral mRNA transcription (Nekhai et al. 2006, Wei et al. 1998) (FIG. 3, panel A). By contrast, in mice mouse CCNT1 (mCcnt1) binds poorly to Tat, a defect previously mapped to a single species-specific amino acid (tyrosine at position 261 instead of cysteine as found in hCCNT1; a difference herein referred to as "C261Y") (Bieniasz et al. 1998, Garber et al.

1998) (FIG. 3, panel B). Similarly, the human XPO1 (hXPO1) nuclear export receptor is recruited by the viral Rev protein to intron-retaining viral mRNAs to mediate their nuclear export and hence ensure late stage gene expression needed to accomplish infectious virion production (Fornerod et al. 1997, Neville et al. 1997, Pollard et al. 1998) (FIG. 3, panel A). By contrast, mouse XPO1 (mXpo1) interacts poorly with Rev/RNA complexes due to a species-specific cluster of three mXPo1-specific amino acids; threonine-411 instead of proline, valine-412 instead of methionine, and serine-414 instead of phenylalanine (Elinav et al. 2012, Sherer et al. 2011) (FIG. 3, panel C). Thus, in mouse cells HIV-1 is unable to express viral gene products and infectious virus particles cannot be generated.

Figure 6:
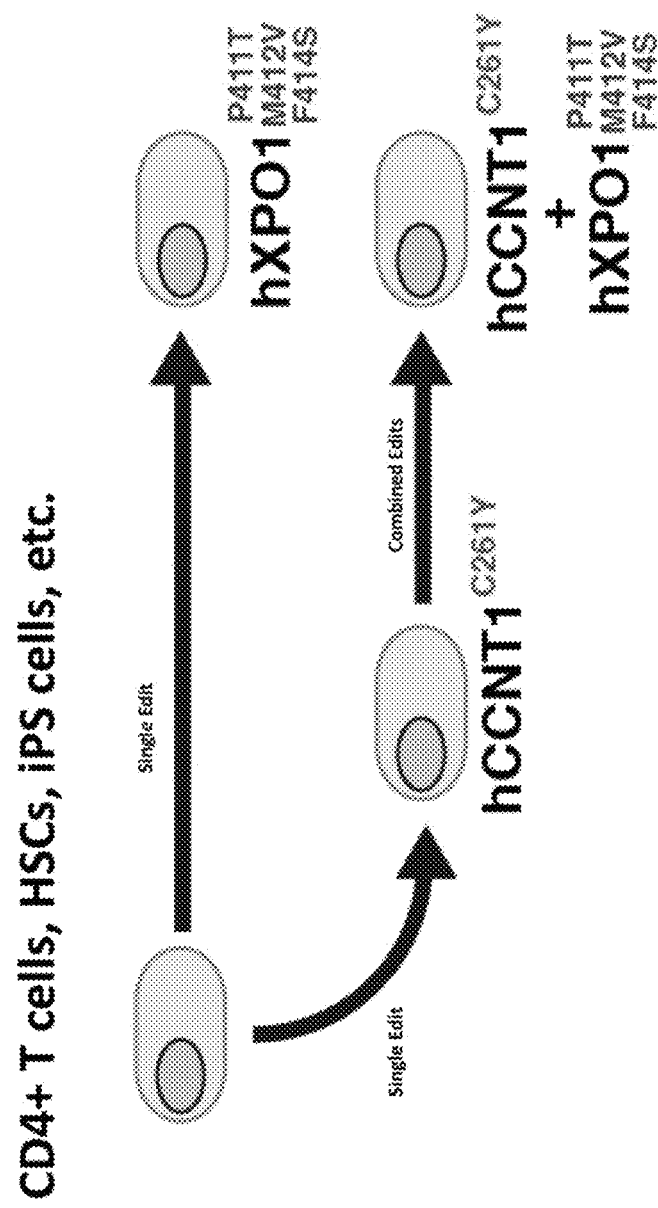

To determine if naturally-occurring, species-specific genetic blocks to HIV-1 gene expression can be made manifest in human cells, we designed and engineered CRISPR/Cas9 clonal human Jurkat E6-1 T cell lines carrying homozygous hCCNT1-C261Y alleles and compared them to wild-type parental cells in HIV-1 gene expression assays. A depiction of how the hCCNT1-C261Y Jurkat cells were modified is shown in FIGS. 4 and 6. A depiction of how cells can similarly be modified to encode hXPO1-P411T-M412V-F414S is shown in FIGS. 5 and 6. FIG. 6 also shows how two or more gene edits (e.g., modifying both hCCNT1 and hXPO1) can be multiplexed to block multiple stages of the HIV-1 replication cycle in the same cell. Two hCCNT1-C261Y cell lines (clones 4.7F and 4.8C) were isolated and characterized. These cells proliferated identically to parental cells, thus demonstrating that the C261Y hCCNT1 codon change has no effect on basic features of cellular metabolism (FIG. 7, panel A). In contrast, clones 4.7F and 4.8C potently restricted HIV-1 Tat-dependent gene expression (FIG. 7, panels B and C).

We confirmed that the hCCNT1-C261Y block specifically inhibited HIV-1 Tat function using two independent HIV-1 gene reporter assays (FIG. 7, panels B and C). First, wild-type and hCCNT1-C261Y cells were infected using "single-round" HIV-1 reporter viruses that report on both HIV-1 Tat-dependent gene expression (based on GFP synthesis) and Tat-independent gene expression (based on mCherry synthesis) (Calvanese et al. 2013). Similar percentages of cells for all three cell lines exhibited constitutive mCherry reporter gene expression at 2.5 days post-infection, thus confirming equivalent levels of infection (FIG. 7, panel B, red bars). By contrast, the hCCNT1-C261Y cells were highly resistant to Tat activity as illustrated by a >16-fold drop to Tat-dependent GFP expression (FIG. 7, panel B, green bars). Second, to address specificity we co-transfected wild-type or hCCNT1-C261Y cell lines with DNA gene expression plasmids encoding Tat and a Tat-responsive Luciferase reporter, with or without plasmids encoding wild-type hCCNT1 (FIG. 7, panel C). Tat activity was almost completely abolished in both hCCNT1-C261Y cell lines compared to parental cells but could be rescued by co-expressing wild-type hCCNT1 (FIG. 7, panel C). Collectively, these data demonstrate that Tat-dependent viral gene expression is largely abolished in human cells simply by altering a single codon in CCNT1 to encode tyrosine and not cysteine.

Because many if not all lentiviruses resemble HIV-1 in their dependence on Tat-CCNT1 interactions in order to activate viral gene expression, we also tested if hCCNT1-C261Y modified cells could suppress HIV-2 and the simian immunodeficiency virus of the African green monkey (SIVagm) Tat-dependent viral gene expression using previously validated GFP reporter viruses (Kane et al. 2013) (FIG. 8). HIV-2 and SIVagm Tat-dependent viral gene expression was highly suppressed in the 4.7F hCCNT1-C261Y Jurkat T cell line. These results illustrate broad-spectrum antiviral potential for hCCNT1-C261Y gene modifications.

C261Y alleles predict similar results with hXPO1, wherein clonal human Jurkat E6-1 T cell lines carrying homozygous hXPO1 genes encoding hXPO1 with either a P411T mutation (hXPO1-P411V), a M412V mutation (hXPO1-M412V), a F414S mutation (hXPO1-F414S), P411T and M412V mutations (hXPO1-P411T-M412V), P411T and F414S mutations (hXPO1-P411T-F414S), M412V and F414S mutations (hXPO1-M412V-F414S), or P411T, M412V, and F414S mutations (hXPO1-P411T-M412V-F414S) are predicted to proliferate identically to parental cells with one or more combination of the three variant amino acids restricting HIV-1, HIV-2, and SIV late stage gene expression.

We sought to define an analytical method by which HIV-1 resistance profiles can be resolved and characterized in non-clonal T cell populations. To this end, we mixed wild-type and hCCNT1-C261Y cells at defined ratios (20:80, 50:50, and 80:20) to simulate a heterogeneous cell mixture using known clonal cell lines. Next, we infected these mixed cultures with a HIV-1 reporter virus that distinguishes between early and late viral gene expression (Early-Late Reporter Virus) and examined the HIV resistance profile at a population level by flow cytometric analyses (FIGS. 9B-D). We confirmed the relative abundance of wild-type and hCCNT1-C261Y alleles in each cell mixture by PCR and restriction enzyme digestion reactions (FIG. 9A). In this analysis, we defined a gating strategy (FIG. 9B) that enables us to resolve population-level changes to the percentages of cells expressing no viral genes, only early viral genes, or early and late viral genes ("Gate 1", "Gate 2", and "Gate 3", respectively). Given the ability of hCCNT1-C261Y cells to resist HIV-1 gene expression, we observed a striking and titratable reduction to the percentages of cells expressing both early and late viral genes as the relative abundance of the resistant cell population in the mixtures is increased (FIGS. 9C and 9D). In conclusion, we present a method to quantify HIV resistance in heterogeneous cell populations using defined mixtures clonal Jurkat populations.

Using the population-level flow cytometry analysis described (FIGS. 9A-9D), we examined whether cells modified to produce hXPO1-P411T-M412V-F414S could also imbue HIV-1 resistance to Jurkat T cells. According to the design scheme presented above (FIGS. 5A and 6), we carried out CRISPR/Cas9 gene editing in a similar manner to induce hXPO1-P411T-M412V-F414S gene modifications, and infected the heterogeneous cell mixtures, or wild-type control cells, with the early-late reporter virus with two virus doses. We confirmed the presence of hXPO1-P411T-M412V-F414S modifications in the CRISPR/Cas9-treated cells by PCR and restriction enzyme digestion reactions (FIG. 10A) and evaluated the infected cell populations according to the gating strategy described for FIG. 10B. Consistent with a block to HIV-1 Rev function, we observed a reduction to the percentages of cells expressing both early and late genes and an approximately similar increase to the cells expressing only early genes (FIGS. 10C and 10D). In sum, we demonstrate that species-informed modifications to hXPO1 can be employed to repress HIV-1 gene expression.

REFERENCES

Bieniasz P D, Grdina T A, Bogerd H P, Cullen B R. Recruitment of a protein complex containing Tat and cyclin T1 to TAR governs the species specificity of HIV-1 Tat. EMBO J. 1998 Dec. 1; 17(23):7056-7065. PMCID: PMC1171053

Bieniasz P D, Grdina T A, Bogerd H P, Cullen B R. Analysis of the effect of natural sequence variation in Tat and in cyclin T on the formation and RNA binding properties of Tat-cyclin T complexes. J Virol. 1999 Jul; 73(7):5777-5786. PMCID: PMC112638

Calvanese V, Chavez L, Laurent T, Ding S, Verdin E. Dual-color HIV reporters trace a population of latently infected cells and enable their purification. Virology. 2013 November; 446(1-2):283-292. PMCID: PMC4019006

Cho W-K, Jang M K, Huang K, Pise-Masison C A, Brady J N. Human T-lymphotropic virus type 1 Tax protein complexes with P-TEFb and competes for Brd4 and 7SK snRNP/HEXIM1 binding. J Virol. 2010 Dec; 84(24): 12801-12809. PMCID: PMC3004308

Elinav H, Wu Y, Coskun A, Hryckiewicz K, Kemler I, Hu Y, Rogers H, Hao B, Ben Mamoun C, Poeschla E, Sutton R. Human CRM1 augments production of infectious human and feline immunodeficiency viruses from murine cells. J Virol. 2012 November; 86(22):12053-12068. PMCID: PMC3486471

Feng Y, Broder C C, Kennedy P E, Berger E A. HIV-1 entry cofactor: functional cDNA cloning of a seven-transmembrane, G protein-coupled receptor. Science. 1996 May 10; 272 (5263):872-877.

Fornerod M, Ohno M, Yoshida M, Mattaj I W. CRM1 Is an Export Receptor for Leucine-Rich Nuclear Export Signals. Cell. 1997 Sep. 19; 90(6):1051-1060.

Garber M E, Wei P, KewalRamani V N, Mayall T P, Herrmann C H, Rice A P, Littman D R, Jones K A. The interaction between HIV-1 Tat and human cyclin T1 requires zinc and a critical cysteine residue that is not conserved in the murine CycT1 protein. Genes Dev. 1998 Nov. 15; 12 (22):3512-3527.Fornerod M, Ohno M, Yoshida M, Mattaj I W. CRM1 is an export receptor for leucine-rich nuclear export signals. Cell. 1997 Sep. 19; 90(6):1051-1060. PMID: 9323133

Garber M E, Wei P, KewalRamani V N, Mayall T P, Herrmann C H, Rice A P, Littman D R, Jones K A. The interaction between HIV-1 Tat and human cyclin T1 requires zinc and a critical cysteine residue that is not conserved in the murine CycT1 protein. Genes Dev. 1998 Nov. 15; 12 (22):3512-3527. PMCID: PMC317238

Integrated DNA Technologies User Guide. "Alt-R$^M$ CRISPR-Cas9 System: Delivery of ribonucleoprotein complexes in Jurkat T cells using Neon® Transfection System," published on the world wide web at idtdna.com.

Kane M, Yadav S S, Bitzegeio J, Kutluay S B, Zang T, Wilson S J, Schoggins J W, Rice C M, Yamashita M, Hatziioannou T, Bieniasz P D. MX2 is an interferon-induced inhibitor of HIV-1 infection. Nature. 2013 Oct. 24; 502(7472):563-566.

Knoener R A, Becker J T, Scalf M, Sherer N M, Smith L M. 2017. Elucidating the in vivo interactome of HIV-1 RNA by hybridization capture and mass spectrometry. Scientific Reports 7:16965.

Landau N R, Warton M, Littman D R. The envelope glycoprotein of the human immunodeficiency virus binds to the immunoglobulin-like domain of CD4. Nature. 1988 Jul 14; 334(6178):159-162.

Nagai-Fukataki M, Ohashi T, Hashimoto I, Kimura T, Hakata Y, Shida H. Nuclear and cytoplasmic effects of human CRM1 on HIV-1 production in rat cells. Genes Cells Devoted Mol Cell Mech. 2011 Feb. 16(2):203-216. PMID: 21251165

Mariani R, Chen D, Schröfelbauer B, Navarro F, Konig R, Bollman B, Munk C, Nymark-McMahon H, Landau N R. Species-specific exclusion of APOBEC3G from HIV-1 virions by Vif. Cell. 2003 Jul. 11; 114 (1):21-31. PMID: 12859895

McNatt M W, Zang T, Hatziioannou T, Bartlett M, Fofana I B, Johnson W E, Neil S J D, Bieniasz P D. Species-specific activity of HIV-1 Vpu and positive selection of tetherin transmembrane domain variants. PLoS Pathog. 2009 Feb. 5 (2):e1000300. PMCID: PMC2633611

Nekhai S, Jeang K-T. Transcriptional and post-transcriptional regulation of HIV-1 gene expression: role of cellular factors for Tat and Rev. Future Microbiol. 2006 Dec. 1 (4):417-426. PMID: 17661632

Neville M, Stutz F, Lee L, Davis L I, Rosbash M. The importin-beta family member Crm1p bridges the interaction between Rev and the nuclear pore complex during nuclear export. Curr Biol C B. 1997 Oct. 1; 7 (10):767-775. PMID: 9368759

Ory D S, Neugeboren B A, Mulligan R C. A stable human-derived packaging cell line for production of high titer retrovirus/vesicular stomatitis virus G pseudotypes. Proc Natl Acad Sci USA. 1996 Oct. 15; 93 (21):11400-6.Pollard V W, Malim M H. The HIV-1 Rev protein. Annu Rev Microbiol. 1998; 52:491-532.

Sawyer S L, Wu L I, Emerman M, Malik H S. Positive selection of primate TRIMS alpha identifies a critical species-specific retroviral restriction domain. Proc Natl Acad Sci USA. 2005 Feb. 22; 102 (8):2832-2837. PMCID: PMC549489

Schröfelbauer B, Chen D, Landau N R. A single amino acid of APOBEC3G controls its species-specific interaction with virion infectivity factor (Vif). Proc Natl Acad Sci USA. 2004 Mar. 16; 101 (11):3927-3932. PMCID: PMC374346

Sherer N M, Swanson C M, Hue S, Roberts R G, Bergeron J R C, Malim M H. Evolution of a species-specific determinant within human CRM1 that regulates the post-transcriptional phases of HIV-1 replication. PLoS Pathog. 2011 November; 7(11):e1002395. PMCID: PMC3219727

Stremlau M, Owens C M, Perron M J, Kiessling M, Autissier P, Sodroski J. The cytoplasmic body component TRIM5alpha restricts HIV-1 infection in Old World monkeys. Nature. 2004 Feb. 26; 427(6977):848-853.

Tada T, Kadoki M, Liu Y, Tokunaga K, Iwakura Y. Transgenic expression of the human LEDGF/p75 gene relieves the species barrier against HIV-1 infection in mouse cells. Front Microbiol. 2013; 4:377. PMCID: PMC3865800

Wei P, Garber M E, Fang S M, Fischer W H, Jones K A. A novel CDK9-associated C-type cyclin interacts directly with HIV-1 Tat and mediates its high-affinity, loop-specific binding to TAR RNA. Cell. 1998 Feb. 20; 92(4): 451-462. PMID: 9491887

Zheng Y-H, Yu H-F, Peterlin B M. Human p32 protein relieves a post-transcriptional block to HIV replication in murine cells. Nat Cell Biol. 2003 Jul. 5 (7):611-618.

Zhou M, Lu H, Park H, Wilson-Chiru J, Linton R, Brady J N. Tax interacts with P-TEFb in a novel manner to stimulate human T-lymphotropic virus type 1 transcription. J Virol. 2006 May; 80 (10):4781-4791. PMCID: PMC1472077

EXEMPLARY EMBODIMENTS OF THE INVENTION

Embodiment 1. A genetically modified CCNT1 gene encoding a protein comprising a sequence with at least 80%, at least 85%, at least 90%, or at least 95% sequence identity to SEQ ID NO:1 and comprising a tyrosine at a position corresponding to position 261 of SEQ ID NO:1.

Embodiment 2. The genetically modified CCNT1 gene of embodiment 1, wherein the protein encoded by the genetically modified CCNT1 gene comprises one, some, or all of: an amino acid other than glutamic acid at a position corresponding to position 3 of SEQ ID NO:1; an amino acid other than leucine at a position corresponding to position 29 of SEQ ID NO:1; an amino acid other than serine at a position corresponding to position 31 of SEQ ID NO:1; an amino acid other than leucine and/or asparagine at a position corresponding to position 37 of SEQ ID NO:1; an amino acid other than histidine at a position corresponding to position 79 of SEQ ID NO:1; an amino acid other than arginine and glutamine and/or tyrosine at a position corresponding to position 80 of SEQ ID NO:1; an amino acid other than tyrosine at a position corresponding to position 81 of SEQ ID NO:1; an amino acid other than methionine at a position corresponding to position 83 of SEQ ID NO:1; an amino acid other than alanine at a position corresponding to position 110 of SEQ ID NO:1; an amino acid other than tyrosine at a position corresponding to position 113 of SEQ ID NO:1; an amino acid other than serine at a position corresponding to position 250 of SEQ ID NO:1; an amino acid other than arginine at a position corresponding to position 256 of SEQ ID NO:1; an amino acid other than glutamine at a position corresponding to position 262 of SEQ ID NO:1; an amino acid other than methionine, arginine, and/or glutamine at a position corresponding to position 265 of SEQ ID NO:1; an amino acid other than proline at a position corresponding to position 269 of SEQ ID NO:1; an amino acid other than alanine at a position corresponding to position 274 of SEQ ID NO:1; an amino acid other than threonine and/or alanine at a position corresponding to position 276 of SEQ ID NO:1; an amino acid other than asparagine at a position corresponding to position 277 of SEQ ID NO:1; an amino acid other than threonine at a position corresponding to position 290 of SEQ ID NO:1; an amino acid other than alanine at a position corresponding to position 304 of SEQ ID NO:1; an amino acid other than alanine and/or threonine at a position corresponding to position 305 of SEQ ID NO:1; an amino acid other than serine at a position corresponding to position 306 of SEQ ID NO:1; an amino acid other than alanine at a position corresponding to position 307 of SEQ ID NO:1; an amino acid other than arginine and/or valine at a position corresponding to position 313 of SEQ ID NO:1; an amino acid other than serine, alanine, and/or valine at a position corresponding to position 315 of SEQ ID NO:1; an amino acid other than serine at a position corresponding to position 322 of SEQ ID NO:1; an amino acid other than asparagine at a position corresponding to position 325 of SEQ ID NO:1; an amino acid other than aspartic acid at a position corresponding to position 327 of SEQ ID NO:1; an amino acid other than glutamine at a position corresponding to position 330 of SEQ ID NO:1; an amino acid other than glutamic acid at a position corresponding to position 332 of SEQ ID NO:1; an amino acid other than proline at a position corresponding to position 340 of SEQ ID NO:1; an amino acid other than alanine at a position corresponding to position 345 of SEQ ID NO:1; an amino acid other than alanine at a position corresponding to position 346 of SEQ ID NO:1; an amino acid other than serine at a position corresponding to position 354 of SEQ ID NO:1; an amino acid other than isoleucine and/or methionine at a position corresponding to position 358 of SEQ ID NO:1; an amino acid other than glutamate at a position corresponding to position 365 of SEQ ID NO:1; an amino acid other than serine at a position corresponding to position 370 of SEQ ID NO:1; an amino acid other than glycine at a position corresponding to position 373 of SEQ ID NO:1; an amino acid other than alanine at a position corresponding to position 378 of SEQ ID NO:1; an amino acid other than serine at a position corresponding to position 443 of SEQ ID NO:1; an amino acid other than aspartic acid at a position corresponding to position 453 of SEQ ID NO:1; an amino acid other than serine and/or alanine at a position corresponding to position 458 of SEQ ID NO:1; an amino acid other than leucine at a position corresponding to position 464 of SEQ ID NO:1; an amino acid other than serine at a position corresponding to position 468 of SEQ ID NO:1; an amino acid other than valine at a position corresponding to position 473 of SEQ ID NO:1; an amino acid other than serine at a position corresponding to position 488 of SEQ ID NO:1; an amino acid other than glycine at a position corresponding to position 490 of SEQ ID NO:1; an amino acid other than isoleucine at a position corresponding to position 496 of SEQ ID NO:1; an amino acid other than glutamine at a position corresponding to position 510 of SEQ ID NO:1; an amino acid other than arginine at a position corresponding to position 511 of SEQ ID NO:1; an amino acid other than arginine at a position corresponding to position 527 of SEQ ID NO:1; an amino acid other than leucine at a position corresponding to position 531 of SEQ ID NO:1; an amino acid other than alanine at a position corresponding to position 535 of SEQ ID NO:1; an amino acid other than proline at a position corresponding to position 537 of SEQ ID NO:1; an amino acid other than valine at a position corresponding to position 538 of SEQ ID NO:1; an amino acid other than serine at a position corresponding to position 539 of SEQ ID NO:1; an amino acid other than serine at a position corresponding to position 543 of SEQ ID NO:1; an amino acid other than threonine at a position corresponding to position 553 of SEQ ID NO:1; an amino acid other than threonine at a position corresponding to position 564 of SEQ ID NO:1; an amino acid other than leucine at a position corresponding to position 565 of SEQ ID NO:1; an amino acid other than proline at a position corresponding to position 577 of SEQ ID NO:1; an amino acid other than alanine at a position corresponding to position 582 of SEQ ID NO:1; an amino acid other than proline at a position corresponding to position 603 of SEQ ID NO:1; an amino acid other than proline at a position corresponding to position 606 of SEQ ID NO:1; an amino acid other than threonine and/or alanine at a position corresponding to position 611 of SEQ ID NO:1; an amino acid other than leucine at a position corresponding to position 613 of SEQ ID NO:1; an amino acid other than proline at a position corresponding to position 624 of SEQ ID NO:1; an amino acid other than methionine at a position corresponding to position 637 of SEQ ID NO:1; an amino acid other than proline at a position corresponding to position 644 of SEQ ID NO:1; an amino acid other than alanine at a position corresponding to position 651 of SEQ ID NO:1; an amino acid other than serine at a position corresponding to position 654 of SEQ ID NO:1; an amino acid other than alanine at a position corresponding to position 678 of SEQ ID NO:1; an amino acid other than proline at a position corresponding to position 679 of SEQ ID NO:1; an amino acid other than aspartic acid at a position corresponding to position 682 of SEQ ID NO:1; an amino acid other than histidine at a position corresponding to position 685 of SEQ ID NO:1; an amino acid other than serine at a position corresponding to position 686 of SEQ ID NO:1; an amino acid other than glycine at a position corresponding to position 688 of SEQ ID NO:1; an amino acid other than glutamic acid at a position corresponding to position 689 of SEQ ID NO:1; an amino acid other than methionine at a position corresponding to position 691 of SEQ ID NO:1; an amino acid other than alanine at a position corresponding to position 695 of SEQ ID NO:1; an amino acid other than alanine at a position corresponding to position 697 of SEQ ID NO:1; an amino acid other than methionine at a position corresponding to position 698 of SEQ ID NO:1; an amino acid other than threonine at a position corresponding to position 704 of SEQ ID NO:1; and an amino acid other than leucine at a position corresponding to position 710 of SEQ ID NO:1.

Embodiment 3. The genetically modified CCNT1 gene of any prior embodiment, wherein the protein encoded by the genetically modified CCNT1 gene comprises one, some or all of: proline at a position corresponding to position 31 of SEQ ID NO:1; tyrosine at a position corresponding to position 37 of SEQ ID NO:1; proline at a position corresponding to position 79 of SEQ ID NO:1; glycine at a position corresponding to position 80 of SEQ ID NO:1; asparagine at a position corresponding to position 81 of SEQ ID NO:1; valine at a position corresponding to position 83 of SEQ ID NO:1; threonine at a position corresponding to position 110 of SEQ ID NO:1; asparagine at a position corresponding to position 250 of SEQ ID NO:1; tryptophan at a position corresponding to position 256 of SEQ ID NO:1; glutamic acid at a position corresponding to position 262 of SEQ ID NO:1; lysine at a position corresponding to position 265 of SEQ ID NO:1; alanine at a position corresponding to position 269 of SEQ ID NO:1; threonine at a position corresponding to position 274 of SEQ ID NO:1; lysine at a position corresponding to position 277 of SEQ ID NO:1; serine at a position corresponding to position 290 of SEQ ID NO:1; serine at a position corresponding to position 305 of SEQ ID NO:1; threonine at a position corresponding to position 306 of SEQ ID NO:1; threonine at a position corresponding to position 307 of SEQ ID NO:1; leucine at a position corresponding to position 313 of SEQ ID NO:1; valine at a position corresponding to position 315 of SEQ ID NO:1; serine at a position corresponding to position 316 of SEQ ID NO:1; asparagine at a position corresponding to position 322 of SEQ ID NO:1; serine at a position corresponding to position 325 of SEQ ID NO:1; glutamic acid at a position corresponding to position 327 of SEQ ID NO:1; proline at a position corresponding to position 330 of SEQ ID NO:1; lysine at a position corresponding to position 332 of SEQ ID NO:1; serine at a position corresponding to position 340 of SEQ ID NO:1; proline at a position corresponding to position 345 of SEQ ID NO:1; threonine at a position corresponding to position 346 of SEQ ID NO:1; asparagine at a position corresponding to position 354 of SEQ ID NO:1; threonine at a position corresponding to position 358 of SEQ ID NO:1; proline at a position corresponding to position 365 of SEQ ID NO:1; asparagine at a position corresponding to position 370 of SEQ ID NO:1; isoleucine at a position corresponding to position 373 of SEQ ID NO:1; asparagine at a position corresponding to position 378 of SEQ ID NO:1; histidine at a position corresponding to position 429 of SEQ ID NO:1; glycine at a position corresponding to position 443 of SEQ ID NO:1; glutamic acid at a position corresponding to position 453 of SEQ ID NO:1; threonine at a position corresponding to position 458 of SEQ ID NO:1; isoleucine at a position corresponding to position 464 of SEQ ID NO:1; glycine at a position corresponding to position 468 of SEQ ID NO:1; alanine at a position corresponding to position 473 of SEQ ID NO:1; alanine at a position corresponding to position 488 of SEQ ID NO:1; alanine at a position corresponding to position 490 of SEQ ID NO:1; valine at a position corresponding to position 496 of SEQ ID NO:1; histidine at a position corresponding to position 510 of SEQ ID NO:1; lysine at a position corresponding to position 511 of SEQ ID NO:1; lysine at a position corresponding to position 527 of SEQ ID NO:1; serine at a position corresponding to position 531 of SEQ ID NO:1; valine at a position corresponding to position 535 of SEQ ID NO:1; threonine at a position corresponding to position 537 of SEQ ID NO:1; glycine at a position corresponding to position 538 of SEQ ID NO:1; asparagine at a position corresponding to position 539 of SEQ ID NO:1; glycine at a position corresponding to position 543 of SEQ ID NO:1; asparagine at a position corresponding to position 553 of SEQ ID NO:1; serine at a position corresponding to position 564 of SEQ ID NO:1; phenylalanine at a position corresponding to position 565 of SEQ ID NO:1; serine at a position corresponding to position 577 of SEQ ID NO:1; glycine at a position corresponding to position 582 of SEQ ID NO:1; serine at a position corresponding to position 599 of SEQ ID NO:1; serine at a position corresponding to position 603 of SEQ ID NO:1; serine at a position corresponding to position 606 of SEQ ID NO:1; glycine at a position corresponding to position 611 of SEQ ID NO:1; methionine at a position corresponding to position 613 of SEQ ID NO:1; serine at a position corresponding to position 624 of SEQ ID NO:1; serine at a position corresponding to position 637 of SEQ ID NO:1; threonine at a position corresponding to position 644 of SEQ ID NO:1; threonine at a position corresponding to position 651 of SEQ ID NO:1; threonine at a position corresponding to position 654 of SEQ ID NO:1; proline at a position corresponding to position 678 of SEQ ID NO:1; threonine at a position corresponding to position 679 of SEQ ID NO:1; glutamic acid at a position corresponding to position 682 of SEQ ID NO:1; arginine at a position corresponding to position 685 of SEQ ID NO:1; proline at a position corresponding to position 686 of SEQ ID NO:1; serine at a position corresponding to position 688 of SEQ ID NO:1; aspartic acid at a position corresponding to position 689 of SEQ ID NO:1; leucine at a position corresponding to position 691 of SEQ ID NO:1; serine at a position corresponding to position 695 of SEQ ID NO:1; glycine at a position corresponding to position 697 of SEQ ID NO:1; isoleucine at a position corresponding to position 698 of SEQ ID NO:1; asparagine at a position corresponding to position 704 of SEQ ID NO:1; and proline at a position corresponding to position 710 of SEQ ID NO:1.

Embodiment 4. A genetically modified XPO1 gene encoding a protein comprising a sequence with at least 80%, at least 85%, at least 90%, or at least 95% sequence identity to SEQ ID NO:7 and having at least one, at least two, or all three of: threonine at a position corresponding to position 411 of SEQ ID NO:7; valine at a position corresponding to position 412 of SEQ ID NO:7; and serine at a position corresponding to position 414 of SEQ ID NO:7.

Embodiment 5. The genetically modified XPO1 gene of embodiment 4, wherein the protein encoded by the genetically modified XPO1 gene comprises one, some, or all of: an amino acid other than aspartic acid at a position corresponding to position 100 of SEQ ID NO:7; an amino acid other than alanine at a position corresponding to position 118 of SEQ ID NO:7; an amino acid other than glycine at a position corresponding to position 151 of SEQ ID NO:7; an amino acid other than alanine at a position corresponding to position 191 of SEQ ID NO:7; an amino acid other than serine at a position corresponding to position 215 of SEQ ID NO:7; an amino acid other than glutamic acid at a position corresponding to position 284 of SEQ ID NO:7; an amino acid other than valine at a position corresponding to position 306 of SEQ ID NO:7; an amino acid other than glycine at a position corresponding to position 334 of SEQ ID NO:7; an amino acid other than leucine at a position corresponding to position 337 of SEQ ID NO:7; an amino acid other than alanine at a position corresponding to position 346 of SEQ ID NO:7; an amino acid other than isoleucine at a position corresponding to position 402 of SEQ ID NO:7; an amino acid other than isoleucine at a position corresponding to position 474 of SEQ ID NO:7; an amino acid other than lysine at a position corresponding to position 478 of SEQ ID NO:7; an amino acid other than glutamine at a position corresponding to position 481 of SEQ ID NO:7; an amino acid other than alanine at a position corresponding to position 869 of SEQ ID NO:7; an amino acid other than glycine at a position corresponding to position 909 of SEQ ID NO:7; an amino acid other than proline at a position corresponding to position 961 of SEQ ID NO:7; an amino acid other than serine at a position corresponding to position 966 of SEQ ID NO:7; an amino acid other than serine at a position corresponding to position 969 of SEQ ID NO:7; an amino acid other than valine and/or methionine at a position corresponding to position 972 of SEQ ID NO:7; an amino acid other than isoleucine at a position corresponding to position 974 of SEQ ID NO:7; an amino acid other than aspartic acid at a position corresponding to position 976 of SEQ ID NO:7; an amino acid other than threonine at a position corresponding to position 1040 of SEQ ID NO:7; an amino acid other than glycine at a position corresponding to position 1043 of SEQ ID NO:7; an amino acid other than glutamine at a position corresponding to position 1046 of SEQ ID NO:7; an amino acid other than leucine at a position corresponding to position 1052 of SEQ ID NO:7; and an amino acid other than leucine at a position corresponding to position 1060 of SEQ ID NO:7.

Embodiment 6. The genetically modified XPO1 gene of any one of embodiments 4-5, wherein the protein encoded by the genetically modified XPO1 gene comprises one, some, or all of: glutamic acid at a position corresponding to position 100 of SEQ ID NO:7; threonine at a position corresponding to position 118 of SEQ ID NO:7; serine at a position corresponding to position 151 of SEQ ID NO:7; serine at a position corresponding to position 191 of SEQ ID NO:7; asparagine at a position corresponding to position 215 of SEQ ID NO:7; valine at a position corresponding to position 284 of SEQ ID NO:7; leucine at a position corresponding to position 306 of SEQ ID NO:7; aspartic acid at a position corresponding to position 334 of SEQ ID NO:7; isoleucine at a position corresponding to position 337 of SEQ ID NO:7; threonine at a position corresponding to position 346 of SEQ ID NO:7; valine at a position corresponding to position 402 of SEQ ID NO:7; arginine at a position corresponding to position 474 of SEQ ID NO:7; glutamic acid at a position corresponding to position 478 of SEQ ID NO:7; histidine at a position corresponding to position 481 of SEQ ID NO:7; threonine at a position corresponding to position 869 of SEQ ID NO:7; alanine at a position corresponding to position 909 of SEQ ID NO:7; serine at a position corresponding to position 961 of SEQ ID NO:7; asparagine at a position corresponding to position 966 of SEQ ID NO:7; asparagine at a position corresponding to position 969 of SEQ ID NO:7; isoleucine at a position corresponding to position 972 of SEQ ID NO:7; leucine at a position corresponding to position 974 of SEQ ID NO:7; glutamic acid at a position corresponding to position 976 of SEQ ID NO:7; isoleucine at a position corresponding to position 1040 of SEQ ID NO:7; arginine at a position corresponding to position 1043 of SEQ ID NO:7; aspartic acid at a position corresponding to position 1046 of SEQ ID NO:7; arginine at a position corresponding to position 1052 of SEQ ID NO:7; and phenylalanine at a position corresponding to position 1060 of SEQ ID NO:7.

Embodiment 7. A genetically modified cell comprising at least one of: one or more copies of the genetically modified gene of any one of embodiments 1-3; and one or more copies of the genetically modified gene of embodiments 4-6.

Embodiment 8. The cell of embodiment 7, wherein the cell is an immune cell or a precursor of an immune cell.

Embodiment 9. The cell of any one of embodiments 7-8, wherein the cell is selected from the group consisting of a hematopoietic stem cell, a myeloid progenitor cell, a lymphoid progenitor cell, a myeoblast, a monocyte, a macrophage, a dendritic cell, a small lymphocyte, a T cell, and an astrocyte.

Embodiment 10. The cell of any one of embodiments 7-9, wherein the cell is a T cell or a precursor thereof.

Embodiment 11. The cell of any one of embodiments 7-10, wherein the cell is a CD4+ T cell or a precursor thereof.

Embodiment 12. The cell of any one of embodiments 7-11, wherein the cell is a mammalian cell.

Embodiment 13. The cell of any one of embodiments 7-12, wherein the cell comprises at least one of: two copies of the genetically modified CCNT1 gene; and two copies of the genetically modified XPO1 gene.

Embodiment 14. The cell of any one of embodiments 7-13, wherein the cell is devoid of at least one of: a CCNT1 gene having an amino acid other than a tyrosine at a position corresponding to position 261 of SEQ ID NO:1; and an XPO1 gene having at least one, at least two, or all three of an amino acid other than a threonine at a position corresponding to position 411 of SEQ ID NO:7, an amino acid other than a methionine at a position corresponding to position 412 of SEQ ID NO:7, and an amino acid other than a phenylalanine at a position corresponding to position 414 of SEQ ID NO:7.

Embodiment 15. A method of treating a subject infected with a virus, the method comprising introducing the genetically modified cell of any one of embodiments 7-14 in the subject, wherein the genetically modified cell is of a cell type susceptible to infection with the virus or a precursor of a cell type susceptible to infection with the virus.

Embodiment 16. The method of embodiment 15, wherein the subject is a mammal.

Embodiment 17. The method of any one of embodiments 15-16, wherein the subject is a human.

Embodiment 18. The method of any one of embodiments 15-17, wherein the virus is selected from the group consisting of a lentivirus and a deltaretrovirus.

Embodiment 19. The method of any one of embodiments 15-18, wherein the virus is selected from the group consisting of a primate immunodeficiency virus and a primate T-lymphotropic virus.

Embodiment 20. The method of any one of embodiments 15-19, wherein the virus is selected from the group consisting of a human immunodeficiency virus and a human T-lymphotropic virus.

Embodiment 21. The method of any one of embodiments 15-20, wherein the virus is a human immunodeficiency virus.

Embodiment 22. The method of any one of embodiments 15-21, wherein the cell is autologous to the subject.

Embodiment 23. The method of any one of embodiments 15-22, wherein the introducing comprises introducing the cell into the bloodstream of the subject.

Embodiment 24. The method of any one of embodiments 15-23, wherein the introducing comprises injecting or infusing the cell into the bloodstream of the subject.

What is claimed is:

1. A genetically modified cell comprising one or more copies of a genetically modified CCNT1 gene encoding a protein comprising a sequence with at least 95% sequence identity to SEQ ID NO:1 and comprising a tyrosine at a position corresponding to position 261 of SEQ ID NO:1, wherein the cell is a human cell and is an immune cell or a precursor of an immune cell, and wherein the cell is devoid of any native CCNT1 genes.

2. The cell of claim 1, wherein the cell is selected from the group consisting of a hematopoietic stem cell, a myeloid progenitor cell, a lymphoid progenitor cell, a myeoblast, a monocyte, a macrophage, a dendritic cell, a small lymphocyte, a T cell, and an astrocyte.

3. The cell of claim 1, wherein the cell is a T cell or a precursor thereof.

4. The cell of claim 1, wherein the cell is a CD4+ T cell or a precursor thereof.

5. The cell of claim 1, wherein the cell comprises two copies of the genetically modified CCNT1 gene.

6. The cell of claim 1, wherein the protein encoded by the genetically modified CCNT1 gene comprises one or more of: an amino acid other than glutamic acid at a position corresponding to position 3 of SEQ ID NO:1; an amino acid other than leucine at a position corresponding to position 29 of SEQ ID NO:1; an amino acid other than serine at a position corresponding to position 31 of SEQ ID NO:1; an amino acid other than leucine and/or asparagine at a position corresponding to position 37 of SEQ ID NO:1; an amino acid other than histidine at a position corresponding to position 79 of SEQ ID NO:1; an amino acid other than arginine and glutamine and/or tyrosine at a position corresponding to position 80 of SEQ ID NO:1; an amino acid other than tyrosine at a position corresponding to position 81 of SEQ ID NO:1; an amino acid other than methionine at a position corresponding to position 83 of SEQ ID NO:1; an amino acid other than alanine at a position corresponding to position 110 of SEQ ID NO:1; an amino acid other than tyrosine at a position corresponding to position 113 of SEQ ID NO:1; an amino acid other than serine at a position corresponding to position 250 of SEQ ID NO:1; an amino acid other than arginine at a position corresponding to position 256 of SEQ ID NO:1; an amino acid other than glutamine at a position corresponding to position 262 of SEQ ID NO:1; an amino acid other than methionine, arginine, and/or glutamine at a position corresponding to position 265 of SEQ ID NO:1; an amino acid other than proline at a position corresponding to position 269 of SEQ ID NO:1; an amino acid other than alanine at a position corresponding to position 274 of SEQ ID NO:1; an amino acid other than threonine and/or alanine at a position corresponding to position 276 of SEQ ID NO:1; an amino acid other than asparagine at a position corresponding to position 277 of SEQ ID NO:1; an amino acid other than threonine at a position corresponding to position 290 of SEQ ID NO:1; an amino acid other than alanine at a position corresponding to position 304 of SEQ ID NO:1; an amino acid other than alanine and/or threonine at a position corresponding to position 305 of SEQ ID NO:1; an amino acid other than serine at a position corresponding to position 306 of SEQ ID NO:1; an amino acid other than alanine at a position corresponding to position 307 of SEQ ID NO:1; an amino acid other than arginine and/or valine at a position corresponding to position 313 of SEQ ID NO:1; an amino acid other than serine, alanine, and/or valine at a position corresponding to position 315 of SEQ ID NO:1; an amino acid other than serine at a position corresponding to position 322 of SEQ ID NO:1; an amino acid other than asparagine at a position corresponding to position 325 of SEQ ID NO:1; an amino acid other than aspartic acid at a position corresponding to position 327 of SEQ ID NO:1; an amino acid other than glutamine at a position corresponding to position 330 of SEQ ID NO:1; an amino acid other than glutamic acid at a position corresponding to position 332 of SEQ ID NO:1; an amino acid other than proline at a position corresponding to position 340 of SEQ ID NO:1; an amino acid other than alanine at a position corresponding to position 345 of SEQ ID NO:1; an amino acid other than alanine at a position corresponding to position 346 of SEQ ID NO:1; an amino acid other than serine at a position corresponding to position 354 of SEQ ID NO:1; an amino acid other than isoleucine and/or methionine at a position corresponding to position 358 of SEQ ID NO:1; an amino acid other than glutamine at a position corresponding to position 365 of SEQ ID NO:1; an amino acid other than serine at a position corresponding to position 370 of SEQ ID NO:1; an amino acid other than glycine at a position corresponding to position 373 of SEQ ID NO:1; an amino acid other than alanine at a position corresponding to position 378 of SEQ ID NO:1; an amino acid other than serine at a position corresponding to position 443 of SEQ ID NO:1; an amino acid other than aspartic acid at a position corresponding to position 453 of SEQ ID NO:1; an amino acid other than serine and/or alanine at a position corresponding to position 458 of SEQ ID NO:1; an amino acid other than leucine at a position corresponding to position 464 of SEQ ID NO:1; an amino acid other than serine at a position corresponding to position 468 of SEQ ID NO:1; an amino acid other than valine at a position corresponding to position 473 of SEQ ID NO:1; an amino acid other than serine at a position corresponding to position 488 of SEQ ID NO:1; an amino acid other than glycine at a position corresponding to position 490 of SEQ ID NO:1; an amino acid other than isoleucine at a position corresponding to position 496 of SEQ ID NO:1; an amino acid other than glutamine at a position corresponding to position 510 of SEQ ID NO:1; an amino acid other than arginine at a position corresponding to position 511 of SEQ ID NO:1; an amino acid other than arginine at a position corresponding to position 527 of SEQ ID NO:1; an amino acid other than leucine at a position corresponding to position 531 of SEQ ID NO:1; an amino acid other than alanine at a position corresponding to position 535 of SEQ ID NO:1; an amino acid other than proline at a position corresponding to position 537 of SEQ ID NO:1; an amino acid other than valine at a position corresponding to position 538 of SEQ ID NO:1; an amino acid other than serine at a position corresponding to position 539 of SEQ ID NO:1; an amino acid other than serine at a position corresponding to position 543 of SEQ ID NO:1; an amino acid other than threonine at a position corresponding to position 553 of SEQ ID NO:1; an amino acid other than threonine at a position corresponding to position 564 of SEQ ID NO:1; an amino acid other than leucine at a position corresponding to position 565 of SEQ ID NO:1; an amino acid other than proline at a position corresponding to position 577 of SEQ ID NO:1; an amino acid other than alanine at a position corresponding to position 582 of SEQ ID NO:1; an amino acid other than proline at a position corresponding to position 603 of SEQ ID NO:1; an amino acid other than proline at a position corresponding to position 606 of SEQ ID NO:1; an amino acid other than threonine and/or alanine at a position corresponding to position 611 of SEQ ID NO:1; an amino acid other than leucine at a position corresponding to position 613 of SEQ ID NO:1; an amino acid other than proline at a position corresponding to position 624 of SEQ ID NO:1; an amino acid other than methionine at a position corresponding to position 637 of SEQ ID NO:1; an amino acid other than proline at a position corresponding to position 644 of SEQ ID NO:1; an amino acid other than alanine at a position corresponding to position 651 of SEQ ID NO:1; an amino acid other than serine at a position corresponding to position 654 of SEQ ID NO:1; an amino acid other than alanine at a position corresponding to position 678 of SEQ ID NO:1; an amino acid other than proline at a position corresponding to position 679 of SEQ ID NO:1; an amino acid other than aspartic acid at a position corresponding to position 682 of SEQ ID NO:1; an amino acid other than histidine at a position corresponding to position 685 of SEQ ID NO:1; an amino acid other than serine at a position corresponding to position 686 of SEQ ID NO:1; an amino acid other than glycine at a position corresponding to position 688 of SEQ ID NO:1; an amino acid other than glutamic acid at a position corresponding to position 689 of SEQ ID NO:1; an amino acid other than methionine at a position corresponding to position 691 of SEQ ID NO:1; an amino acid other than alanine at a position corresponding to position 695 of SEQ ID NO:1; an amino acid other than alanine at a position corresponding to position 697 of SEQ ID NO:1; an amino acid other than methionine at a position corresponding to position 698 of SEQ ID NO:1; an amino acid other than threonine at a position corresponding to position 704 of SEQ ID NO:1; and an amino acid other than leucine at a position corresponding to position 710 of SEQ ID NO:1.

7. The cell of claim 1, wherein the protein encoded by the genetically modified CCNT1 gene comprises one or more of: proline at a position corresponding to position 31 of SEQ ID NO:1; tyrosine at a position corresponding to position 37 of SEQ ID NO:1; proline at a position corresponding to position 79 of SEQ ID NO:1; glycine at a position corresponding to position 80 of SEQ ID NO:1; asparagine at a position corresponding to position 81 of SEQ ID NO:1; valine at a position corresponding to position 83 of SEQ ID NO:1; threonine at a position corresponding to position 110 of SEQ ID NO:1; asparagine at a position corresponding to position 250 of SEQ ID NO:1; tryptophan at a position corresponding to position 256 of SEQ ID NO:1; glutamic acid at a position corresponding to position 262 of SEQ ID NO:1; lysine at a position corresponding to position 265 of SEQ ID NO:1; alanine at a position corresponding to position 269 of SEQ ID NO:1; threonine at a position corresponding to position 274 of SEQ ID NO:1; lysine at a position corresponding to position 277 of SEQ ID NO:1; serine at a position corresponding to position 290 of SEQ ID NO:1; serine at a position corresponding to position 305 of SEQ ID NO:1; threonine at a position corresponding to position 306 of SEQ ID NO:1; threonine at a position corresponding to position 307 of SEQ ID NO:1; leucine at a position corresponding to position 313 of SEQ ID NO:1; valine at a position corresponding to position 315 of SEQ ID NO:1; serine at a position corresponding to position 316 of SEQ ID NO:1; asparagine at a position corresponding to position 322 of SEQ ID NO:1; serine at a position corresponding to position 325 of SEQ ID NO:1; glutamic acid at a position corresponding to position 327 of SEQ ID NO:1; proline at a position corresponding to position 330 of SEQ ID NO:1; lysine at a position corresponding to position 332 of SEQ ID NO:1; serine at a position corresponding to position 340 of SEQ ID NO:1; proline at a position corresponding to position 345 of SEQ ID NO:1; threonine at a position corresponding to position 346 of SEQ ID NO:1; asparagine at a position corresponding to position 354 of SEQ ID NO:1; threonine at a position corresponding to position 358 of SEQ ID NO:1; proline at a position corresponding to position 365 of SEQ ID NO:1; asparagine at a position corresponding to position 370 of SEQ ID NO:1; isoleucine at a position corresponding to position 373 of SEQ ID NO:1; asparagine at a position corresponding to position 378 of SEQ ID NO:1; histidine at a position corresponding to position 429 of SEQ ID NO:1; glycine at a position corresponding to position 443 of SEQ ID NO:1; glutamic acid at a position corresponding to position 453 of SEQ ID NO:1; threonine at a position corresponding to position 458 of SEQ ID NO:1; isoleucine at a position corresponding to position 464 of SEQ ID NO:1; glycine at a position corresponding to position 468 of SEQ ID NO:1; alanine at a position corresponding to position 473 of SEQ ID NO:1; alanine at a position corresponding to position 488 of SEQ ID NO:1; alanine at a position corresponding to position 490 of SEQ ID NO:1; valine at a position corresponding to position 496 of SEQ ID NO:1; histidine at a position corresponding to position 510 of SEQ ID NO:1; lysine at a position corresponding to position 511 of SEQ ID NO:1; lysine at a position corresponding to position 527 of SEQ ID NO:1; serine at a position corresponding to position 531 of SEQ ID NO:1; valine at a position corresponding to position 535 of SEQ ID NO:1; threonine at a position corresponding to position 537 of SEQ ID NO:1; glycine at a position corresponding to position 538 of SEQ ID NO:1; asparagine at a position corresponding to position 539 of SEQ ID NO:1; glycine at a position corresponding to position 543 of SEQ ID NO:1; asparagine at a position corresponding to position 553 of SEQ ID NO:1; serine at a position corresponding to position 564 of SEQ ID NO:1; phenylalanine at a position corresponding to position 565 of SEQ ID NO:1; serine at a position corresponding to position 577 of SEQ ID NO:1; glycine at a position corresponding to position 582 of SEQ ID NO:1; serine at a position corresponding to position 599 of SEQ ID NO:1; serine at a position corresponding to position 603 of SEQ ID NO:1; serine at a position corresponding to position 606 of SEQ ID NO:1; glycine at a position corresponding to position 611 of SEQ ID NO:1; methionine at a position corresponding to position 613 of SEQ ID NO:1; serine at a position corresponding to position 624 of SEQ ID NO:1; serine at a position corresponding to position 637 of SEQ ID NO:1; threonine at a position corresponding to position 644 of SEQ ID NO:1; threonine at a position corresponding to position 651 of SEQ ID NO:1; threonine at a position corresponding to position 654 of SEQ ID NO:1; proline at a position corresponding to position 678 of SEQ ID NO:1; threonine at a position corresponding to position 679 of SEQ ID NO:1; glutamic acid at a position corresponding to position 682 of SEQ ID NO:1; arginine at a position corresponding to position 685 of SEQ ID NO:1; proline at a position corresponding to position 686 of SEQ ID NO:1; serine at a position corresponding to position 688 of SEQ ID NO:1; aspartic acid at a position corresponding to position 689 of SEQ ID NO:1; leucine at a position corresponding to position 691 of SEQ ID NO:1; serine at a position corresponding to position 695 of SEQ ID NO:1; glycine at a position corresponding to position 697 of SEQ ID NO:1; isoleucine at a position corresponding to position 698 of SEQ ID NO:1; asparagine at a position corresponding to position 704 of SEQ ID NO:1; and proline at a position corresponding to position 710 of SEQ ID NO:1.

8. The cell of claim 1, wherein the cell is devoid of a CCNT1 gene encoding an amino acid other than a tyrosine at a position corresponding to position 261 of SEQ ID NO:1.

9. The cell of claim 8, wherein the cell is a T cell or a precursor thereof.

10. The cell of claim 1, wherein the cell is devoid of any CCNT1 genes encoding a cysteine at a position corresponding to position 261 of SEQ ID NO:1.

11. The cell of claim 1, further comprising one or more copies of a genetically modified XPO1 gene encoding a protein comprising a sequence with at least 95% sequence identity to SEQ ID NO:7 and having at least one, at least two, or all three of:
  threonine at a position corresponding to position 411 of SEQ ID NO:7;
  valine at a position corresponding to position 412 of SEQ ID NO:7; and
  serine at a position corresponding to position 414 of SEQ ID NO:7.

12. The cell of claim 11, wherein the cell comprises two copies of the genetically modified XPO1 gene.

13. The cell of claim 11, wherein the cell is devoid of an XPO1 gene having at least one, at least two, or all three of an amino acid other than a threonine at a position corresponding to position 411 of SEQ ID NO:7, an amino acid other than a methionine at a position corresponding to position 412 of SEQ ID NO:7, and an amino acid other than a phenylalanine at a position corresponding to position 414 of SEQ ID NO:7.

14. The cell of claim 11, wherein the protein encoded by the genetically modified XPO1 gene comprises one or more of: an amino acid other than aspartic acid at a position corresponding to position 100 of SEQ ID NO:7; an amino acid other than alanine at a position corresponding to position 118 of SEQ ID NO:7; an amino acid other than glycine at a position corresponding to position 151 of SEQ ID NO:7; an amino acid other than alanine at a position corresponding to position 191 of SEQ ID NO:7; an amino acid other than serine at a position corresponding to position 215 of SEQ ID NO:7; an amino acid other than glutamic acid at a position corresponding to position 284 of SEQ ID NO:7;
  an amino acid other than valine at a position corresponding to position 306 of SEQ ID NO:7; an amino acid other than glycine at a position corresponding to position 334 of SEQ ID NO:7; an amino acid other than leucine at a position corresponding to position 337 of SEQ ID NO:7; an amino acid other than alanine at a position corresponding to position 346 of SEQ ID NO:7; an amino acid other than isoleucine at a position corresponding to position 402 of SEQ ID NO:7; an amino acid other than isoleucine at a position corresponding to position 474 of SEQ ID NO:7; an amino acid other than lysine at a position corresponding to position 478 of SEQ ID NO:7; an amino acid other than glutamine at a position corresponding to position 481 of SEQ ID NO:7; an amino acid other than alanine at a position corresponding to position 869 of SEQ ID NO:7; an amino acid other than glycine at a position corresponding to position 909 of SEQ ID NO:7; an amino acid other than proline at a position corresponding to position 961 of SEQ ID NO:7; an amino acid other than serine at a position corresponding to position 966 of SEQ ID NO:7; an amino acid other than serine at a position corresponding to position 969 of SEQ ID NO:7; an amino acid other than valine and/or methionine at a position corresponding to position 972 of SEQ ID NO:7; an amino acid other than isoleucine at a position corresponding to position 974 of SEQ ID NO:7; an amino acid other than aspartic acid at a position corresponding to position 976 of SEQ ID NO:7; an amino acid other than threonine at a position corresponding to position 1040 of SEQ ID NO:7; an amino acid other than glycine at a position corresponding to position 1043 of SEQ ID NO:7; an amino acid other than glutamine at a position corresponding to position 1046 of SEQ ID NO:7; an amino acid other than leucine at a position corresponding to position 1052 of SEQ ID NO:7; and an amino acid other than leucine at a position corresponding to position 1060 of SEQ ID NO:7.

15. The cell of claim 11, wherein the protein encoded by the genetically modified XPO1 gene comprises one or more of: glutamic acid at a position corresponding to position 100 of SEQ ID NO:7; threonine at a position corresponding to position 118 of SEQ ID NO:7; serine at a position corresponding to position 151 of SEQ ID NO:7; serine at a position corresponding to position 191 of SEQ ID NO:7; asparagine at a position corresponding to position 215 of SEQ ID NO:7; valine at a position corresponding to position 284 of SEQ ID NO:7; leucine at a position corresponding to position 306 of SEQ ID NO:7; aspartic acid at a position corresponding to position 334 of SEQ ID NO:7; isoleucine at a position corresponding to position 337 of SEQ ID NO:7; threonine at a position corresponding to position 346 of SEQ ID NO:7; valine at a position corresponding to position 402 of SEQ ID NO:7; arginine at a position corresponding to position 474 of SEQ ID NO:7; glutamic acid at a position corresponding to position 478 of SEQ ID NO:7; histidine at a position corresponding to position 481 of SEQ ID NO:7; threonine at a position corresponding to position 869 of SEQ ID NO:7; alanine at a position corresponding to position 909 of SEQ ID NO:7; serine at a position corresponding to position 961 of SEQ ID NO:7; asparagine at a position corresponding to position 966 of SEQ ID NO:7; asparagine at a position corresponding to position 969 of SEQ ID NO:7; isoleucine at a position corresponding to position 972 of SEQ ID NO:7; leucine at a position corresponding to position 974 of SEQ ID NO:7; glutamic acid at a position corresponding to position 976 of SEQ ID NO:7; isoleucine at a position corresponding to position 1040 of SEQ ID NO:7; arginine at a position corresponding to position 1043 of SEQ ID NO:7; aspartic acid at a position corresponding to position 1046 of SEQ ID NO:7; arginine at a position corresponding to position 1052 of SEQ ID NO:7; and phenylalanine at a position corresponding to position 1060 of SEQ ID NO:7.

16. The cell of claim 11, wherein the cell is devoid of at least one of:
   a CCNT1 gene having an amino acid other than a tyrosine at a position corresponding to position 261 of SEQ ID NO:1; and
   an XPO1 gene having at least one, at least two, or all three of an amino acid other than a threonine at a position corresponding to position 411 of SEQ ID NO:7, an amino acid other than a methionine at a position corresponding to position 412 of SEQ ID NO:7, and an amino acid other than a phenylalanine at a position corresponding to position 414 of SEQ ID NO:7.

17. A method of treating a subject infected with a virus selected from the group consisting of a primate immunodeficiency virus and a primate T-lymphotropic virus, the method comprising introducing the genetically modified cell of claim 1 in the subject, wherein the genetically modified cell is of a cell type susceptible to infection with the virus or a precursor of a cell type susceptible to infection with the virus.

18. The method of claim 17, wherein the subject is a mammal.

19. The method of claim 17, wherein the subject is a human.

20. The method of claim 17, wherein the virus is selected from the group consisting of a human immunodeficiency virus and a human T-lymphotropic virus.

21. The method of claim 17, wherein the virus is a human immunodeficiency virus.

22. The method of claim 17, wherein the cell is autologous to the subject.

23. The method of claim 17, wherein the introducing comprises introducing the cell into the bloodstream of the subject.

24. The method of claim 17, wherein the introducing comprises injecting or infusing the cell into the bloodstream of the subject.

* * * * *